(12) United States Patent
Beattie et al.

(10) Patent No.: US 8,835,444 B2
(45) Date of Patent: *Sep. 16, 2014

(54) CYCLOHEXYL AMIDE DERIVATIVES AS CRF RECEPTOR ANTAGONISTS

(75) Inventors: David Beattie, Horsham (GB); Ian Bruce, Billingshurst (GB); Anny-Odile Colson, Horsham (GB); Andrew James Culshaw, Greenford (GB); Thomas Sharp, Brighton (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/576,040

(22) PCT Filed: Jan. 31, 2011

(86) PCT No.: PCT/EP2011/051293
§ 371 (c)(1),
(2), (4) Date: Jul. 30, 2012

(87) PCT Pub. No.: WO2011/095450
PCT Pub. Date: Aug. 11, 2011

(65) Prior Publication Data
US 2012/0316185 A1      Dec. 13, 2012

Related U.S. Application Data

(60) Provisional application No. 61/300,576, filed on Feb. 2, 2010, provisional application No. 61/424,258, filed on Dec. 17, 2010.

(51) Int. Cl.
| | | |
|---|---|---|
| C07C 233/79 | (2006.01) |
| C07D 213/82 | (2006.01) |
| C07D 231/12 | (2006.01) |
| C07D 231/38 | (2006.01) |
| C07D 249/08 | (2006.01) |
| C07D 401/12 | (2006.01) |
| C07D 231/16 | (2006.01) |
| C07D 473/00 | (2006.01) |
| C07D 231/54 | (2006.01) |
| C07D 231/14 | (2006.01) |
| C07D 405/04 | (2006.01) |
| C07D 491/052 | (2006.01) |
| C07D 231/20 | (2006.01) |
| C07D 231/56 | (2006.01) |
| C07D 401/04 | (2006.01) |
| C07D 471/04 | (2006.01) |
| C07D 401/14 | (2006.01) |

(52) U.S. Cl.
CPC ............ *C07D 213/82* (2013.01); *C07D 231/16* (2013.01); *C07D 473/00* (2013.01); *C07D 231/54* (2013.01); *C07D 231/14* (2013.01); *C07D 405/04* (2013.01); *C07D 249/08* (2013.01); *C07C 233/79* (2013.01); *C07D 491/052* (2013.01); *C07C 2101/14* (2013.01); *C07D 231/38* (2013.01); *C07D 231/20* (2013.01); *C07D 231/56* (2013.01); *C07D 231/12* (2013.01); *C07D 401/04* (2013.01); *C07D 471/04* (2013.01); *C07D 401/12* (2013.01); *C07D 401/14* (2013.01)
USPC ............ 514/263.1; 514/265.1; 514/300; 514/303; 544/277; 544/280; 546/119; 546/121

(58) Field of Classification Search
None
See application file for complete search history.

(56) References Cited

U.S. PATENT DOCUMENTS 8,273,900 B2 * 9/2012 Beattie et al. ............ 548/356.1
8,614,213 B2 * 12/2013 Beattie et al. ............ 514/235.5

FOREIGN PATENT DOCUMENTS

WO      2010/015655 A1     2/2010

OTHER PUBLICATIONS

P. Gilligan et al., Expert Opin. Ther. Patents, 16(7):913-924 (2006).
P. Gilligan, Expert Opin. Ther. Patents, 16(7):913-924 (2006).

* cited by examiner

*Primary Examiner* — Kamal Saeed
(74) *Attorney, Agent, or Firm* — Joshua Roth

(57) ABSTRACT

There are described cyclohexyl amide derivatives useful as corticotropin releasing factor (CRF) receptor antagonists Formula (I).

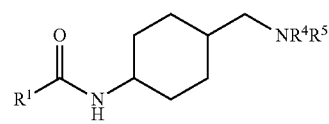

9 Claims, No Drawings

CYCLOHEXYL AMIDE DERIVATIVES AS CRF RECEPTOR ANTAGONISTS

This application is a U.S. National Phase filing of International Application No. PCT/EP2011/051293 filed 31 Jan. 2011, which claims priority to U.S. Provisional Application Ser. Nos. 61/300,576, filed 2 Feb. 2010 and 61/424,258, filed 17 Dec. 2010, the contents of which are incorporated herein by reference in their entirety.

FIELD OF THE INVENTION

The present invention relates to cyclohexyl amide derivatives, their preparation, their use as pharmaceuticals and pharmaceutical compositions containing them. More particularly the present invention relates to their use as corticotropin releasing factor (CRF) receptor antagonists.

SUMMARY OF THE INVENTION

In a first aspect of the invention we provide a compound of formula I;

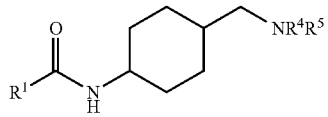

in which $R^1$ is a group A or B:

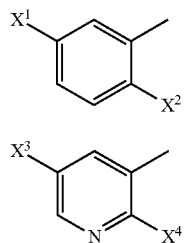

wherein $X^1$ is haloalkyl C1 to 10;
$X^2$ is halogen;
$X^3$ is halogen or haloalkyl;
$X^4$ is alkyl C1 to 10;
and
(1) when $R^1$ is a group A
$R^4$ is a group of formula II or $R^4$ together with $R^5$ and the nitrogen to which they are attached forms a group of formula III;

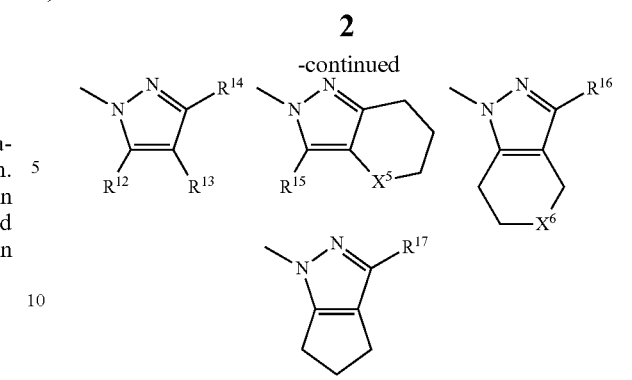

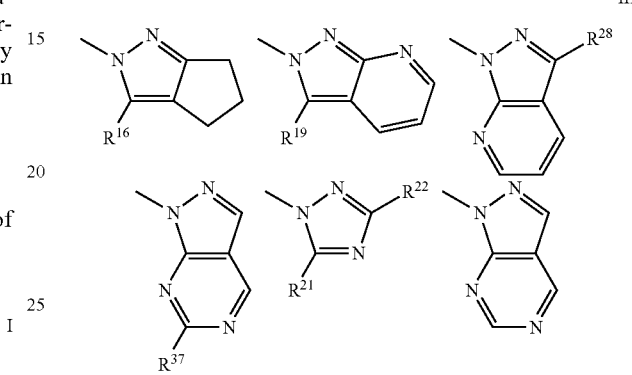

$R^5$ is hydrogen or together with $R^4$ and the nitrogen to which they are attached forms a group of formula III;
$X^5$ is O or —$CH_2$—;
$X^6$ is O or —$CH_2$—;
$R^6$ is halophenyl, optionally substituted by alkoxy C1 to 6;
$R^7$ is alkyl C1 to 6;
$R^8$ is hydrogen or pyridin-3-yl;
$R^9$ is hydrogen or methyl;
$R^{10}$ is —COOH or —$CHR^{36}COOH$;
$R^{12}$ is hydrogen, alkyl C1 to 6, alkoxy C1 to 6, hydroxyalkyl C1 to 6, —$CO_2R^{11}$ or phenyl optionally substituted by fluoro;
$R^{11}$ is alkyl C1 to 6;
$R^{13}$ is hydrogen, deuterium, alkyl C1 to 6 or chloro;
$R^{14}$ is hydrogen, alkyl C1 to 6, methoxy, hydroxyalkyl C1 to 6, ethoxycarbonyl, pyridyl, benzo[1,3]dioxo-5-yl or phenyl, optionally substituted by fluoro, alkoxy C1 to 6;
$R^{15}$ is hydrogen or methyl;
$R^{16}, R^{17}, R^{18}, R^{19}, R^{20}$, which may be the same or different, are each hydrogen or alkyl C1 to 6;
$R^{21}$ is alkyl C1 to 6;
$R^{22}$ is haloalkyl C1 to 6;
$R^{36}$ and $R^{37}$, which may be the same or different are each hydrogen or alkyl C1 to 6;
(2) when $R^1$ is a group B:
$R^4$ is a group of formula IV or $R^4$ together with $R^5$ and the nitrogen to which they are attached forms a group of formula V;

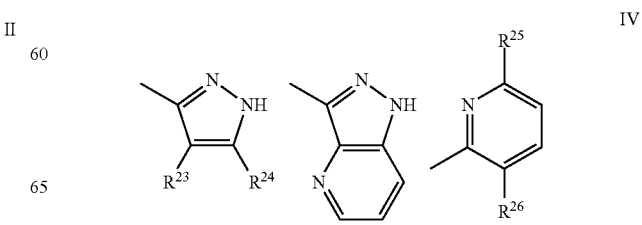

-continued

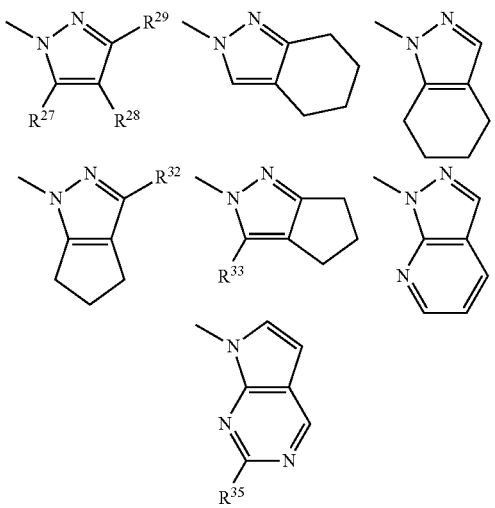

R²³ and R²⁴, which may be the same or different, are each alkyl C1 to 6;
R²⁵ is alkoxy C1 to 6;
R²⁶ is hydrogen or halogen;
R²⁷ is hydrogen, alkyl C1 to 3, methoxy or hydroxymethyl or haloalkyl;
R²⁸ is hydrogen, alkyl C1 to 6 or halogen;
R²⁹ is hydrogen, alkyl C1 to 3, alkoxy C1 to 6, hydroxyalkyl C1 to 6, haloalkyl C1 to 6, pyridyl or phenyl optionally substituted by fluorine;
R³² and R³³, which may be the same or different, are each hydrogen or alkyl C1 to 6;
R³⁵ is halogen;
and isomers thereof;
in free form or in salt form;
provided that the compound of formula I is not:
trans-2-chloro-N-[4-(3,5-dimethyl-pyrazol-1-ylmethyl)-cyclohexyl]-5-trifluoro methyl-benzamide;
trans-2-chloro-N-[4-(3,5-di-(d3)-methyl-pyrazol-1-ylmethyl)-cyclohexyl]-5-trifluoro methyl-benzamide;
trans-2-chloro-N-[4-(5-methyl-pyrazol-1-ylmethyl)-cyclohexyl]-5-trifluoromethyl-benzamide;
trans-2-chloro-N-[4-(3-methyl-pyrazol-1-ylmethyl)-cyclohexyl]-5-trifluoromethyl-benzamide;
trans-2-chloro-N-{4-[3-(4-methoxy-phenyl)-pyrazol-1-ylmethyl]-cyclohexyl}-5-trifluoromethyl-benzamide;
trans-5-chloro-N-[4-(4-chloro-3,5-dimethyl-pyrazol-1-ylmethyl)-cyclohexyl]-2-methyl-nicotinamide;
trans-5-chloro-2-methyl-N-[4-(3,4,5-trimethyl-pyrazol-1-ylmethyl)-cyclohexyl]-nicotinamide;
trans-2-chloro-N-(4-((4-(4-chlorophenyl)-5-methyl-1H-pyrazol-3-ylamino)methyl)cyclohexyl)-5-(trifluoromethyl)benzamide;
trans-2-chloro-N-{4-[(4-pyridin-3-yl-2H-pyrazol-3-ylamino)-methyl]-cyclohexyl}-5-trifluoromethyl-benzamide;
trans-2-chloro-N-(4-{[4-(4-fluoro-phenyl)-5-methyl-1H-pyrazol-3-ylamino]-methyl}-cyclohexyl)-5-trifluoromethyl-benzamide;
2-chloro-N-[4-(4-chloro-3,5-dimethyl-pyrazol-1-ylmethyl)-cyclohexyl]-5-trifluoro methyl-benzamide;
2-chloro-5-trifluoromethyl-N-[4-(3,4,5-trimethyl-pyrazol-1-ylmethyl)-cyclohexyl]-benzamide;
2-chloro-N-[4-(3-phenyl-pyrazol-1-ylmethyl)-cyclohexyl]-5-trifluoromethyl-benzamide;
5-chloro-N-[4-(3,5-dimethyl-pyrazol-1-ylmethyl)-cyclohexyl]-2-methyl-nicotinamide;
trans-5-chloro-2-methyl-N-[4-(3-methyl-5-trifluoromethyl-pyrazol-1-ylmethyl)-cyclohexyl]-nicotinamide; and
trans-5-chloro-2-methyl-N-[4-(5-methyl-3-trifluoromethyl-pyrazol-1-ylmethyl)-cyclohexyl]-nicotinamide.

For purposes of interpreting this specification, the following definitions will apply and whenever appropriate, terms used in the singular will also include the plural and vice versa.

As used herein, the term "alkyl" refers to a fully saturated, branched, unbranched or cyclic hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "sulphonyl" refers to R—SO₂—, wherein R is hydrogen, alkyl, aryl, heteroaryl, aryl-alkyl, heteroaryl-alkyl, alkoxy, aryloxy, cycloalkyl, or heterocyclyl. As used herein, the term "heterocyclyl" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1, 2 or 3 substituents selected from the groups consisting of the following:
(a) alkyl;
(b) hydroxy (or protected hydroxy);
(c) halo;
(d) haloalkyl;
(e) oxo, i.e., =O;
(f) amino, alkylamino or dialkylamino;
(g) alkoxy;
(h) cycloalkyl;
(i) carboxyl;
(j) heterocyclooxy, wherein heterocyclooxy denotes a heterocyclic group bonded through an oxygen bridge;
(k) alkyl-O—C(O)—;
(l) mercapto;
(m) nitro;
(n) cyano;
(o) sulfamoyl or sulfonamido;
(p) aryl;
(q) alkyl-C(O)—O—;
(r) aryl-C(O)—O—;
(s) aryl-S—;
(t) aryloxy;
(u) alkyl-S—;
(v) formyl, i.e., HC(O)—;
(w) carbamoyl;
(x) aryl-alkyl-; and
(y) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms, preferably 3-9, or 3-7 carbon atoms, each of which can be optionally substituted by one, or two, or three, or more substituents, such as alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamide, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryl" refers to an aromatic carbocyclic ring system containing 6 to 14 ring carbon atoms, which may be unsubstituted or substituted as defined.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, 7-benzofuranyl, 2-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

The trans arrangement of the 1,4-cyclohexyl substituents —NHC(O)R$^1$ and —CH$_2$NR$^4$R$^5$ is preferred.

Specific compounds of formula I which may be mentioned include:

trans-5-chloro-N-[4-(4-chloro-3,5-d6-dimethyl-pyrazol-1-ylmethyl)-cyclohexyl]-2-methyl-nicotinamide;
trans-5-chloro-N-[4-(3,5-diethyl-pyrazol-1-ylmethyl)-cyclohexyl]-2-methyl-nicotinamide;
trans-5-chloro-2-methyl-N-[4-(4,5,6,7-tetrahydro-indazol-1-ylmethyl)-cyclohexyl]-nicotinamide;
trans-5-chloro-2-methyl-N-[4-(4,5,6,7-tetrahydro-indazol-2-ylmethyl)-cyclohexyl]-nicotinamide;
trans-5-chloro-2-methyl-N-[4-(5-methyl-3-phenyl-pyrazol-1-ylmethyl)-cyclohexyl]-nicotinamide;
trans-5-chloro-N-[4-(4-chloro-5-methyl-3-trifluoromethyl-pyrazol-1-ylmethyl)-cyclohexyl]-2-methyl-nicotinamide;
trans-5-chloro-N-[4-(4-chloro-3-methyl-5-trifluoromethyl-pyrazol-1-ylmethyl)-cyclohexyl]-2-methyl-nicotinamide;
trans-2-chloro-N-{4-[3-(4-fluoro-phenyl)-5-methyl-pyrazol-1-ylmethyl]-cyclohexyl}-5-trifluoromethyl-benzamide;
trans-5-chloro-2-methyl-N-[4-(3,4,5-trimethyl-pyrazol-1-ylmethyl)-cyclohexyl]-nicotinamide;

trans-5-chloro-N-[4-(5-methoxy-3-methyl-pyrazol-1-ylmethyl)-cyclohexyl]-2-methyl-nicotinamide;
trans-2-chloro-N-[4-(4-chloro-3-methoxy-5-methyl-pyrazol-1-ylmethyl)-cyclohexyl]-5-trifluoromethyl-benzamide;
trans-5-chloro-N-[4-(3-methoxy-5-methyl-pyrazol-1-ylmethyl)-cyclohexyl]-2-methyl-nicotinamide;
trans-2-chloro-N-[4-(4-chloro-5-methoxy-3-methyl-pyrazol-1-ylmethyl)-cyclohexyl]-5-trifluoromethyl-benzamide;
trans-2-chloro-N-[4-(3,4-dimethyl-pyrazol-1-ylmethyl)-cyclohexyl]-5-trifluoro methyl-benzamide;
trans-2-chloro-N-[4-(4,5-dimethyl-pyrazol-1-ylmethyl)-cyclohexyl]-5-trifluoro methyl-benzamide;
trans-2-chloro-N-[4-(5,6-dihydro-4H-cyclopentapyrazol-1-ylmethyl)-cyclohexyl]-5-trifluoromethyl-benzamide;
trans-2-chloro-N-[4-(5,6-dihydro-4H-cyclopentapyrazol-2-ylmethyl)-cyclohexyl]-5-trifluoromethyl-benzamide;
trans-5-chloro-N-{4-[(5-ethyl-4-methyl-1H-pyrazol-3-ylamino)-methyl]-cyclohexyl}-2-methyl-nicotinamide;
trans-2-chloro-N-[4-(imidazo[1,2-a]pyridin-3-ylaminomethyl)-cyclohexyl]-5-trifluoro methyl-benzamide;
trans-4-{[4-(2-chloro-5-trifluoromethyl-benzoylamino)-cyclohexylmethyl]-amino}-benzoic acid;
trans-(4-{[4-(2-chloro-5-trifluoromethyl-benzoylamino)-cyclohexylmethyl]-amino}-phenyl)-acetic acid;
trans-5-chloro-2-methyl-N-{4-[(1H-pyrazolo[4,3-b]pyridin-3-ylamino)-methyl]-cyclohexyl}-nicotinamide;
trans-2-chloro-N-{4-[(5-methyl-4-pyridin-3-yl-2H-pyrazol-3-ylamino)-methyl]-cyclohexyl}-5-trifluoromethyl-benzamide;
trans-(3-{[4-(2-chloro-5-trifluoromethyl-benzoylamino)-cyclohexylmethyl]-amino}-phenyl)-acetic acid;
trans-5-chloro-N-{4-[(3-chloro-6-methoxy-pyridin-2-ylamino)-methyl]-cyclohexyl}-2-methyl-nicotinamide;
trans-2-chloro-N-(4-{[4-(2-chloro-4-methoxy-phenyl)-5-methyl-1H-pyrazol-3-ylamino]-methyl}-cyclohexyl)-5-trifluoromethyl-benzamide;
trans-2-(4-{[4-(2-chloro-5-trifluoromethyl-benzoylamino)-cyclohexylmethyl]-amino}-phenyl)-propionic acid;
trans-5-chloro-N-{4-[3-(4-fluoro-phenyl)-5-methyl-pyrazol-1-ylmethyl]-cyclohexyl}-2-methyl-nicotinamide;
trans-5-chloro-2-methyl-N-[4-(3-methyl-pyrazol-1-ylmethyl)-cyclohexyl]-nicotinamide;
trans-5-chloro-2-methyl-N-[4-(5-methyl-pyrazol-1-ylmethyl)-cyclohexyl]-nicotinamide;
trans-5-chloro-2-methyl-N-[4-(5-methyl-3-pyridin-3-yl-pyrazol-1-ylmethyl)-cyclohexyl]-nicotinamide;
trans-5-chloro-N-[4-(4-chloro-5-methoxy-3-methyl-pyrazol-1-ylmethyl)-cyclohexyl]-2-methyl-nicotinamide;
trans-5-chloro-N-[4-(4-chloro-3-methoxy-5-methyl-pyrazol-1-ylmethyl)-cyclohexyl]-2-methyl-nicotinamide;
trans-5-chloro-2-methyl-N-[4-(3-methyl-5,6-dihydro-4H-cyclopentapyrazol-2-ylmethyl)-cyclohexyl]-nicotinamide;
trans-5-chloro-2-methyl-N-[4-(3-methyl-5,6-dihydro-4H-cyclopentapyrazol-1-ylmethyl)-cyclohexyl]-nicotinamide;
trans-5-chloro-N-[4-(3,4-dimethyl-pyrazol-1-ylmethyl)-cyclohexyl]-2-methyl-nicotinamide;
trans-5-chloro-N-[4-(4,5-dimethyl-pyrazol-1-ylmethyl)-cyclohexyl]-2-methyl-nicotinamide;
trans-5-chloro-N-[4-(5,6-dihydro-4H-cyclopentapyrazol-1-ylmethyl)-cyclohexyl]-2-methyl-nicotinamide;
trans-5-chloro-N-[4-(5,6-dihydro-4H-cyclopentapyrazol-2-ylmethyl)-cyclohexyl]-2-methyl-nicotinamide;
trans-N-[4-(3-Benzo[1,3]dioxol-5-yl-5-methyl-pyrazol-1-ylmethyl)-cyclohexyl]-2-chloro-5-trifluoromethyl-benzamide;
trans-2-chloro-N-{4-[3-(4-methoxy-phenyl)-5-methyl-pyrazol-1-ylmethyl]-cyclohexyl}-5-trifluoromethyl-benzamide;
trans-5-chloro-N-[4-(3,5-d6-dimethyl-pyrazol-1-ylmethyl)-cyclohexyl]-2-methyl-nicotinamide;
trans-2-chloro-N-(4-pyrazolo[3,4-b]pyridin-2-ylmethyl-cyclohexyl)-5-trifluoro methyl-benzamide;
trans-2-chloro-N-(4-pyrazolo[3,4-b]pyridin-1-ylmethyl-cyclohexyl)-5-trifluoro methyl-benzamide;
trans-2-chloro-N-[4-[3,5-d]ethyl-pyrazol-1-ylmethyl)-cyclohexyl]-5-trifluoromethyl-benzamide;
trans-2-chloro-N-[4-(4-chloro-3,5-diethyl-pyrazol-1-ylmethyl)-cyclohexyl]-5-trifluoro methyl-benzamide;
trans-2-chloro-N-[4-(3-methyl-pyrazolo[3,4-b]pyridin-2-ylmethyl)-cyclohexyl]-5-trifluoromethyl-benzamide;
trans-2-chloro-N-[4-(3-methyl-pyrazolo[3,4-b]pyridin-1-ylmethyl)-cyclohexyl]-5-trifluoromethyl-benzamide;
trans-2-chloro-N-[4-(3-pyridin-4-yl-pyrazol-1-ylmethyl)-cyclohexyl]-5-trifluoro methyl-benzamide;
trans-2-chloro-N-[4-(3-methoxy-5-methyl-pyrazol-1-ylmethyl)-cyclohexyl]-5-trifluoromethyl-benzamide;
trans-2-chloro-N-[4-(3-methyl-5-phenyl-pyrazol-1-ylmethyl)-cyclohexyl]-5-trifluoro methyl-benzamide;
trans-2-chloro-N-[4-(5-methyl-3-phenyl-pyrazol-1-ylmethyl)-cyclohexyl]-5-trifluoro methyl-benzamide;
trans-2-chloro-N-[4-(5-methoxy-3-methyl-pyrazol-1-ylmethyl)-cyclohexyl]-5-trifluoromethyl-benzamide;
trans-2-chloro-N-[4-(5-methyl-3-trifluoromethyl-[1,2,4]triazol-1-ylmethyl)-cyclohexyl]-5-trifluoromethyl-benzamide;
trans-2-chloro-N-(4-purin-9-ylmethyl-cyclohexyl)-5-trifluoromethyl-benzamide
trans-2-chloro-N-[4-(3-methyl-5,6-dihydro-4H-cyclopentapyrazol-1-ylmethyl)-cyclohexyl]-5-trifluoromethyl-benzamide;
trans-2-chloro-N-[4-(3-methyl-5,6-dihydro-4H-cyclopentapyrazol-2-ylmethyl)-cyclohexyl]-5-trifluoromethyl-benzamide;
trans-2-chloro-N-[4-(4-chloro-3,5-d6-dimethyl-pyrazol-1-ylmethyl)-cyclohexyl]-5-trifluoromethyl-benzamide;
trans-2-chloro-N-[4-(4-methyl-pyrazol-1-ylmethyl)-cyclohexyl]-5-trifluoromethyl-benzamide;
trans-2-chloro-N-(4-pyrazol-1-ylmethyl-cyclohexyl)-5-trifluoromethyl-benzamide;
trans-2-chloro-N-[4-(4,5,6,7-tetrahydro-indazol-1-ylmethyl)-cyclohexyl]-5-trifluoro methyl-benzamide;
trans-2-chloro-N-[4-(4,5,6,7-tetrahydro-indazol-2-ylmethyl)-cyclohexyl]-5-trifluoro methyl-benzamide;
trans-2-chloro-N-[4-(4-chloro-3-hydroxymethyl-pyrazol-1-ylmethyl)-cyclohexyl]-5-trifluoromethyl-benzamide;
trans-4-chloro-1-[4-(2-chloro-5-trifluoromethyl-benzoylamino)-cyclohexylmethyl]-1H-pyrazole-3-carboxylic acid ethyl ester;
trans-1-[4-(2-chloro-5-trifluoromethyl-benzoylamino)-cyclohexylmethyl]-4-methyl-1H-pyrazole-3-carboxylic acid ethyl ester;
trans-4-chloro-2-[4-(2-chloro-5-trifluoromethyl-benzoylamino)-cyclohexylmethyl]-2H-pyrazole-3-carboxylic acid ethyl ester;
trans-2-[4-(2-chloro-5-trifluoromethyl-benzoylamino)-cyclohexylmethyl]-4-methyl-2H-pyrazole-3-carboxylic acid ethyl ester;
trans-2-chloro-N-[4-(5-ethyl-3-methyl-pyrazol-1-ylmethyl)-cyclohexyl]-5-trifluoro methyl-benzamide;

trans-2-chloro-N-[4-(3-ethyl-5-methyl-pyrazol-1-ylm-ethyl)-cyclohexyl]-5-trifluoro methyl-benzamide;
trans-2-chloro-N-[4-(4-chloro-5-ethyl-3-methyl-pyrazol-1-ylmethyl)-cyclohexyl]-5-trifluoromethyl-benzamide;
trans-2-chloro-N-[4-(4-chloro-3-ethyl-5-methyl-pyrazol-1-ylmethyl)-cyclohexyl]-5-trifluoromethyl-benzamide;
trans-2-chloro-N-[4-(4-chloro-5-hydroxymethyl-pyrazol-1-ylmethyl)-cyclohexyl]-5-trifluoromethyl-benzamide;
trans-1-[4-(2-chloro-5-trifluoromethyl-benzoylamino)-cyclohexylmethyl]-1H-pyrazole-3-carboxylic acid ethyl ester;
trans-2-[4-(2-chloro-5-trifluoromethyl-benzoylamino)-cyclohexylmethyl]-2H-pyrazole-3-carboxylic acid ethyl ester;
trans-N-[4-(3,5-bis-hydroxymethyl-pyrazol-1-ylmethyl)-cyclohexyl]-2-chloro-5-trifluoromethyl-benzamide;
trans-2-chloro-N-[4-(3-hydroxymethyl-5-isopropyl-pyrazol-1-ylmethyl)-cyclohexyl]-5-trifluoromethyl-benzamide;
trans-2-chloro-N-[4-(3,5-diisopropyl-pyrazol-1-ylmethyl)-cyclohexyl]-5-trifluoro methyl-benzamide;
trans-2-chloro-N-[4-(3-methyl-6,7-dihydro-4H-pyrano[4,3-c]pyrazol-1-ylmethyl)-cyclohexyl]-5-trifluoromethyl-benzamide;
trans-2-chloro-N-[4-(3-methyl-6,7-dihydro-4H-pyrano[4,3-c]pyrazol-2-ylmethyl)-cyclohexyl]-5-trifluoromethyl-benzamide;
trans-2-chloro-N-[4-(3-ethyl-4-methyl-pyrazol-1-ylm-ethyl)-cyclohexyl]-5-trifluoro methyl-benzamide;
trans-2-chloro-N-[4-(5-ethyl-4-methyl-pyrazol-1-ylm-ethyl)-cyclohexyl]-5-trifluoro methyl-benzamide;
trans-5-chloro-N-[4-(3-ethyl-4-methyl-pyrazol-1-ylm-ethyl)-cyclohexyl]-2-methyl-nicotinamide;
trans-5-chloro-N-[4-(5-ethyl-4-methyl-pyrazol-1-ylm-ethyl)-cyclohexyl]-2-methyl-nicotinamide;
trans-2-chloro-N-[4-(5-isopropyl-4-methyl-pyrazol-1-ylm-ethyl)-cyclohexyl]-5-trifluoro methyl-benzamide;
trans-2-chloro-N-[4-(3-isopropyl-4-methyl-pyrazol-1-ylm-ethyl)-cyclohexyl]-5-trifluoromethyl-benzamide;
trans-5-chloro-N-[4-(3-isopropyl-4-methyl-pyrazol-1-ylm-ethyl)-cyclohexyl]-2-methyl-nicotinamide;
trans-N-[4-(3-tert-Butyl-pyrazol-1-ylmethyl)-cyclohexyl]-2-chloro-5-trifluoromethyl-benzamide;
trans-2-chloro-N-[4-(2-chloro-pyrrolo[2,3-d]pyrimidin-7-ylmethyl)-cyclohexyl]-5-trifluoromethyl-benzamide;
trans-5-chloro-N-[4-(2-chloro-pyrrolo[2,3-d]pyrimidin-7-ylmethyl)-cyclohexyl]-2-methyl-nicotinamide;
trans-5-chloro-N-[4-(3-hydroxymethyl-5-methyl-pyrazol-1-ylmethyl)-cyclohexyl]-2-methyl-nicotinamide;
trans-5-chloro-N-[4-(5-hydroxymethyl-3-methyl-pyrazol-1-ylmethyl)-cyclohexyl]-2-methyl-nicotinamide;
trans-5-chloro-N-[4-(5-isopropyl-3-methyl-pyrazol-1-ylm-ethyl)-cyclohexyl]-2-methyl-nicotinamide;
trans-5-chloro-N-[4-(3-isopropyl-5-methyl-pyrazol-1-ylm-ethyl)-cyclohexyl]-2-methyl-nicotinamide;
trans-N-[4-(3,5-Dimethyl-pyrazol-1-ylmethyl)-cyclohexyl]-2-methyl-5-trifluoro methyl-nicotinamide; and
trans-5-chloro-N-[4-(4-deutero-3,5-dimethyl-pyrazol-1-yl-methyl)-cyclohexyl]-2-methyl-nicotinamide;
and isomers thereof;
in free or in salt form.

Therefore, according to a further aspect of the invention we provide a compound of formula I as hereinbefore described as a medicament. More particularly, we provide a compound of formula I as hereinbefore described as a corticotropin releasing factor (CRF) receptor antagonist.

According to a further aspect of the invention we provide the use of a compound of formula I as hereinbefore described in the manufacture of a medicament. More particularly, we provide the use as hereinbefore described in the manufacture of a medicament for a corticotropin releasing factor (CRF) receptor antagonist.

Furthermore it has now been found that the compounds of formula I, or a salt thereof, behave as CRF receptor antagonists. Representative compounds of the invention have no significant agonist or antagonist activity at melanin concentrating hormone receptor 1 (MCH-1) or MCH-2.

Certain compounds of formula I show antagonistic activity at both the corticotropin releasing factor receptor 1 (CRF-1) and 2 (CRF-2) and are thus dual CRF-1 and CRF-2 antagonists.

The activity of a compound according to the present invention can be assessed by the following in vitro & in vivo methods.

The CRF-1 and CRF-2 receptor antagonistic activity of the agents of the invention has been determined in vitro in the following assay:

Chinese hamster ovary (CHO) cells expressing either the human or rat recombinant CRF-1 or human CRF-2α (Chen et al, Proc Natl Acad Sci USA 90, 8967-8971, 1993; Liaw et al, Endocrinology 137, 72-77, 1996) are propagated in Dulbecco's modified Eagle medium supplemented with 10% foetal calf serum, non-essential amino acids, 100 U/ml penicillin, 100 mg/l streptomycin and 1 g/l geneticin. CHO cells expressing the rat CRF-2β receptor (Wu et al, Endocrinology 148, 1675-1687, 2007) are propagated in HAM's-F12 Glutamax supplemented with 10% foetal calf serum, 100 IU/ml penicillin, 100 mg/l streptomycin, 600 µg/ml hygromycin, 10 µg/ml blasticidin and induced with 1 µg/ml of tetracyclin for 24 hours prior to experimentation. For cyclic AMP determinations the Homogeneous Time-Resolved Fluoresce (HTRF) CAMP dynamic 2 kit (Cisbio International, France) was used as per manufacturers' instructions. CHO cells, previously cryopreserved at $3 \times 10^6$ viable cells per ml of cell recovery media (Cat no. 12648-010, Invitrogen), were thawed, centrifuged for 7 mins at 1200 rpm and resuspended in serum free media to give a concentration of $0.5 \times 10^6$ cells per/ml. Compounds of the invention, prepared in DMSO, and subsequently diluted 50 fold in assay buffer (1× Hanks balanced salt solution, 0.2% (w/v) bovine serum albumin, 1.7 mM isobutylmethylxanthine and 10 mM Hepes, pH7.4) were then added onto the 384 well low volume black assay plate (Corning Inc, US, Cat. 3676). 2000 cells/well were then added to the assay plate further diluting the compound 2 fold and then the plate was incubated for 15 mins at room temperature. Following incubation, buffer containing a 5 times final concentration of agonist, typically r/h CRF is added to the plate and incubated for 30 min at room temperature. Finally, d2 dye labeled cAMP and cryptate labeled anti-cAMP antibody, both made in lysis buffer, are added to the plate followed by a settling period of 1 hour at room temperature. During the settling period cAMP produced by the cells competes with the d2 labelled cAMP for the anti-cAMP cryptate. The plate is read on the Pherastar (BMG, Germany). Increasing levels of endogenous cAMP produced by cells can be followed by a decrease of FRET fluorescent signal and vice versa. Values represented by a change in arbitrary fluorescence units are converted into cAMP concentrations by use of a standard curve, the reagents for which are supplied with the kit. Antagonist dose response curves (1 nM-31.6 µM) are constructed and tested in the presence of an $EC_{50}$ concentration of CRF relevant to the receptor (hCRF-1=3 nM, hCRF-2α=2 nM, rCRF-1=1 nM and rCRF-2β=0.1 nM). $IC_{50}$ values of antagonists are calculated by fitting the percent inhibition of CRF induced cAMP response by increasing concentrations of the antagonists. The fit is performed using the nonlinear logistic function of the Activitybase software package v 5.4.5.27 (IDBS, UK).

In this test, the agents of the invention show CRF, antagonistic activity with IC50 CRF, values of about 1 nM to 10 μM, preferably about 1 to 500 nM. Specific data are provided in the Table of Biological Data herein.

Compounds of the invention are useful for the treatment of any state with increased endogenous levels of CRF (corticotropin releasing factor) or in which the HPA (hypothalamic pituitary axis) is disregulated, or of various diseases induced or facilitated by CRF.

Compounds of the invention are in particular useful for the treatment or prevention of gastrointestinal disorders including irritable bowel syndrome with or without diarrhoea, inflammatory bowel diseases, post-operative ileus, reflux disease and infectious diarrhoea.

Compounds of the invention are also in particular useful for the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multiinfarct dementia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, lemporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dysomnia, insomnia, sleep apnoea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful in the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The utility of the agents of the invention in the above indicated diseases can be confirmed in a range of standard tests. (1) The anxiolytic activity of the agents of the invention can be confirmed in the mouse elevated plus-maze [see for example Rodgers R. J., Behavioural Pharmacology 8: 477-496 (1997) where the relevance of the elevated plus-maze is discussed on p. 486; for the method, see Rodgers R. J. et al. Ethology and Psychopharmacology (Eds S J Cooper and C A Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example Maillot C., Gastroenterology 119:1569-1579 (2002)].

In these tests, the agents of the invention show anxiolytic-like, visceral analgesic and anti-diarrheal effects following oral administration of 0.1 to 30 mg/kg.

Furthermore, it has surprisingly been found that CRF induced intestinal barrier dysfunction in vivo can be successfully reversed using a dual CRF receptor 1 and 2 antagonist.

Hence, in a further aspect, there is provided a dual corticotropin releasing factor receptor 1 (CRF-1) and 2 (CRF-2) antagonist for use in the treatment, alleviation or prophylaxis of a condition characterized by a barrier dysfunction of mucous epithelia, epidermis or endothelia.

In another aspect, there is provided a method of treatment, alleviation or prophylaxis of a condition characterized by a barrier dysfunction of mucous epithelia, epidermis or endothelia which comprises administering to a mammal a therapeutically effective amount of a dual corticotropin releasing factor receptor 1 (CRF-1) and 2 (CRF-2) antagonist.

According to another aspect, there is provided the use of a dual corticotropin releasing factor receptor 1 (CRF-1) and 2 (CRF-2) antagonist in the manufacture of a medicament for the treatment, alleviation or prophylaxis of a condition characterized by a barrier dysfunction of mucous epithelia, epidermis or endothelia.

In one embodiment, the condition is characterized by a barrier dysfunction of mucous epithelia.

In one particular embodiment, the condition is characterized by a barrier dysfunction of gastrointestinal mucous epithelia. Barrier dysfunctions of gastrointestinal mucous epithelia may be induced by radiation therapy and by drugs such as non-steroidal anti-inflammatory drugs, cancer chemotherapeutic agents, cytotoxic antibiotics, anti-metabolites, vinca alkaloids and others such as cisplatin, dacarbazine, procarbazine and hydroxyurea and combinations thereof. Barrier dysfunctions of gastrointestinal mucous epithelia may also be induced by malnutrition, total parenteral nutrition, food allergens or toxins such as toxins caused by metabolic disorders or liver diseases or by infection or released during bacterial or viral infection. More particularly, conditions characterized by a barrier dysfunction of gastrointestinal mucous epithelia for which dual corticotropin releasing factor receptor 1 (CRF-1) and 2 (CRF-2) antagonists may be useful include but are not limited to inflammatory bowel disease, irritable bowel syndrome with or without diarrhea, short bowel syndrome, chronic enteropathy such as celiac disease, postoperative ileus, cystic fibrosis, reflux disease, heartburn, infectious diarrhea, intestinal neoplasms, intestinal adenocarcinomas, diabetes, sepsis, chronic heart failure and AIDS.

In one particular embodiment, the condition is characterized by a barrier dysfunction of respiratory mucous epithelia. Barrier dysfunctions of respiratory mucous epithelia may be induced by allergens, or toxins such as toxins caused by infection or released during bacterial or viral infection. More particularly, conditions characterized by a barrier dysfunction of respiratory mucous epithelia for which dual corticotropin releasing factor receptor 1 (CRF-1) and 2 (CRF-2) antagonists may be useful include but are not limited to asthma, chronic bronchitis, rhinitis, rhinosinusitis, chronic obstructive pulmonary disease, cystic fibrosis, pneumonia, sepsis, chronic heart failure and AIDS.

In one embodiment, the condition is characterized by a barrier dysfunction of the epidermis. Barrier dysfunctions of epidermis may be induced by allergens, or toxins such as toxins caused by infection or released during bacterial or viral infection. More particularly, conditions characterized by a barrier dysfunction of epidermis for which dual corticotropin releasing factor receptor 1 (CRF-1) and 2 (CRF-2) antagonists may be useful include but are not limited to dermatitis, ichthyosis, and psoriasis.

In one embodiment, the condition is characterized by a barrier dysfunction of endothelia. Barrier dysfunctions of endothelia may be induced by allergens or toxins such as toxins caused by metabolic disorders or liver diseases or by infection or released during bacterial or viral infection. More particularly, conditions characterized by a barrier dysfunction of endothelia for which dual corticotropin releasing factor receptor 1 (CRF-1) and 2 (CRF-2) antagonists may be useful include but are not limited to ischemic injury, hypoxia, diabetes, sepsis, chronic heart failure, edema, acute lung injury, acute respiratory distress syndrome, thrombosis and cancer.

In one particular embodiment, the condition is characterized by a barrier dysfunction of the brain-blood barrier. More particularly, conditions characterized by a barrier dysfunction of the brain-blood barrier for which dual corticotropin releasing factor receptor 1 (CRF-1) and 2 (CRF-2) antagonists may be useful include but are not limited to ischemic stroke, migraine, multiple sclerosis, Alzheimer's disease, epilepsy, cancer brain metastases and encephalopathy.

Conditions characterized by a barrier dysfunction of mucous epithelia, epidermis or endothelia for which dual corticotropin releasing factor receptor 1 (CRF-1) and 2 (CRF-2) antagonists may be useful include but are not limited to inflammatory bowel disease, irritable bowel syndrome, short bowel syndrome, postoperative ileus, allergy, dermatitis, sepsis, ischemic injury, multiple sclerosis and encephalopathy (Elias and Schmuth, Curr Opin Allergy Clin Immunol 9, 437-446, 2009; Lindsberg at al., J Cerebral Blood Flow & Metabolism 30, 689-702. 2010; Marchiando at al., Annu Rev Pathol Mech Dis 5, 119-144, 2010; Öhman and Simrén, Nat Rev Gastroenterol Hepatol 7, 163-173, 2010).

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg, preferably from about 1 to about 30 mg/kg animal body weight. In larger mammals, for example humans, an indicated daily dosage is in the range from about 1 to about 500 mg, preferably from about 1 to about 100 mg of an agent of the invention, conveniently administered, for example, in divided doses up to three times a day or in sustained release form.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of diseases induced or facilitated by CRF, such as these indicated above.

Therefore, according to a further aspect of the invention we provide a compound of formula I, or a salt thereof, for the treatment or alleviation of treatment of any state with increased endogenous level of CRF or in which the HPA (hypothalamic pituitary axis) is disregulated, or of various diseases induced or facilitated by CRF.

The agents of the invention can be administered in vivo either alone or in combination with other pharmaceutical agents, e.g. agents effective in the treatment of diseases and conditions in which an increased endogenous level of CRF plays a role or is implicated. A suitable combination consists of a compound of the present invention with one or more compounds selected from the group consisting of dopamine D2 receptor antagonists, serotonin 5-HT4 receptor agonists, serotonin 5-HT3 receptor agonists, serotonin 5-HT3 receptor antagonists, CCK1 receptor antagonists, motilin receptor agonists, μ-opioid receptor antagonists, opioid receptor agonists and opiates, other CRF receptor antagonists, glutamate receptor antagonists, neurokinin receptor antagonists, histamine H2 receptor antagonists, histamine H4 receptor antagonists, proton pump inhibitors, chloride channel activators, guanylate cyclase-c activators, muscarinic receptor antagonists, antispasmodics, stimulant laxatives, osmotic laxatives, faecal softeners, absorbents and fibre supplements, antacids, GI relaxants, bismuth compounds, vanilloid receptor antagonists, anticonvulsants, NSAIDS, COX-2 inhibitors, GABAb receptor modulators, CB receptor ligands, calcium channel blockers, sodium channel blockers, tricyclic antidepressants, serotonin and noradrenaline re-uptake inhibitors, benzodiazepines, alpha-2 receptor agonists and ghrelin receptor agonists.

More specifically, a compound of the present invention may be administered as a combination with one or more compounds selected from the group consisting of dopamine D2 receptor antagonists, such as, chlorpromazine, prochlorperazine, haloperidol, alizapride, domperidone, metoclopramide and itopride; serotonin 5-HT4 receptor agonists, such as, cisapride, cinitapride, mosapride, renzapride, prucalopride, tegaserod, velusetrag, ATI-7505 and compounds described in WO 2005068461, US 2005228014, WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857, WO 2006108127, US 20060183901, WO 2006127815, US 20060276482, WO 2007005951, WO 2007010390, WO 2007005951, WO 2007048643, WO 2007096352, WO 2007068739 and WO 20070117796; serotonin 5-HT3 receptor agonists, such as, pumesotrag and compounds described in WO 2007004041; serotonin 5-HT3 receptor antagonists, such as, alosetron, cilansetron, ramosetron, azasetron, ondansetron, granisetron, tropisetron, DDP225 and compounds described in WO 2006183769, WO 2006105117 and WO 2007004041; CCK1 receptor antagonists, such as, JNJ-17156516, devazepide, loxiglumide and dexloxigiumide; motilin receptor agonists, such as, motilin, atilmotin, erythromycin, alemcinal, mitemcinal, KOS-2187, 1-[4-(3-fluoro-phenylamino)-piperidin-1-yl]-2-[4-((S)-3-methyl-piperazin-1-ylmethyl)-phenyl]-ethanone and compounds described in WO 2005060693, WO 2006127252, WO 2007007018, WO 2007012479 and WO 2008000729; m-opioid receptor antagonists, such as, naxolone, alvimopan, methylnaltrexone and compounds described in US 20050203123, US 2006063792, WO 2007050802, US 2007103187, WO 2009029252, WO 2009029256, WO 2009029257 and WO 2009029253; opioid receptor agonists and opiates, such as, morphine, buprenorphine, diamorphine, dihydrocodeine, fentanyl, pethidine, asimadoline, loperamide and codeine; CRF receptor antagonists, such as, GSK876008, pexacerfont and compounds described in WO 2004069257, WO 9940089, U.S. Pat. No. 6,844,351, WO 2005013997, WO 2005014557, WO 2005023806, WO 2005026126, WO 2005028480, WO 005044793, WO 2005051954, WO 2005051954, WO 2005115399, WO 2005028480, WO 2005023806, WO 2006044958, WO 2006044821 and US 20060211710; glutamate receptor antagonists, such as, AZD9272, AZD2066, AFQ056, ADX-48621 and compounds described in WO 9902497, WO 2000020001, WO 200304758 and WO 2005030723, WO 2005077345, US 2006009443, EP 1716152, WO 2005080397, US 2006019997, WO 2005066155, WO 2005082884, WO 2005044266, WO 2005077373, EP 1713791, EP 1720860, WO 2005080379, EP 1716130, US 2006235024, WO 2005080363 WO 2006114264, WO 2006114260, WO 2006089700, WO 2006114262, WO 2006123257, US 2005272779, WO 2006048771, WO 2006123249, US 2006009477, WO 2006014185, EP 1723144, US 2006025414, US 2006004021, US 2006160857, WO 2006074884, WO 2006129199, WO 2006123244, WO 2006123255, WO 2007040982, WO 2007023290, WO 2007023242, WO 2007050050, WO 2007039781, WO 2007039782 and WO 2007023245; neurokinin receptor antagonists, such as, taletant, osanetant, casopitant, nepadutrent, saredutant, DNK-333, SLV-317, SLV321, SLV317 and compounds described in EP 96-810237, WO 2006137790, WO 2006137791, WO 2006094934, WO 2007037742 and WO 2007037743; histamine H2 receptor antagonists, such as, famotidine, cimetidine, ranitidine and nizatidine; histamine H4 receptor antagonists, such as, JNJ7777120, JNJ10191584 and compounds described in US 2006111416, WO 2006050965, WO 2005092066, WO 2005054239 US 2005070550, US 2005070527, EP 1505064, WO 2007090852, WO 2007090853, WO 2007090854, US 20070232616, US 20070238771, WO 2007117399, WO 2007031529 and WO2007072163; proton pump inhibitors, such as, omeprazole, lansoprazole, rabeprazole, tentoprazole, pantoprazole, esomeprazole, revaprazan, soraprazan and AGN201904; chloride channel activators, such as, lubiprostone; guanylate cyclase-2c activators, such as, linaclotide, guanilib, guanylin, uroguanylin and compounds described in WO 2005087797, WO 2005016244, WO 2007022531, WO 2007101158, WO 2007101161 and U.S. Pat. No. 7,041,786; muscarinic receptor antagonists, such as, darifenacin, solifenacin, atropine, dicycloverine, hycosine butyl bromide, propantheline, oxybutinin, cimetropium bromide and pinaverium bromide; antispasmodics, such as, mebeverine, octylonium bromide, trimebutine, tiropramide, alverine and peppermint oil; stimulant laxatives, such as, bisacodyl; osmotic laxatives, such as, activated charcoal with sorbitol, lactulose, magnesium hydroxide and phosphate buffered saline; faecal softeners, such as, senna concentrate, liquid paraffin and arachis oil; absorbents and fibre supplements; bulk fibre laxatives such as bran, methylcellulose, ispaghula husk and sterculia; antacids, such as, aluminium, magnesium and calcium antacids, simeticone and alginate containing preparations; GI relaxants, such as, cholestyramine resin; bismuth compounds, such as, bismuth subsalicylate; vanilloid receptor antagonists, such as, SB-705498, ABT-102, AZD1386, GRC-6211, MK-2295 and compounds described in WO 2002076946, WO 2004033435, WO 2005121116, WO 2005120510, WO 2006006740, WO 2006006741, WO 2006010445, WO 2006016218, US 2006058308, WO 2006033620, WO 2006038871, US 2006084640, US 2006089360, WO 2006058338, WO 2006063178, US 2006128689, WO 2006062981, WO 2006065646, WO 2006068618, WO 2006068592, WO 2006068593, WO 2006076646, US 2006160872, WO 200608082, US 2006183745, WO 2006095263, WO 2006102645, WO 2006100520, US 2006241296, WO 2006122200, WO 2006120481, WO 2006122250, DE 102005044814, WO 2006122772, WO 2006122777, WO 2006124753, WO 2006122799, WO 2006122770, WO 2006122769, WO 2006136245, WO 2007030761, US 20070088072, US 20070088073, US 20070105920, WO 2007042906, WO 2007045462, WO 2007050732; anticonvulsants, such as, carbemazepine, oxcarbemazepine, lamotrigine, gabapentin and pregabalin; NSAIDS, such as, aspirin, acetometaphen, ibuprofen, diclofenac, naproxen, flurbiprofen, indomethacin, piroxicam, ketoprofen, sulindac and diflunisal; COX-2 inhibitors, such as, celecoxib, rofecoxib, lumiracoxib, valdecoxib, etoricoxib and compounds described in WO 2004048314; GABAb receptor modulators, such as, racemic and (R)-baclofen, AZD3355, XP19986 and compounds described in WO 2006001750 and WO 2004000856; CB receptor ligands, such as, dronabinol, nabilone, cannabidiol, rimonabant and compounds described in WO 2002042248 and WO 2003066603; calcium channel blockers, such as, ziconotide, AGIO-003, PD-217014 and compounds described in WO 2006038594, WO 2006030211 and WO 2005058448; sodium channel blockers, such as, lamotrigine and compounds described in WO 2006023757, WO 2005097136, JP 2005206590 and WO 2005047270; tricyclic antidepressants, such as, clomipramine, amoxapine, nortripyline, amitriptyline, imipramine, desipramine, doxepin, trimipramine and protripyline; serotonin and noradrenaline re-uptake inhibitors, such as, milnaciprin, desvenlafaxine, sibutramine, duloxetine, fluoxetine, paroxetine, citalopram, sertraline and fluvoxamine; benzodiazepines, such as, levotofisopam, diazepam, lorazepam, clonazepam and alprazolam; alpha-2 receptor agonists, such as, clonidine, tizanidine and guanfacine; ghrelin receptor agonists, such as, ghrelin, ibutamoren, capromorelin, tabimorelin, ipamorelin, 2-Methylalanyl-N-[1(R)-formamido-2-(1H-indol-3-yl)ethyl]-D-tryptophanamide, TZP-101, TZP-102, LY-444711, EX-1314 and compounds described in U.S. Pat. No. 6,525,203, US 20050154043, WO 2005097788, WO2006036932, WO 2006135860, US 20060079562, WO 2006010629, WO 2006009674, WO 2006009645, US 20070021331, WO 2007020013, US 20070037857, WO 2007014258, WO 2007113202, WO 2007118852, US 20080194672, US 20080051383 and US 20080051383; corticosteroids, such as, hydrocortisone, cortisone, dexamethasone, betamethasone, beclomethasone, prednisolone, 6-methylprednisolone, budesonide, mometasone furoate, ciclesonide, fluticasone propionate and fluticasone furoate; aminosalicylates, such as, mesalazine, ipsalazide, olsalazine and balsalazide; immunomodulators, such as, azathioprine, 6-mercaptopurine, methotrexate, mycophenolate mofetil, ciclosporin and tacrolimus; PDE4 inhibitors, such as, tetomilast, cilomilast, roflumilast and arofylline; antibiotics, such as, metronidazole, ornidazole and ciprofloxacin; anti-adhesion molecule agents, such as, natalizumab and MLN02; anti IL-2 agents, such as, daclizumab and basilixumab; anti CD-3 agents, such as, visilizumab; and anti-TNF agents, such as, infliximab, adalimumab, fontolizumab and certolizumab pegol; psychiatric medications comprising compounds selected from the group consisting of agomelatine, azapirones, alprazolam, amitriptyline, aniracetam, acetyl-L-carnitine, aripiprazol, acetophenazine, benzodiazepines, barbiturate, buspirone, bupropione, chlordiazepoxide, chlorazepate, clonazepam, chlorpromazine, clozapine, CX614, CX516, chlorprothixene, diphenhydramine hydroxyzine, demoxepam, diazepam, droperidol, duloxetine, donezepil, doxepine, desipramine, flurazepam, fluphenazine, fluoxetine, flupentixol, gabapentin, melatonin, ginkgo-derived compounds, galantamine, haloperidol, Hydergine (ergoioid mesylates), huperzine, isocarboxazid, imipramine, lorazepam, loxapine, meprobamate, medazepam, moclobemide, molindone, maprotiline, modafinil, memantine, methylphenicate, mesoridazine, methotrimeprazine, nortriptyline, naproxen, oxazepam, oxiracetam, olanzapine, prazepam, paroxetine, phenelzine, pipotiazine, perphenazine, promazine, pimozide, PDE4 inhibitors, quazepam, quetiapine, reboxetine, rivastigmine, prochlorperazine, risperidone, sertraline, sertindole, temazepam, triazolam, tranylcypromine, tomoxetine, thiotixene, trifluoperazine, thioridazine, zolpidem and ziprasidone.

A group of compounds which may be mentioned are compounds of formula VI;

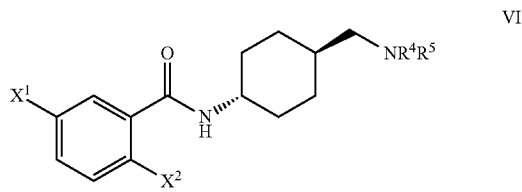

in which $R^4$, $R^5$, $X^1$ and $X^2$ are each as hereinbefore described;
and isomers thereof;
in free form or in salt form.

An alternative group of compounds which may be mentioned are compounds of formula VII;

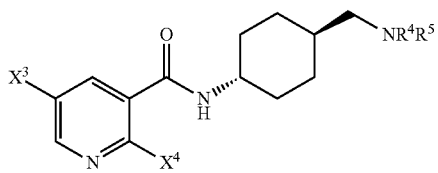

in which $R^4$, $R^5$, $X^3$ and $X^4$ are each as hereinbefore described;
and isomers thereof;
in free form or in salt form.

An alternative group of compounds which may be mentioned are compounds of formula VIII;

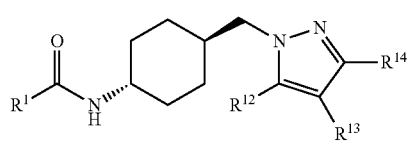

in which $R^1$, $R^{12}$, $R^{13}$ and $R^{14}$ are each as hereinbefore described;
and isomers thereof;
in free form or in salt form.

An alternative group of compounds which may be mentioned are compounds of formula IX or X;

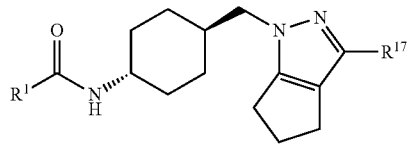

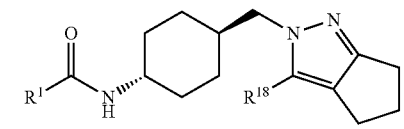

in which $R^1$, $R^{17}$ and $R^{18}$ are each as hereinbefore described;
and isomers thereof;
in free form or in salt form.

An alternative group of compounds which may be mentioned are compounds of formula XI;

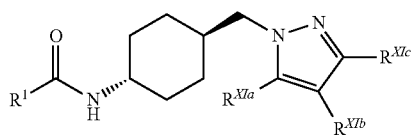

in which $R^1$ is as hereinbefore described;
$R^{XIa}$ is hydrogen, alkyl C1 to 6, alkoxy C1 to 6, hydroxyalkyl C1 to 6, —$CO_2R^{11}$ or phenyl optionally substituted by fluoro;
$R^{11}$ is alkyl C1 to 6;
$R^{XIb}$ is hydrogen, deuterium, alkyl C1 to 6 or chloro;
$R^{XIc}$ is hydrogen, alkyl C1 to 6, methoxy, hydroxyalkyl C1 to 6, ethoxycarbanyl, pyridyl, benzo[1,3]dioxo-5-yl or phenyl, optionally substituted by fluoro, alkoxy C1 to 6;
provided that at least one of $R^{XIa}$, $R^{XIb}$ and $R^{XIc}$ comprises one or more deuterium moieties;
and isomers thereof;
in free form or in salt form.

Acid addition salts may be produced from the free bases in known manner, and vice-versa. A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids) one or more protonated basic groups (e.g. amines), or both (e.g. zwitterions).

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

A prodrug is a compound which is converted to a therapeutically active compound after administration. For example, conversion may occur by hydrolysis of an ester group or some other biologically labile group. Prodrug preparation is well known in the art. For example "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon, sulfur or phosphorus atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formula (I) in optically pure form, where appropriate, can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallisation, chromatography, solvent distribution and similar procedures. This separation may take place either at the level of a starting compound or in a compound of formula (I) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

According to a further aspect of the invention we provide a method of treatment or alleviation of any state with increased endogenous level of CRF or in which the HPA (hypothalamic pituitary axis) is disregulated, or of various diseases induced or facilitated by CRF which comprises administering to a mammal a therapeutically effective amount of a compound of formula I as hereinbefore described, or a salt thereof.

We further provide a pharmaceutical composition comprising a compound of formula I as hereinbefore described, in free form or in pharmaceutically acceptable salt form, in association with a pharmaceutically acceptable adjuvant, diluent or carrier.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e.g., from about 0.1% to about 99.9%, preferably from about 20% to about 60%, of the active ingredients. Pharmaceutical preparations for the combination therapy for enteral or parenteral administration are, e.g., those in unit dosage form, such as tablets including sugar-coated tablets, capsules, suppositories and ampoules. These are prepared in a manner known, per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CRF, or (ii) associated with CRF activity, or (iii) characterized by abnormal activity of CRF; or (2) reducing or inhibiting the activity of CRF; or (3) reducing or inhibiting the expression of CRF. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CRF; or at least partially reducing or inhibiting the expression of CRF. The meaning of the term "a therapeutically effective amount" as illustrated in the above embodiment for CRF also applies by the same means to any other relevant proteins/peptides/enzymes.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the α-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances and deuterium analogues are included within the scope of the compounds of the present invention.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula with the co-crystal former under crystallization conditions and isolating co-crystals thereby formed. Suitable co-crystal formers include those described in WO 2004/078163. Hence the invention further provides co-crystals comprising a compound of formula I.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

Other process schemes which may be utilised include:
(it should be noted that the numbered R groups referred to in the reaction sequences below are for illustrative purposes only and do not precisely correspond to the R groups hereinbefore defined):

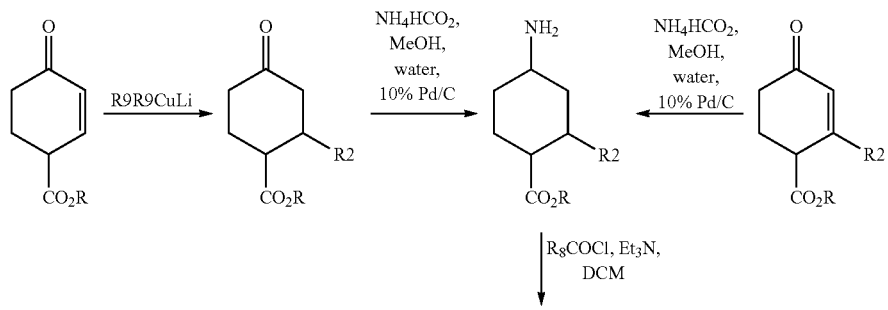

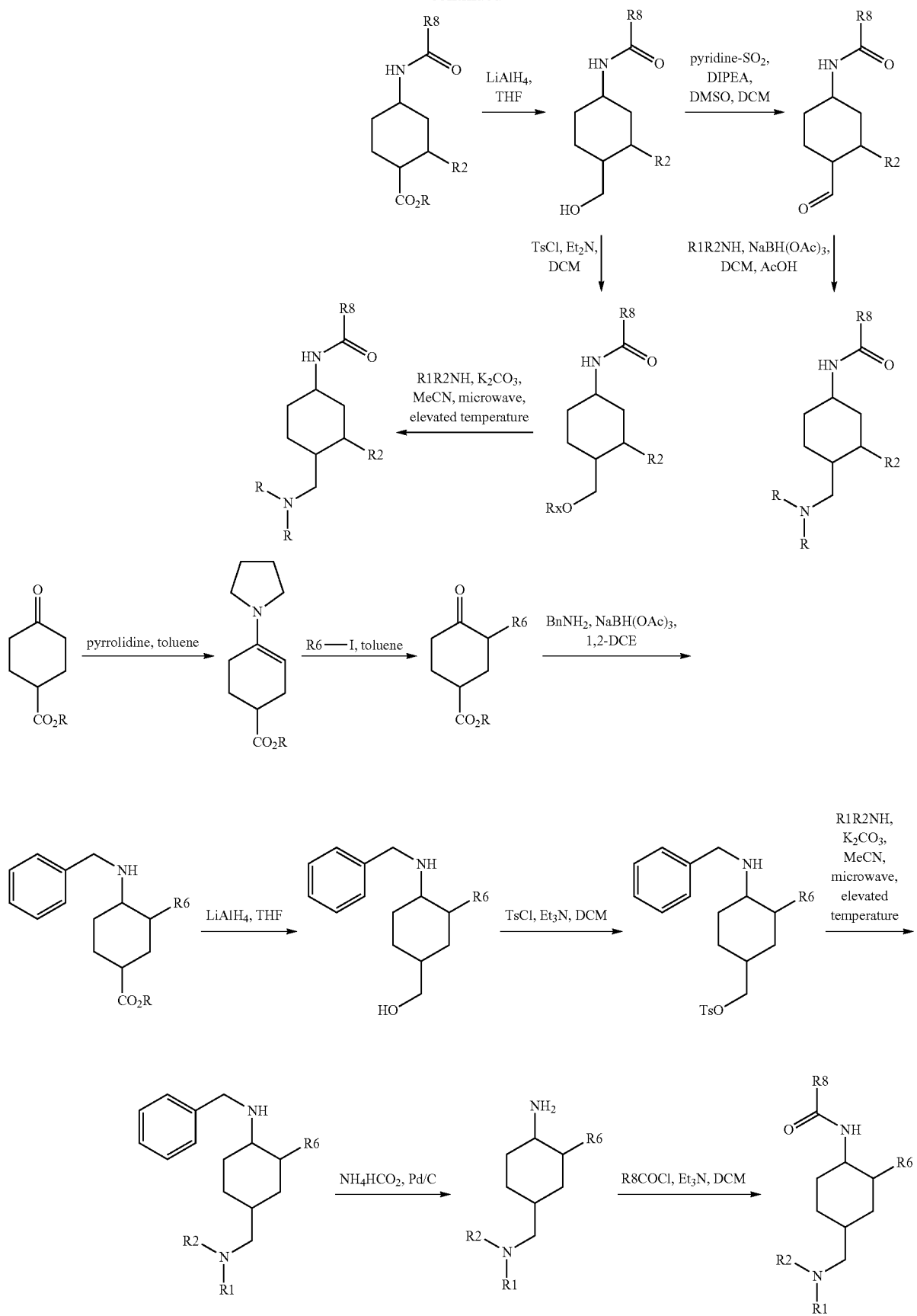

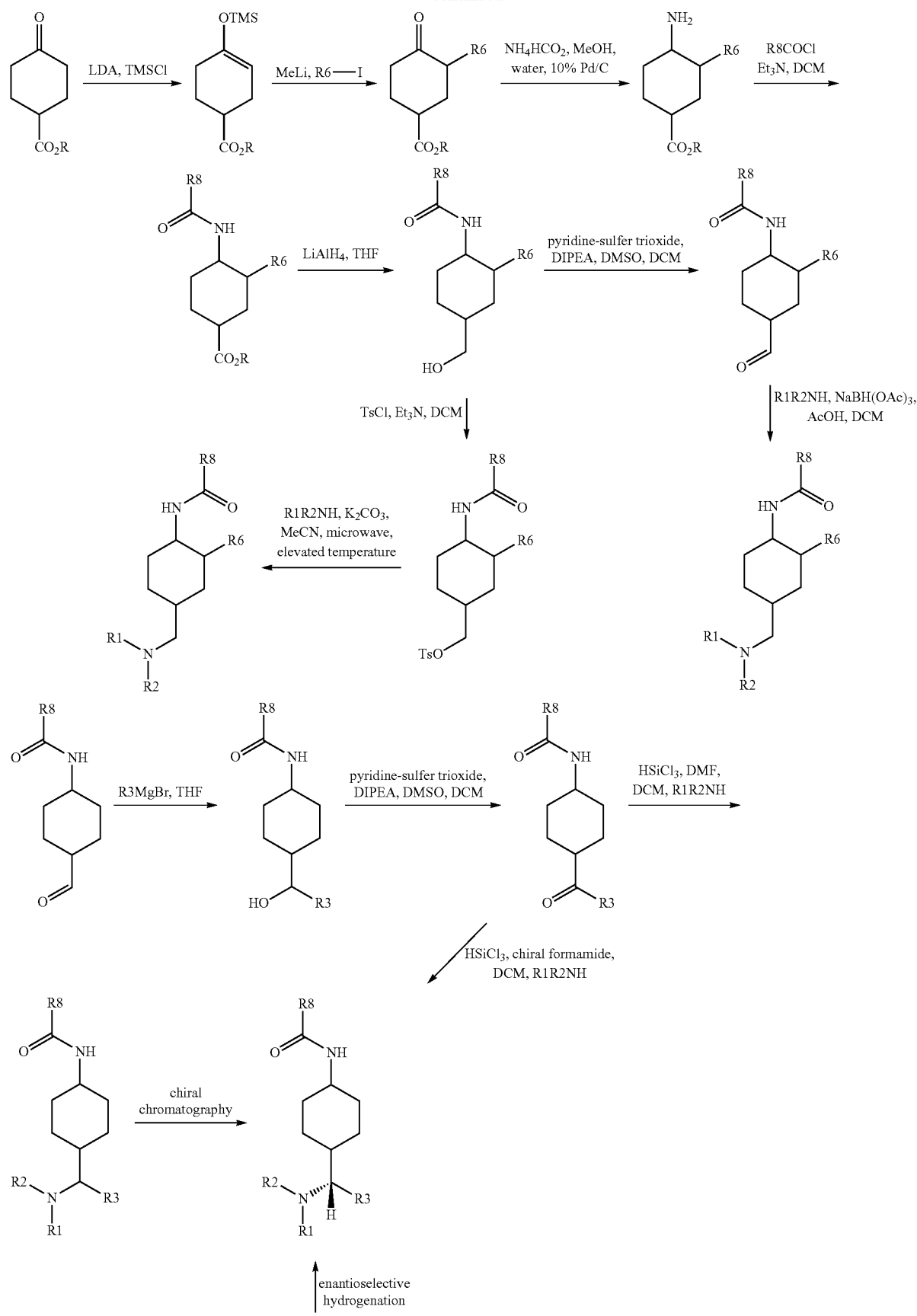

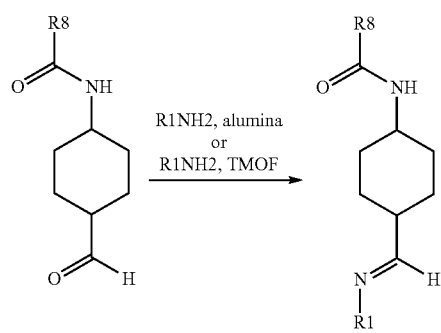

The leaving group R[y] may be any conventionally known leaving group, examples of which include, -Ts (tosylate), -Tf (triflate) or Ms (mesylate).

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/l, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Compounds of formula I may be prepared by the general reactions (it should be noted that the numbered R groups referred to in the reaction sequences below are for illustrative purposes only and do not precisely correspond to the R groups hereinbefore defined):

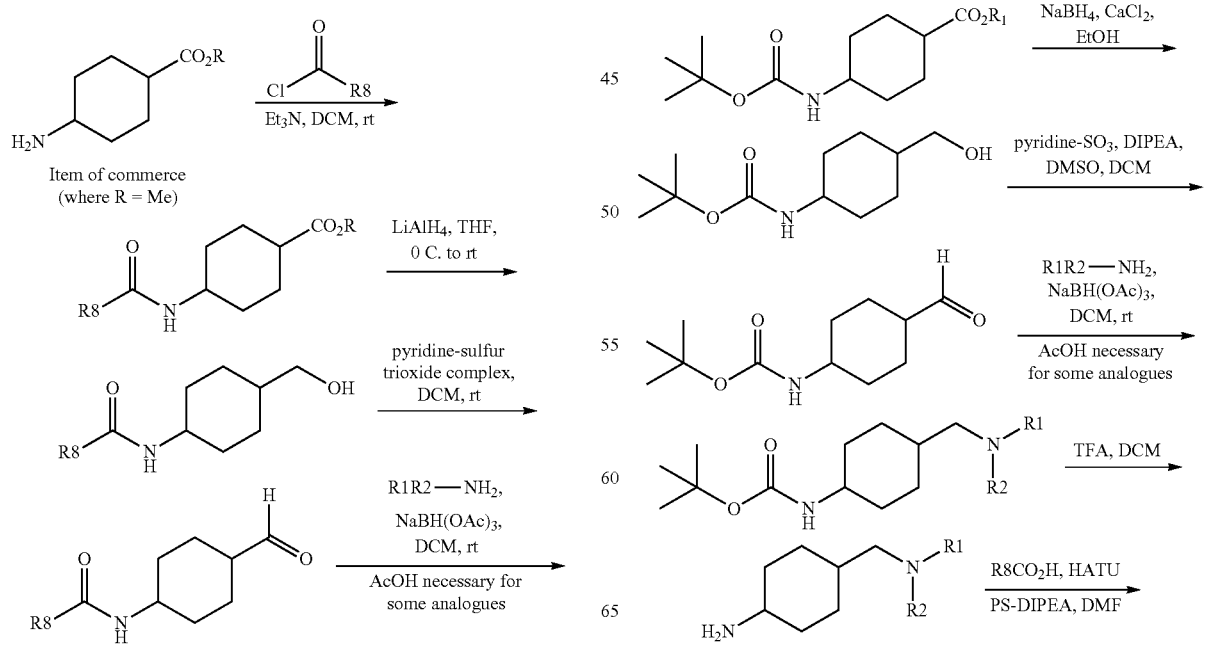

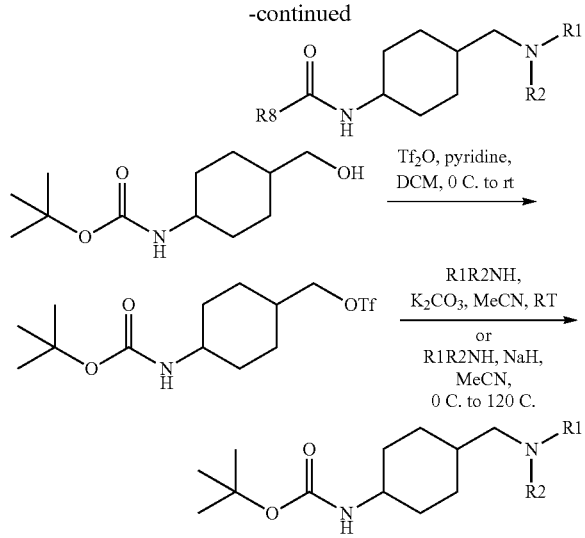

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

In addition various trade reagents and materials available from have been utilized. Such reagents and materials include IST PE-AX/SCX-2 and SCX-2 cartridges and can be readily obtained from the suppliers indicated.

General Conditions:

1H-NMR: Spectra are run on either a Bruker AVANCE 400 (400 MHz) spectrometer or on a Bruker AVANCE 500 (500 MHz) NMR spectrometer using ICON-NMR. Spectra are measured at 298K and are referenced using the solvent peak, chemical shifts ($\delta$-values) are reported in ppm, where included, coupling constants (J) are given in Hz, spectra splitting pattern are designated as singlet (s), doublet (d), triplet (t), quadruplet (q), multiplet or more overlapping signals (m), broad signal (br), solvent is given in parentheses.

MS: These are either Agilent 1100 HPLC/Micromass Platform Mass Spectrometer combinations or Waters Acquity UPLC with SQD Mass Spectrometer or Waters Alliance HT HPLC system equipped with a MS detector Waters MicromassZQ or Waters Micromass Plattform LCZ system. Mass spectra are run on LCMS systems using electrospray ionization. [M+H]+ refers to mono-isotopic molecular weights.

The various starting materials, intermediates, and compounds of the preferred embodiments may be isolated and purified, where appropriate, using conventional techniques such as precipitation, filtration, crystallization, evaporation, distillation, catch and release, and chromatography. Unless otherwise stated, all starting materials are obtained from commercial suppliers and used without further purification. Salts may be prepared from compounds by known salt-forming procedures.

Where a mixture of products was obtained, these were separated using Supercritical Fluids Chromatography (SFC). The general conditions for screening and preparative chiral separations by SFC were as follows:

Approximately 1.0 mg of sample is dissolved in 1.0 ml ethanol and screened on a Thar Minigram SFC system using the following chromatographic conditions:

Columns:
Chiralpak AD-H, 250×10 mm id, 5 μm
Chiralpak AS-H, 250×10 mm id, 5 μm
Chiralpak IC, 250×10 mm id, 5 μm
Chiralcel OD-H, 250×10 mm id, 5 μm
Chiralcel OJ-H, 250×10 mm id, 5 μm
Mobile Phase A:
Methanol (with the addition of 0.1% v/v DEA or TFA depending on the compound)
Mobile Phase B:
2-Propanol (with the addition of 0.1% v/v DEA or TFA depending on the compound)
Mobile Phase C: CO2
Screen 1 conditions:

| Gradient: | Time 0-3 min | 10% A | 90% C |
|---|---|---|---|
| | Time 3-10 min | 10-50% A | 90-50% C |
| | Time 10-13 min | 50% A | 50% C |
| | Time 13-14 min | 50-10% A | 50-90% C |
| | Time 14-15 min | 10% A | 90% C |

Screen 2 conditions:
As screen 1 but with mobile phase B replacing mobile phase A
Detection: UV @ 220 nm
Flow rate: 10 ml/min
Sample concentration: 1.0 mg in 1 ml ethanol
Injection volume: 30 μl The resulting chromatograms are examined for the best resolution of the sample. The optimum column and modifier are identified.

Optimisation of an isocratic method is then carried out to find a method suitable for the preparative separation.

The preparative separation is carried out on one of the five columns listed above and with either methanol or 2-propanol (with addition of DEA or TEA if necessary for optimum separation) and $CO_2$.

The total amount of sample is dissolved in ethanol, and multiple injections are carried out until all the sample solution is used. Injection volumes range from 50 μl to 200 μl depending on sample concentration and limit of loading on the column.

For the examples below as well as throughout the application, the following abbreviations have the following meanings. If not defined, the terms have their generally accepted meanings.

ABBREVIATIONS

DCM dichloromethane
DIPEA N,N-diisopropylethylamine
DMF N,N-dimethylformamide
EtOAc ethyl acetate
HATU  2-(1H-7-azabenzotriazol-1-yl)-1,1,3,3-tetramethyl uronium hexafluorophosphate
MeCN acetonitrile
MeOH methanol
min minute
PS-DIEA Polymer-supported diisopropylethylamine
PS-NCO Polymer-supported isocyanate
Rt Retention Time
RT room temperature
'BuOH tert-butanol
THF tetrahydrofuran If not indicated otherwise, the analytical HPLC conditions are as follows:
Method LowpH_v002.olp
Column Phenomenex Gemini C18 50×4.6 mm, 3.0 μm
Column Temperature 50° C.
Eluents A: $H_2O$, B: methanol, both containing 0.1% TFA
Flow Rate 1.0 ml/min
Gradient 5% to 95% B in 2.0 min, 0.2 min 95% B
Method 2 minLC_v002
Column Waters BEH C18 50×2.1 mm, 1.7 μm
Column Temperature 50° C.
Eluents A: $H_2O$, B: methanol, both containing 0.1% TFA
Flow Rate 0.8 ml/min
Gradient 0.20 min 5% B; 5% to 95% B in 1.30 min, 0.25 min 95% B Preparation of Final Compounds

EXAMPLE 1.1

Trans-5-Chloro-N-{4-[(5-ethyl-4-methyl-1H-pyrazol-3-ylamino)-methyl]-cyclohexyl}-2-methyl-nicotinamide

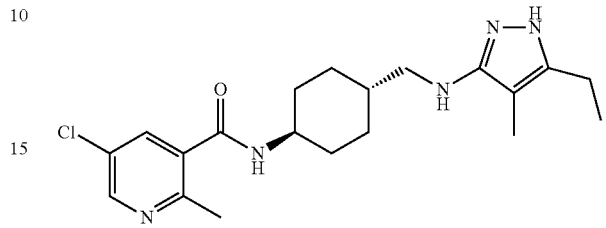

A mixture comprising trans-5-chloro-N-(4-formyl-cyclohexyl)-2-methyl-nicotinamide Intermediate E) (100 mg, 0.30 mmol) and 5-ethyl-4-methyl-1H-pyrazol-3-amine (37.5 mg, 0.30 mmol) in DCM (5 ml) was treated with sodium triacetoxyborohydride (95 mg, 0.45 mmol). The reaction mixture was stirred at RT for 18 hours and then partitioned between DCM and sat. $NaHCO_3$. The organic phase was passed through a phase separator and the solvent was removed in vacuo. The resulting crude product was triturated in EtOAc, filtered and dried to afford the title compound; $^1$H NMR (d6-DMSO, 400 MHz) δ 10.87 (1H, s), 8.53 (1H, m), 8.40 (1H, m), 7.80 (1H, m), 4.43 (1H, m), 3.69 (1H, m), 2.90 (2H, t), 2.50 (3H, s), 2.40 (2H, q), 1.88 (4H, m), 1.73 (3H, s), 1.53 (1H, m), 1.21 (2H, m), 1.09 (3H, t), 1.00 (2H, m); LCMS Rt=2.06 min, [M+H]$^+$390 Method LowpH_v002.

The compounds of the following tabulated Examples (Table 1) were prepared by a similar method to that of Example 1.1 using the appropriate benzamide or nicotinamide starting materials (the preparations of which are described in the 'Preparation of Intermediates' section) and the appropriate amine.

TABLE 1

| Ex. | Structure | Name | Retention Time (min), [M + H]$^+$ (Method LowpH_v002) (Unless otherwise specified) | $^1$H NMR |
|---|---|---|---|---|
| 1.2 | 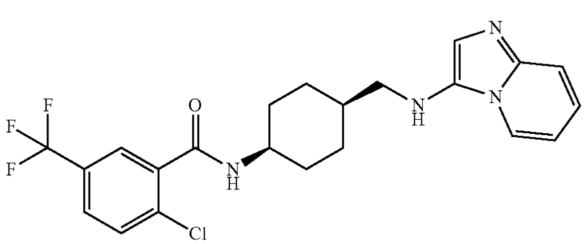 [SMILES: O=C(N[C@H]1CC[C@@H](CNc2cnc3ccccn23)CC1)c1cc(C(F)(F)F)ccc1Cl] | Trans-2-Chloro-N-[4-(imidazo[1,2-a]pyridin-3-ylaminomethyl)-cyclohexyl]-5-trifluoromethyl-benzamide | Rt 2.16 min [M + H]$^+$ 451.3 | (400 MHz, MeOD). δ8.1 (1H, d), 7.7 (4H, m), 7.4 (1H, d), 7.2 (1H, t), 6.9 (1H, t), 3.9 (1H, m), 3.1 (2H, d), 2.1 (4H, m), 1.7 (1H, m), 1.3 (4H, m). |

TABLE 1-continued

| Ex. | Structure | Name | Retention Time (min), [M + H]+ (Method LowpH_v002) (Unless otherwise specified) | ¹H NMR |
|---|---|---|---|---|
| 1.3* | (structure) | Trans-4-{[4-(2-Chloro-5-trifluoromethyl-benzoylamino)-cyclohexylmethyl]-amino}-benzoic acid | Rt 2.57 min [M + H]+ 455.4 | (d6-DMSO, 400 MHz) δ 8.5 (1H, d), 7.8 (3H, m), 7.6 (2H, d), 6.6 (2H, d), 3.7 (1H, m), 2.9 (2H, d), 1.9 (4H, dd), 1.5 (1H, m), 1.3 (2H, q), 1.1 (2H, q). |
| 1.4* | (structure) | Trans-(4-{[4-(2-Chloro-5-trifluoromethyl-benzoylamino)-cyclohexylmethyl]-amino}-phenyl)-acetic acid | Rt 2.18 min [M + H]+ 469.3 | (400 MHz, MeOD) δ 8.6 (~0.5, d-amide proton slow exchange), 7.7 (3H, m), 7.3 (2H, d), 7.0 (2H, m), 3.9 (1H, m), 3.6 (2H, s), 3.1 (2H, d), 2.2 (2H, d), 2.0 (2H, d), 1.7 (1H, m), 1.4 (2H, q), 1.2 (2H, q). |
| 1.5 | (structure) | Trans-5-Chloro-2-methyl-N-{4-[(1H-pyrazolo[4,3-b]pyridin-3-ylamino)-methyl]-cyclohexyl}-nicotinamide | Rt 2.16 min [M + H]+ 399.3 | (400 MHz, MeOD). δ 8.5 (2H, m), 8.1 (1H, d), 7.8 (1H, s), 7.7 (1H, m), 3.9 (1H, m), 3.4 (2H, d), 2.6 (3H, s), 2.1 (2H, d), 2.0 (2H, d), 1.8 (1H, m), 1.3 (4H, m). |
| 1.6 | (structure) | Trans-2-Chloro-N-{4-[(5-methyl-4-pyridin-3-yl-2H-pyrazol-3-ylamino)-methyl]-cyclohexyl}-5-trifluoromethyl-benzamide | Rt 2.02 min [M + H]+ 492.28 | (d6-DMSO, 400 MHz) δ 11.50 (1H, s), 8.57 (1H, m), 8.49 (1H, d, 8.39 (1H, m), 7.81 (1H, m), 7.71 (3H, m), 7.39 (1H, m), 3.70 (1H, m), 2.92 (2H, t), 2.16 (3H, s), 1.91 (2H, m), 1.81 (2H, m), 1.59 (1H, m), 1.20 (2H, m), 1.00 (2H, m). |
| 1.7* | (structure) | Trans-(3-{[4-(2-Chloro-5-trifluoromethyl-benzoylamino)-cyclohexylmethyl]-amino}-phenyl)-acetic acid | Rt 2.20 min [M + H]+ 469.4 | (d6-DMSO, 400 MHz) δ 8.5 (1H, d), 7.8 (1H, d), 7.7 (2H, d), 7.2 (1H, s), 6.8 (3H, m), 3.7 (1H, m), 3.5 (2H, s), 3.0 (2H, s), 1.9 (4H, t), 1.6 (1H, m), 1.2 (2H, q), 1.1 (2H, q). |

TABLE 1-continued

| Ex. | Structure | Name | Retention Time (min), [M + H]+ (Method LowpH_v002) (Unless otherwise specified) | 1H NMR |
|---|---|---|---|---|
| 1.8 | 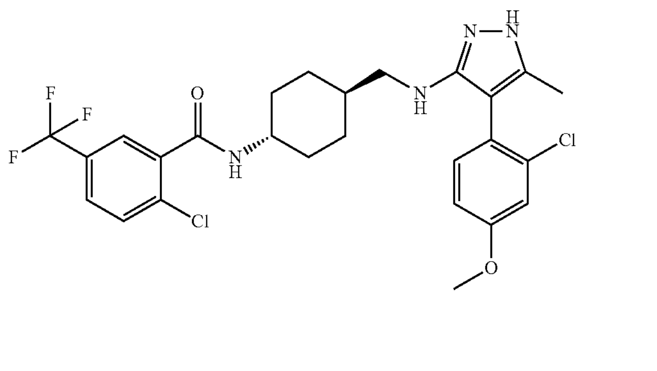 [SMILES: COc1ccc(-c2c(NC[C@H]3CC[C@H](NC(=O)c4cc(C(F)(F)F)ccc4Cl)CC3)n[nH]c2C)c(Cl)c1] | Trans-2-Chloro-N-(4-{[4-(2-chloro-4-methoxy-phenyl)-5-methyl-1H-pyrazol-3-ylamino]-methyl}-cyclohexyl)-5-trifluoromethyl-benzamide | 1.43 min [M + H]+ 555.3 (Method 2 minLC_v002) | (400 MHz, MeOD) δ 7.79 (1H, s), 7.52 (1H, d), 7.43 (1H, d), 7.10 (1H, d), 6.98 (1H, s), 6.80 (1H, d), 5.88 (1H, d), 3.88 (1H, m), 3.75 (3H, m), 3.05 (2H, m), 2.07 (2H, m), 2.05 (3H, s), 1.83 (2H, m), 1.55 (1 h, m), 1.0-1.2 (4H, m). |
| 1.9* | 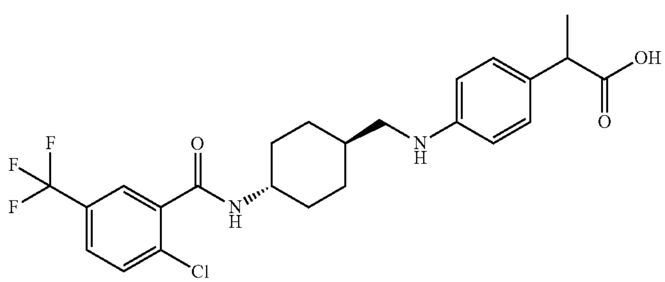 [SMILES: CC(C(=O)O)c1ccc(NC[C@H]2CC[C@H](NC(=O)c3cc(C(F)(F)F)ccc3Cl)CC2)cc1] | Trans-2-(4-{[4-(2-Chloro-5-trifluoromethyl-benzoylamino)-cyclohexylmethyl]-amino}-phenyl)-propionic acid | Rt 2.22 min [M + H]+ 483.4 | (400 MHz, DMSO-d6) δ8.5 (1H, d), 7.8 (1H, d), 7.7 (2H, d), 7.1 (2H, s), 6.8 (2H, s), 3.8 (2H, m), 3.5 (1H, m), 3.0 (2H, d), 1.9 (4H, q), 1.5 (1H, m), 1.3 (3H, d), 1.2 (2H, m), 1.1 (2H, q). |

*prepared from corresponding methyl esters by hydrolysis using NaOH in MeOH/THF.

EXAMPLE 2.0

Trans-5-chloro-N-[4-(3,5-diethyl-pyrazol-1-ylmethyl)-cyclohexyl]-2-methyl-nicotinamide

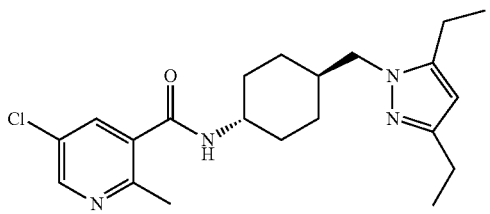 [SMILES: CCc1cc(CC)n(C[C@H]2CC[C@H](NC(=O)c3cc(Cl)cnc3C)CC2)n1]

Trans-4-(3,5-diethyl-pyrazol-1-ylmethyl)-cyclohexylamine hydrochloride (Intermediate B) (65 mg, 0.238 mmol) was placed in a flask with DCM (5 ml) and triethylamine (72 mg, 0.714 mmol). 5-Chloro-2-methylnicotinoyl chloride (Intermediate C) (54 mg, 0.238 mmol) was added portionwise. After addition of the acid chloride, the reaction mixture was stirred at RT for 1 hour and partitioned between DCM and sat. NaHCO₃. The organic phase was passed through a phase separator and the solvent was removed in vacuo. The crude product was triturated in EtOAc:iso-hexane—1:1, filtered and dried to afford the title compound; ¹H NMR (d6-DMSO, 400 MHz) δ 8.52 (1H, d), 8.39 (1H, d), 7.79 (1H, d), 5.82 (1H, s), 3.76 (2H, d), 3.67 (1H, m), 2.57 (2H, q), 2.47 (5H, m), 1.89 (2H, m), 1.72 (1H, m), 1.57 (2H, m), 1.23 (10H, m); LC-MS Rt 2.35 mins, [M+H]+ 389; Method LowpH_v002.

The compounds of the following tabulated Examples (Table 2) are prepared by a similar method to that of Example 2.0 from 5-chloro-2-methylnicotinoyl chloride (Intermediate C) or 2-chloro-5-trifluoromethyl-benzoyl chloride and the appropriate pyrazoloamine (the preparations of which are described in the 'Preparation of Intermediates' section). Where a mixture of regioisomers were obtained, these were separated using the conditions described in the 'General Conditions' section.

TABLE 2

| Ex. | Structure | Name | Retention Time (min), [M + H]+ (Method LowPH_v002) | 1H NMR |
|---|---|---|---|---|
| 2.1 | 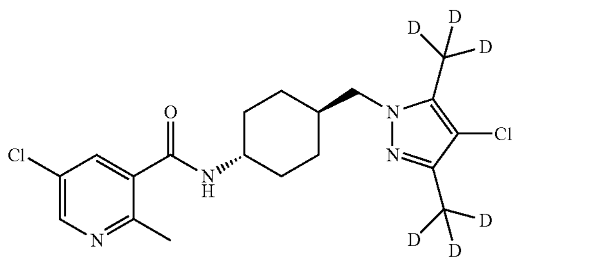 [SMILES: [2H]C([2H])([2H])c1nn(C[C@H]2CC[C@H](NC(=O)c3cc(Cl)cnc3C)CC2)c(C([2H])([2H])[2H])c1Cl] | Trans-5-Chloro-N-[4-(4-chloro-3,5-d6-dimethyl-pyrazol-1-ylmethyl)-cyclohexyl]-2-methyl-nicotinamide | Rt 2.58 min; [M + H]+ 401.51 | (d6-DMSO, 400 MHz) δ 8.52 (1H, d), 8.39 (1H, d), 7.79 (1H, d), 3.81 (2H, d), 3.67 (1H, m), 2.47 (3H, s), 1.89 (2H, m), 1.72 (1H, m), 1.56 (2H, m), 1.17 (4H, m). |
| 2.2 | 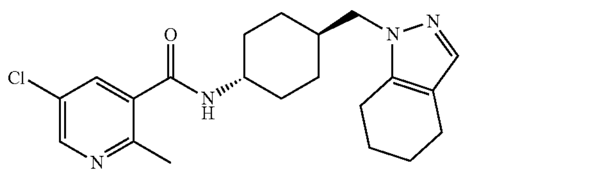 [SMILES: Cc1ncc(Cl)cc1C(=O)N[C@H]1CC[C@H](Cn2ncc3c2CCCC3)CC1] | Trans-5-Chloro-2-methyl-N-[4-(4,5,6,7-tetrahydro-indazol-1-ylmethyl)-cyclohexyl]-nicotinamide | Rt 2.39 min; [M + H]+ 387.5 | (400 MHz, CDCl$_3$) δ 8.48 (1H, d), 7.60 (1H, d), 7.03 (1H, s), 5.84 (1H, br d), 3.92 (1H, m), 3.86 (2H, d), 2.66 (2H, t), 2.60 (3H, s), 2.53 (2H, t), 2.12 (2H, m), 1.89 (1H, m), 1.85-1.70 (6H, m), 1.19 (4H, m). |
| 2.3 | 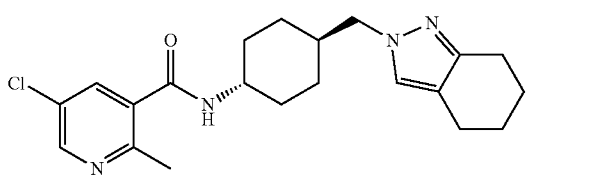 [SMILES: Cc1ncc(Cl)cc1C(=O)N[C@H]1CC[C@H](Cn2cc3c(n2)CCCC3)CC1] | Trans-5-Chloro-2-methyl-N-[4-(4,5,6,7-tetrahydro-indazol-2-ylmethyl)-cyclohexyl]-nicotinamide | Rt 2.38 min; [M + H]+ 387.5 | (400 MHz, CDCl3) δ 8.48 (1H, d), 7.60 (1H, d), 7.25 (1H, s), 5.86 (1H, br d), 3.93 (1H, m), 3.80 (2H, d), 2.60 (3H, s), 2.55 (2H, t), 2.51 (2H, t), 2.12 (2H, m), 1.94 (1H, m), 1.87-1.69 (6H, m), 1.20 (4H, m). |
| 2.4 | 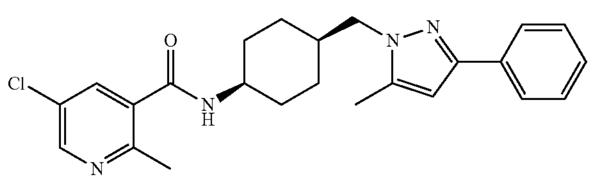 [SMILES: Cc1ncc(Cl)cc1C(=O)N[C@H]1CC[C@@H](Cn2nc(-c3ccccc3)cc2C)CC1] | Trans-5-Chloro-2-methyl-N-[4-(5-methyl-3-phenyl-pyrazol-1-ylmethyl)-cyclohexyl]-nicotinamide | Rt 2.58 min; [M + H]+ 423.65 | (d6-DMSO, 400 MHz) δ 8.52 (1H, d), 8.40 (1H, d), 7.79 (1H, d), 7.72 (2H, d), 7.38 (2H, t), 7.27 (1H, t), 6.45 (1H, s), 3.91 (2H, d), 3.70 (1H, m), 2.47 (3H, s), 2.30 (3H, s), 1.90 (2H, m), 1.81 (1H, m), 1.62 (2H, m), 1.20 (4H, m). |
| 2.5 | 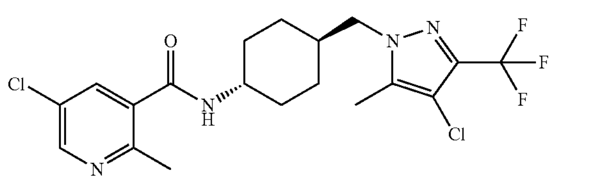 [SMILES: Cc1ncc(Cl)cc1C(=O)N[C@H]1CC[C@H](Cn2nc(C(F)(F)F)c(Cl)c2C)CC1] | Trans-5-Chloro-N-[4-(4-chloro-5-methyl-3-trifluoromethyl-pyrazol-1-ylmethyl)-cyclohexyl]-2-methyl-nicotinamide | Rt 2.63 min; [M + H]+ 449.5 | (d6-DMSO, 400 MHz) δ 8.52 (1H, d), 8.40 (1H, d), 7.80 (1H, d), 4.03 (2H, d), 3.69 (1H, m), 2.48 (3H, s), 2.21 (3H, s), 1.90 (2H, m), 1.80 (1H, m), 1.49 (2H, m), 1.20 (4H, m). |

TABLE 2-continued

| Ex. | Structure | Name | Retention Time (min), [M + H]+ (Method LowpH_v002) | 1H NMR |
|---|---|---|---|---|
| 2.6 | 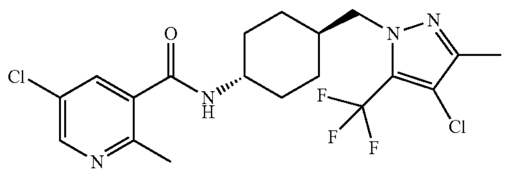 [SMILES: Cc1ncc(Cl)cc1C(=O)N[C@H]1CC[C@H](Cn2nc(C)c(Cl)c2C(F)(F)F)CC1] | Trans-5-Chloro-N-[4-(4-chloro-3-methyl-5-trifluoromethyl-pyrazol-1-ylmethyl)-cyclohexyl]-2-methyl-nicotinamide | Rt 2.69 min; [M + H]+ 449.53 | (d6-DMSO, 400 MHz) δ 8.52 (1H, d), 8.40 (1H, d), 7.79 (1H, d), 4.03 (2H, d), 3.69 (1H, m), 2.48 (3H, s), 2.20 (3H, s), 1.90 (2H, m), 1.81 (1H, m), 1.57 (2H, m), 1.18 (4H, m). |
| 2.7 | 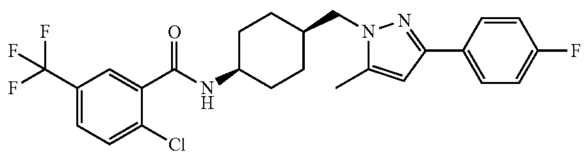 [SMILES: Cc1cc(-c2ccc(F)cc2)nn1C[C@H]1CC[C@@H](NC(=O)c2cc(C(F)(F)F)ccc2Cl)CC1] | Trans-2-Chloro-N-{4-[3-(4-fluoro-phenyl)-5-methyl-pyrazol-1-ylmethyl]-cyclohexyl}-5-trifluoromethyl-benzamide | Rt 2.69 min; [M + H]+ 494.48 | (d6-DMSO, 400 MHz) δ 8.50 (1H, d), 7.78 (5H, m), 7.20 (2H, m), 6.45 (1H, s), 3.91 (2H, d), 3.70 (1H, m), 2.29 (3H, s), 1.92 (2H, m), 1.81 (1H, m), 1.61 (2H, m), 1.19 (4H, m). |
| 2.8 | 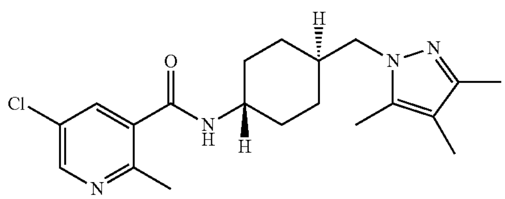 [SMILES: Cc1ncc(Cl)cc1C(=O)N[C@H]1CC[C@H](Cn2nc(C)c(C)c2C)CC1] | Trans-5-Chloro-2-methyl-N-[4-(3,4,5-trimethyl-pyrazol-1-ylmethyl)-cyclohexyl]-nicotinamide | Rt 1.97 min; [M + H]+ 375.3 | (d6-DMSO, 400 MHz) δ 8.54 1H, d), 8.39 (1H, d), 7.79 (1H, d), 3.74 (2H, d), 3.67 (1H, m), 2.47 (3H, s), 2.10 (3H, s), 2.02 (3H, s), 1.88 (2H, m), 1.83 (3H, m), 1.70 (1H, m), 1.57 (2H, m), 1.14 (4H, m). |
| 2.9 | 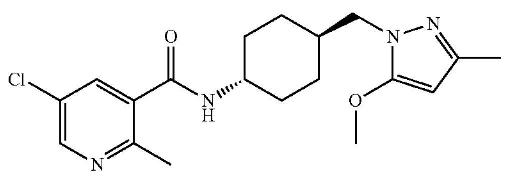 [SMILES: COc1cc(C)nn1C[C@H]1CC[C@H](NC(=O)c2cc(Cl)cnc2C)CC1] | Trans-5-Chloro-N-[4-(5-methoxy-3-methyl-pyrazol-1-ylmethyl)-cyclohexyl]-2-methyl-nicotinamide | Rt 2.08 min; [M + H]+ 377.44 | (CDCl3, 400 MHz) δ 8.50 (1H, d), 7.61 (1H, d), 5.61 (1H, d), 5.32 (1H, s), 3.92 (1H, m), 3.86 (3H, s), 3.73 (2H, d), 2.61 (3H, s), 2.20 (3H, s), 2.11 (2H, m), 1.89 (1H, m), 1.72 (2H, m), 1.20 (4H, m). |
| 2.10 | 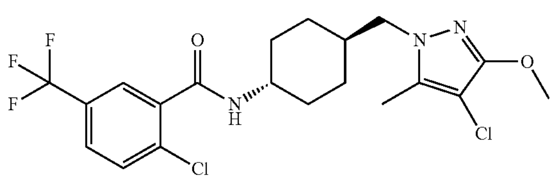 [SMILES: COc1nn(C[C@H]2CC[C@H](NC(=O)c3cc(C(F)(F)F)ccc3Cl)CC2)c(C)c1Cl] | Trans-2-Chloro-N-[4-(4-chloro-3-methoxy-5-methyl-pyrazol-1-ylmethyl)-cyclohexyl]-5-trifluoromethyl-benzamide | Rt 2.60 min; [M + H]+ 464.41 | (CDCl3, 400 MHz) δ 7.81 (1H, d), 7.52 (1H, m), 7.44 (1H, m), 5.89 (1H, d), 3.90 (1H, m), 3.88 (3H, s), 3.68 (2H, d), 2.12 (3H, s), 2.10 (2H, m), 1.81 (1H, m), 1.65 (2H, m), 1.13 (4H, m). |
| 2.11 | 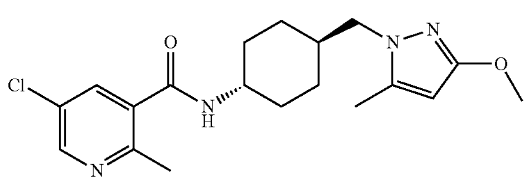 [SMILES: COc1cc(C)n(C[C@H]2CC[C@H](NC(=O)c3cc(Cl)cnc3C)CC2)n1] | Trans-5-Chloro-N-[4-(3-methoxy-5-methyl-pyrazol-1-ylmethyl)-cyclohexyl]-2-methyl-nicotinamide | Rt 2.31 min [M + H]+ 377.45 | (CDCl3, 400 MHz) δ 8.40 (1H, d), 7.52 (1H, d), 5.65 (1H, d), 5.32 (1H, s), 3.83 (1H, m), 3.74 (3H, s), 3.61 (2H, d), 2.52 (3H, s), 2.11 (3H, s), 2.02 (2H, m), 1.87 (1H, m), 1.66 (2H, m), 1.10 (4H, m). |

TABLE 2-continued

| Ex. | Structure | Name | Retention Time (min), [M + H]+ (Method LowpH_v002) | 1H NMR |
|---|---|---|---|---|
| 2.12 | 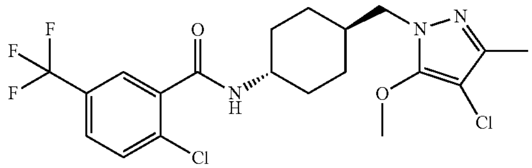 [SMILES: COc1c(Cl)c(C)nn1C[C@H]1CC[C@H](NC(=O)c2cc(C(F)(F)F)ccc2Cl)CC1] | Trans-2-Chloro-N-[4-(4-chloro-5-methoxy-3-methyl-pyrazol-1-ylmethyl)-cyclohexyl]-5-trifluoromethyl-benzamide | Rt 2.63 min; [M + H]+ 464.4 | (CDCl3, 400 MHz) δ 7.90 (1H, d), 7.61 (1H, m), 7.51 (1H, m), 5.97 (1H, d), 4.09 (3H, s), 3.98 (1H, m), 3.75 (2H, d), 2.20 (3H, s), 2.18 (2H, m), 1.89 (1H, m), 1.71 (2H, m), 1.21 (4H, m). |
| 2.13 | 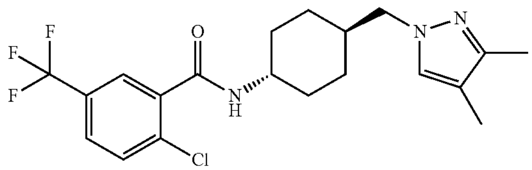 [SMILES: Cc1cn(C[C@H]2CC[C@H](NC(=O)c3cc(C(F)(F)F)ccc3Cl)CC2)nc1C] | Trans-2-Chloro-N-[4-(3,4-dimethyl-pyrazol-1-ylmethyl)-cyclohexyl]-5-trifluoromethyl-benzamide | Rt 2.40 min; [M + H]+ 414.45 | (CDCl3, 400 MHz) δ 7.90 (1H, d), 7.62 (1H, m), 7.53 (1H, m), 5.98 (1H, d), 3.99 (1H, m), 3.88 (2H, d), 2.21 (3H, s), 2.18 (2H, m), 2.00 (3H, s), 1.92 (1H, m), 1.74 (2H, m), 1.21 (4H, m). |
| 2.14 | 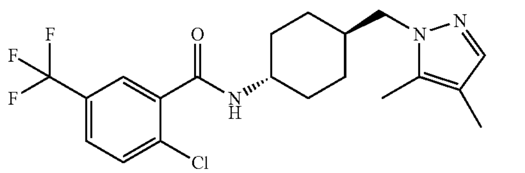 [SMILES: Cc1cnn(C[C@H]2CC[C@H](NC(=O)c3cc(C(F)(F)F)ccc3Cl)CC2)c1C] | Trans-2-Chloro-N-[4-(4,5-dimethyl-pyrazol-1-ylmethyl)-cyclohexyl]-5-trifluoromethyl-benzamide | Rt 2.40 min; [M + H]+ 414.45 | (CDCl3, 400 MHz) δ 7.90 (1H, d), 7.61 (1H, m), 7.53 (1H, m), 5.97 (1H, d), 3.99 (1H, m), 3.90 (2H, d), 2.20 (3H, s), 2.16 (2H, m), 2.02 (3H, s), 1.99 (1H, m), 1.75 (2H, m), 1.22 (4H, m). |
| 2.15 | 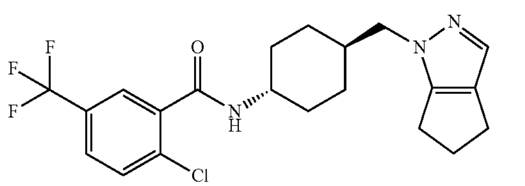 [SMILES: O=C(N[C@H]1CC[C@H](Cn2ncc3c2CCC3)CC1)c1cc(C(F)(F)F)ccc1Cl] | Trans-2-Chloro-N-[4-(5,6-dihydro-4H-cyclopentapyrazol-1-ylmethyl)-cyclohexyl]-5-trifluoromethyl-benzamide | Rt 2.49 min; [M + H]+ 426.49 | (500 MHz, DMSO) δ 8.49 (1H, d), 7.69 (1H, d), 7.62 (2H, m), 7.05 (1H, s), 3.80 (2H, d) 3.68 (1H, m), 2.66 (2H, m), 2.48 (2H, m), 1.91 (2H, m), 1.73 (1H, m), 1.59 (2H, m), 1.21 (2H, m), 1.08 (2H, m). |
| 2.16 | 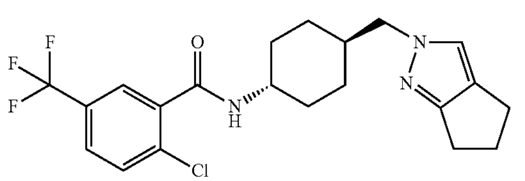 [SMILES: O=C(N[C@H]1CC[C@H](Cn2cc3c(n2)CCC3)CC1)c1cc(C(F)(F)F)ccc1Cl] | Trans-2-Chloro-N-[4-(5,6-dihydro-4H-cyclopentapyrazol-2-ylmethyl)-cyclohexyl]-5-trifluoromethyl-benzamide | Rt 2.49 min; [M + H]+ 426.49 | (500 MHz, DMSO) δ 8.49 (1H, d), 7.69 (1H, d), 7.62 (2H, m), 7.26 (1H, s), 3.83 (2H, d) 3.68 (1H, m), 2.53 (2H, m), 2.30 (2H, m), 1.92 (2H, m), 1.72 (1H, m), 1.56 (2H, m), 1.20 (2H, m), 1.06 (2H, m). |
| 2.17 | 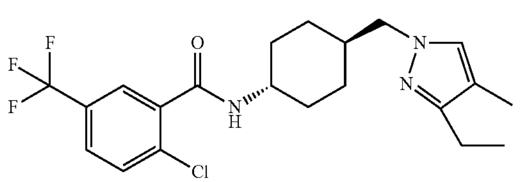 [SMILES: CCc1nn(C[C@H]2CC[C@H](NC(=O)c3cc(C(F)(F)F)ccc3Cl)CC2)cc1C] | Trans-2-Chloro-N-[4-(3-ethyl-4-methyl-pyrazol-1-ylmethyl)-cyclohexyl]-5-trifluoromethyl-benzamide | Rt 2.45 min; [M + H]+ 428.43 | (400 MHz, DMSO) δ 8.48 (1H, d), 7.81 (1H, m), 7.73 (2H, m) 7.31 (1H, s), 3.78 (2H, d), 3.67 (1H, m), 2.46 (2H, q), 1.94 (3H, s), 1.90 (2H, m), 1.70 (1H, m), 1.55 (2H, m), 1.20 (2H, m), 1.11 (3H, t), 1.04 (2H, m). |

TABLE 2-continued

| Ex. | Structure | Name | Retention Time (min), [M + H]+ (Method LowpH_v002) | 1H NMR |
|---|---|---|---|---|
| 2.18 | 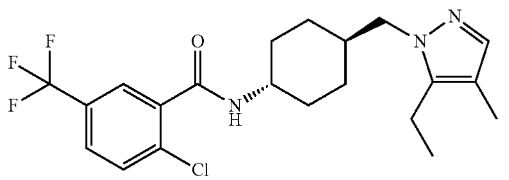 [SMILES: CCc1c(C)cnn1C[C@H]1CC[C@H](NC(=O)c2cc(C(F)(F)F)ccc2Cl)CC1] | Trans-2-Chloro-N-[4-(5-ethyl-4-methyl-pyrazol-1-ylmethyl)-cyclohexyl]-5-trifluoromethyl-benzamide | Rt 2.45 min; [M + H]+ 428.43 | (400 MHz, DMSO) δ 8.48 (1H, d), 7.82 (1H, m), 7.73 (2H, m), 7.13 (1H, s), 3.82 (2H, d), 3.70 (1H, m), 2.60 (2H, q), 1.95 (3H, s), 1.90 (2H, m), 1.77 (1H, m), 1.55 (2H, m), 1.17 (2H, m), 1.06 (3H, t). |
| 2.19 | 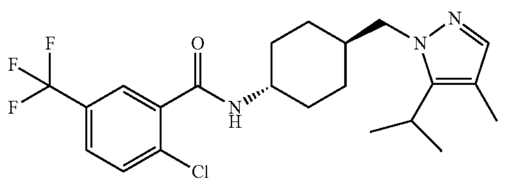 [SMILES: Cc1cnn(C[C@H]2CC[C@H](NC(=O)c3cc(C(F)(F)F)ccc3Cl)CC2)c1C(C)C] | Trans-2-Chloro-N-[4-(5-isopropyl-4-methyl-pyrazol-1-ylmethyl)-cyclohexyl]-5-trifluoromethyl-benzamide | Rt 2.50 min; [M + H]+ 442.39 | (400 MHz, CDCl3) δ 7.91 (1H, d), 7.62 (1H, m), 7.53 (1H, m), 7.26 (1H, s), 5.98 (1H, d), 4.00 (1H, m), 3.92 (2H, d), 3.08 (1H, sept), 2.19 (2H, m), 2.13 (3H, s), 1.97 (1H, m), 1.72 (2H, m), 1.32 (6H, d), 1.22 (4H, m). |
| 2.20 | 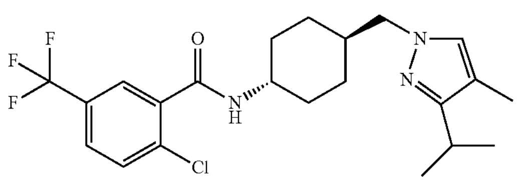 [SMILES: Cc1cn(C[C@H]2CC[C@H](NC(=O)c3cc(C(F)(F)F)ccc3Cl)CC2)nc1C(C)C] | Trans-2-Chloro-N-[4-(3-isopropyl-4-methyl-pyrazol-1-ylmethyl)-cyclohexyl]-5-trifluoromethyl-benzamide | Rt 2.50 min; [M + H]+ 442.39 | (400 MHz, CDCl3) δ 7.90 (1H, d), 7.61 (1H, m), 7.52 (1H, m), 7.05 (1H, s), 5.96 (1H, d), 3.96 (1H, m), 3.87 (2H, d), 3.01 (1H, sept), 2.17 (2H, m), 2.15 (3H, s), 1.90 (1H, m), 1.73 (2H, m), 1.30 (6H, d), 1.19 (4H, m). |
| 2.21 | 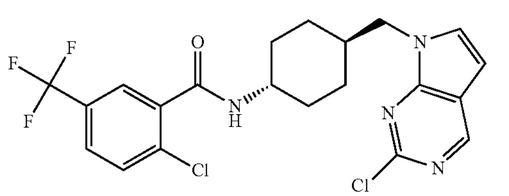 [SMILES: O=C(N[C@H]1CC[C@H](Cn2ccc3cnc(Cl)nc32)CC1)c1cc(C(F)(F)F)ccc1Cl] | Trans-2-Chloro-N-[4-(2-chloro-pyrrolo[2,3-d]pyrimidin-7-ylmethyl)-cyclohexyl]-5-trifluoromethyl-benzamide | Rt 2.57 min; [M + H]+ 471.17 | (400 MHz, DMSO) δ 8.95 (1H, s), 8.45 (1H, d), 7.8 (1H, d), 7.7 (3H, m), 6.7 (1H, s), 4.1 (2H, d), 3.7 (1H, m), 1.9 (3H, m), 1.55 (2H, m), 1.2 (4H, m). |

EXAMPLE 2.22

Trans-5-Chloro-N-(4-[(3-chloro-6-methoxy-pyridin-2-ylamino)-methyl]-cyclohexyl)-2-methyl-nicotinamide

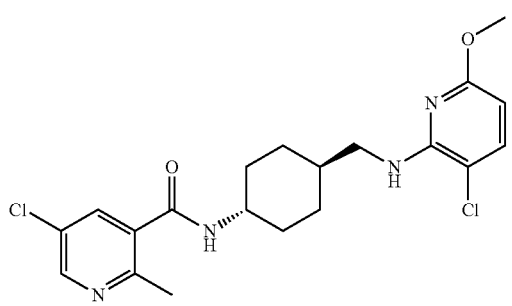 [SMILES: COc1ccc(Cl)c(NC[C@H]2CC[C@H](NC(=O)c3cc(Cl)cnc3C)CC2)n1]

The title compound is prepared from 5-chloro-2-methylnicotinoyl chloride (Intermediate C) and trans-(4-Amino-cyclohexylmethyl)-(3-chloro-6-methoxy-pyridin-2-yl)-amine (Intermediate BB) analogously to Example 2.0; 1H NMR (d6-DMSO, 400 MHz) δ 8.52 (1H, d), 8.39 (1H, d), 7.80 (1H, d), 7.42 (1H, d), 6.45 (1H, t), 5.90 (1H, d), 3.79 (3H, s), 3.69 (1H, my 3.22 (2H, t), 2.48 (3H, a), 1.91 (2H, m), 1.80 (2H, m), 1.60 (1H, m), 1.21 (2H, m), 1.07 (2H, m); LC-MS Rt 2.70 mins, [M+H]+ 423.55; Method LowpH_v002.

EXAMPLES 3.1 AND 3.2

Trans-5-Chloro-N-[4-(5,6-dihydro-4H-cyclopentapyrazol-1-ylmethyl)-cyclohexyl]-2-methyl-nicotinamide and Trans-5-Chloro-N-[4-(5,6-dihydro-4H-cyclopentapyrazol-2-ylmethyl)-cyclohexyl]-2-methyl-nicotinamide

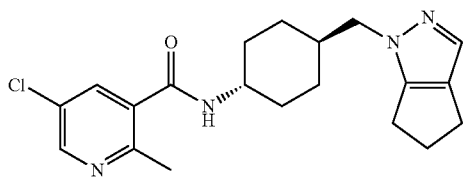

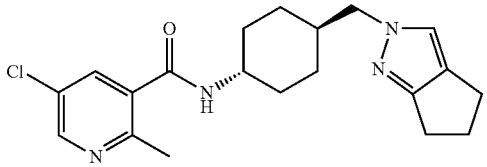

Trans-4-(5,6-dihydro-4H-cyclopentapyrazol-1-ylmethyl)-cyclohexylamine (Intermediate H) (118 mg, 0.461 mmol) was suspended in DMF (2 ml) and treated with 5-chloro-2-methyl-nicotinic acid (96 mg, 0.461 mmol) and HATU (210 mg, 0.554 mmol) DIPEA (0.321 ml, 1.845 mmol) was added and the reaction mixture was stirred at RT for 1 hour. The mixture was partitioned between DCM and water and the organic phase was separated and washed with water, brine, dried (MgSO$_4$) and the solvent was removed in vacuo. The crude product was purified by chromatography on basic Alumina, eluting with a iso-hexane/EtOAc to afford a ~1:1 mixture of regiosisomers. LCMS Rt=2.15 min; [M+H]+ 373. Method LowpH_v002. The mixture was separated using by SFC using conditions described in the 'General Conditions' section.

Ex. 3.1: Trans-5-Chloro-N-[4-(5,6-dihydro-4H-cyclopentapyrazol-1-ylmethyl)-cyclohexyl]-2-methyl-nicotinamide 1H NMR (500 MHz, DMSO) δ 8.52 (1H, d), 8.40 (1H, d), 7.78 (1H, d), 7.06 (1H, s), 3.80 (2H, d) 3.66 (1H, m), 2.66 (2H, m), 2.51 (2H, m), 2.47 (3H, s), 1.91 (2H, m), 1.73 (1H, m), 1.59 (2H, m), 1.21 (2H, m), 1.08 (2H, m).

Ex. 3.2: Trans-5-Chloro-N-[4-(5,6-dihydro-4H-cyclopentapyrazol-2-ylmethyl)-cyclohexyl]-2-methyl-nicotinamide 1H NMR (500 MHz, DMSO) δ 8.52 (1H, d), 8.40 (1H, d), 7.78 (1H, d), 7.27 (1H, s), 3.83 (2H, d) 3.65 (1H, m), 2.53 (2H, m), 2.48 (3H, s), 2.30 (2H, m), 1.89 (2H, m), 1.71 (1H, m), 1.58 (2H, m), 1.20 (2H, m), 1.05 (2H, m).

The compounds of the following tabulated Examples (Table 3) were prepared from 5-chloro-2-methyl-nicotinic acid by a similar method to that of Example 3.1 and 3.2 using the appropriate amine the preparations of which are described in the 'Preparation of Intermediates' section.

TABLE 3

| Ex. | Structure | Name | Retention Time (min), [M + H]+ (Method LowpH_v002) | 1H NMR |
|---|---|---|---|---|
| 3.3 | 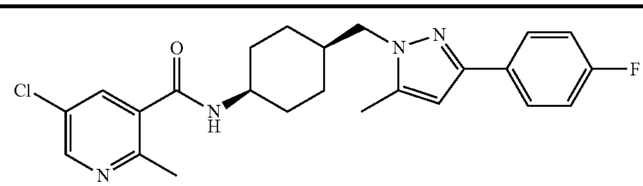 | Trans-5-Chloro-N-{4-[3-(4-fluoro-phenyl)-5-methyl-pyrazol-1-ylmethyl]-cyclohexyl}-2-methyl-nicotinamide | Rt 2.62 min; [M + H]+ 441.54 | (400 MHz, DMSO) δ 8.52 (1H, d), 8.40 (1H, d),7.78 (3H, m), 7.20 (2H, m), 6.47 (1H, s), 3.90 (2H, d), 3.69 (1H, m), 2.45 (3H, s), 2.29 (3H, s), 1.90 (2H, m), 1.82 (1H, m), 1.61 (2H, m), 1.20 (4H, m). |

TABLE 3-continued

| Ex. | Structure | Name | Retention Time (min), [M + H]⁺ (Method LowpH_v002) | ¹H NMR |
|---|---|---|---|---|
| 3.4 | 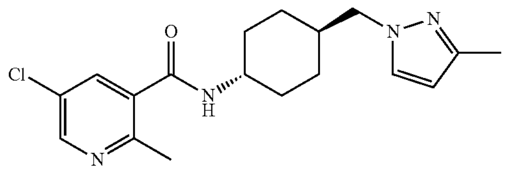 [SMILES: Cc1ccn(C[C@H]2CC[C@H](NC(=O)c3cc(Cl)cnc3C)CC2)n1] | Trans-5-Chloro-2-methyl-N-[4-(3-methyl-pyrazol-1-ylmethyl)-cyclohexyl]-nicotinamide | Rt 2.20 min; [M + H]⁺ 347.3 | (400 MHz, DMSO) δ 8.53 (1H, d), 8.39 (1H, br d), 7.78 (1H, d), 7.53 (1H, d), 5.97 (1H, d), 3.85 (2H, d), 3.66 (1H, m), 2.47 (3H, s), 2.14 (3H, s), 1.88 (2H, m), 1.73 (1H, m), 1.56 (2H, m), 1.21 (2H, m), 1.06 (2H, m). |
| 3.5 | 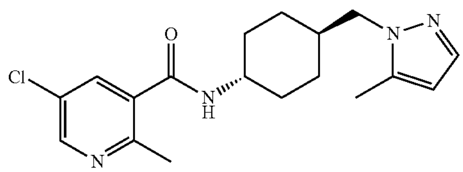 [SMILES: Cc1ncc(Cl)cc1C(=O)N[C@H]1CC[C@H](Cn2nccc2C)CC1] | Trans-5-Chloro-2-methyl-N-[4-(5-methyl-pyrazol-1-ylmethyl)-cyclohexyl]-nicotinamide | Rt 2.19 min; [M + H]⁺ 347.3 | (400 MHz, DMSO) δ 8.53 (1H, d), 8.37 (1H, br d), 7.78 (1H, d), 7.29 (1H, d), 5.99 (1H, m), 3.86 (2H, d), 3.68 (1H, m), 2.47 (3H, s), 2.25 (3H, s), 1.89 (2H, m), 1.76 (1H, m), 1.56 (2H, m), 1.16 (4H, m). |
| 3.6 | 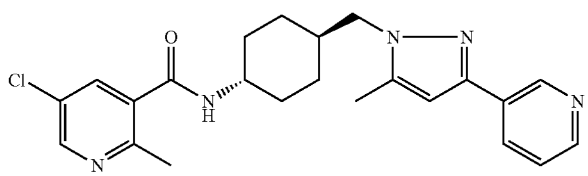 [SMILES: Cc1ncc(Cl)cc1C(=O)N[C@H]1CC[C@H](Cn2nc(-c3cccnc3)cc2C)CC1] | Trans-5-Chloro-2-methyl-N-[4-(5-methyl-3-pyridin-3-yl-pyrazol-1-ylmethyl)-cyclohexyl]-nicotinamide | Rt 1.96 min; [M + H]⁺ 424.52 | (400 MHz, DMSO) δ 8.95 (1H, d), 8.55 (1H, d), 8.48 (1H, d), 8.40 (1H, d), 8.09 (1H, m), 7.69 (1H, d), 7.50 (1H, m), 6.58 (1H, d), 3.93 (2H, d), 3.70 (1H, m), 2.46 (3H, s), 2.41 (3H, s), 1.90 (4H, m), 1.82 (1H, m), 1.62 (4H, m). |
| 3.7 | 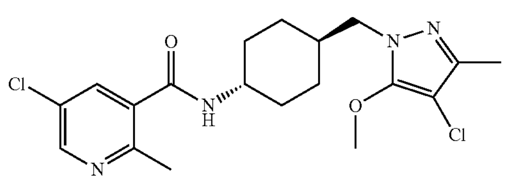 [SMILES: COc1c(Cl)c(C)nn1C[C@H]1CC[C@H](NC(=O)c2cc(Cl)cnc2C)CC1] | Trans-5-Chloro-N-[4-(4-chloro-5-methoxy-3-methyl-pyrazol-1-ylmethyl)-cyclohexyl]-2-methyl-nicotinamide | Rt 2.53 min; [M + H]⁺ 411.49 | (CDCl3, 400 MHz) δ 8.50 (1H, d), 7.61 (1H, d), 5.63 (1H, d), 4.10 (3H, s), 3.92 (1H, m), 3.73 (2H, d), 2.62 (3H, s), 2.19 (3H, s), 2.12 (2H, m), 1.86 (1H, m), 1.72 (2H, m), 1.21 (4H, m). |
| 3.8 | 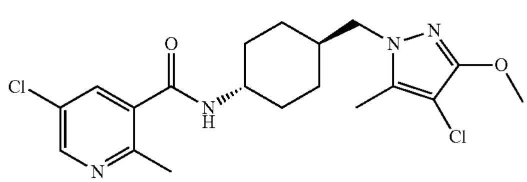 [SMILES: COc1nn(C[C@H]2CC[C@H](NC(=O)c3cc(Cl)cnc3C)CC2)c(C)c1Cl] | Trans-5-Chloro-N-[4-(4-chloro-3-methoxy-5-methyl-pyrazol-1-ylmethyl)-cyclohexyl]-2-methyl-nicotinamide | Rt 2.49 min; [M + H]⁺ | (CDCl3, 400 MHz) δ 8.50 (1H, d), 7.68 (1H, d), 5.69 (1H, d), 3.97 (4H, m), 3.75 (2H, d), 2.65 (3H, s), 2.21 (3H, s), 2.16 (2H, m), 1.90 (1H, m), 1.74 (2H, m), 1.21 (4H, m). |

TABLE 3-continued

| Ex. | Structure | Name | Retention Time (min), [M + H]+ (Method LowpH_v002) | 1H NMR |
|---|---|---|---|---|
| 3.9 | 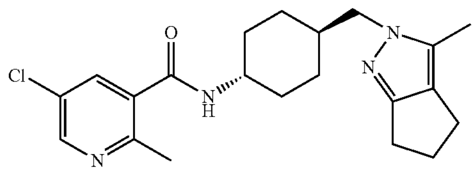 [SMILES: Cc1ncc(Cl)cc1C(=O)N[C@H]1CC[C@H](Cn2nc3c(c2C)CCC3)CC1] | Trans-5-Chloro-2-methyl-N-[4-(3-methyl-5,6-dihydro-4H-cyclopenta-pyrazol-2-ylmethyl)-cyclohexyl]-nicotinamide | Rt 2.14 min; [M + H]+ 387.46 | (400 MHz, DMSO) δ 8.52 (1H, d), 8.39 (1H, d), 7.78 (1H, d), 3.75 (2H, d), 3.66 (1H, m), 2.47 (3H, s) 2.15 (3H, s), 1.88 (2H, m), 1.71 (1H, m), 1.59 (2H, m), 1.21 (2H, m), 1.09 (2H, m) |
| 3.10 | 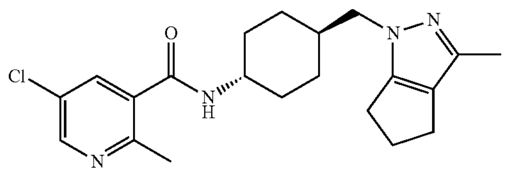 [SMILES: Cc1ncc(Cl)cc1C(=O)N[C@H]1CC[C@H](Cn2nc(C)c3c2CCC3)CC1] | Trans-5-Chloro-2-methyl-N-[4-(3-methyl-5,6-dihydro-4H-cyclopenta-pyrazol-1-ylmethyl)-cyclohexyl]-nicotinamide | Rt 2.14 min; [M + H]+ 387.46 | (400 MHz, DMSO) δ 8.52 (1H, d), 8.39 (1H, d), 7.78 (1H, d), 3.60 (2H, d), 3.65 (1H, m), 2.60 (2H, m), 2.48 (3H, s) 2.02 (3H, s), 1.89 (2H, m), 1.70 (1H, m), 1.60 (2H, m), 1.21 (2H, m), 1.05 (2H, m) |
| 3.11 | 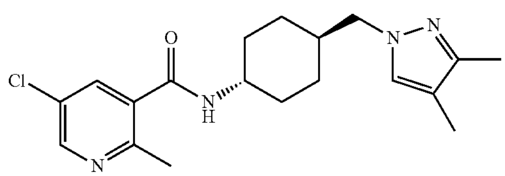 [SMILES: Cc1cn(C[C@H]2CC[C@H](NC(=O)c3cc(Cl)cnc3C)CC2)nc1C] | Trans-5-Chloro-N-[4-(3,4-dimethyl-pyrazol-1-ylmethyl)-cyclohexyl]-2-methyl-nicotinamide | Rt 2.16 min; [M + H]+ 361.36 | (CDCl3, 400 MHz) δ 8.50 (1H, d), 7.61 (1H, d), 7.08 (1H, s), 5.61 (1H, d), 3.92 (1H, m), 3.85 (2H, d), 2.61 (3H, s), 2.21 (3H, s), 2.12 (2H, m), 2.00 (3H, s), 1.91 (1H, m), 1.73 (2H, m), 1.20 (4H, m). |
| 3.12 | 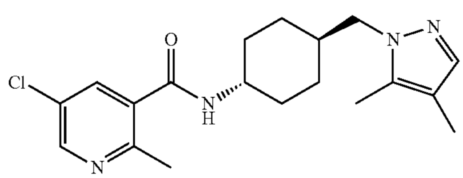 [SMILES: Cc1cnn(C[C@H]2CC[C@H](NC(=O)c3cc(Cl)cnc3C)CC2)c1C] | Trans-5-Chloro-N-[4-(4,5-dimethyl-pyrazol-1-ylmethyl)-cyclohexyl]-2-methyl-nicotinamide | Rt 2.16 min; [M + H]+ 361.36 | (CDCl3, 400 MHz) δ 8.48 (1H, d), 7.60 (1H, d), 7.25 (1H, s), 5.81 (1H, d), 3.92 (1H, m), 3.85 (2H, d), 2.60 (3H, s), 2.18 (3H, s), 2.11 (2H, m), 1.99 (3H, s), 1.90 (1H, m), 1.72 (2H, m), 1.20 (4H, m). |
| 3.13 | 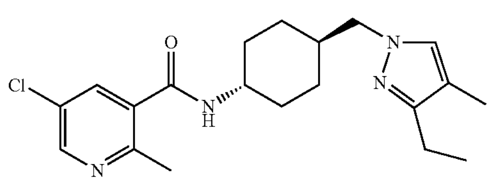 [SMILES: CCc1nn(C[C@H]2CC[C@H](NC(=O)c3cc(Cl)cnc3C)CC2)cc1C] | Trans-5-Chloro-N-[4-(3-ethyl-4-methyl-pyrazol-1-ylmethyl)-cyclohexyl]-2-methyl-nicotinamide | Rt 2.27 min; [M + H]+ 375.36 | (400 MHz, DMSO) δ 8.54 (1H, d), 8.49 (1H, d), 7.78 (1H, d), 7.32 (1H, s), 3.80 (2H, d), 3.66 (1H, m), 2.48 3H, s), 2.44 (2H, m), 1.92 (3H, s), 1.88 (2H, m), 1.70 (1H, m), 1.56 (2H, m), 1.21 (2H, m), 1.11 (3H, t), 1.05 (2H, m). |

TABLE 3-continued

| Ex. | Structure | Name | Retention Time (min), [M + H]+ (Method LowpH_v002) | ¹H NMR |
|---|---|---|---|---|
| 3.14 | 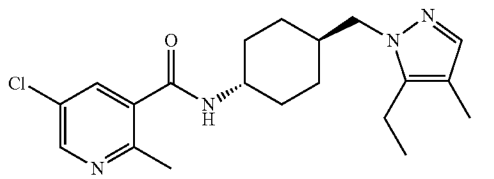 [SMILES: CCc1c(C)cnn1C[C@H]1CC[C@H](NC(=O)c2cc(Cl)cnc2C)CC1] | Trans-5-Chloro-N-[4-(5-ethyl-4-methyl-pyrazol-1-ylmethyl)-cyclohexyl]-2-methyl-nicotinamide | Rt 2.27 min; [M + H]+ 375.36 | (400 MHz, DMSO) δ 8.53 (1H, d), 8.39 (1H, d), 7.79 (1H, d), 7.13 (1H, s), 3.81 (2H, d), 3.68 (1H, m), 2.59 (2H, q), 2.47 (3H, s), 1.93 (3H, s), 1.89 (2H, m), 1.77 (1H, m), 1.56 (2H, m), 1.16 (4H, m), 1.06 (3H, t). |
| 3.15 | 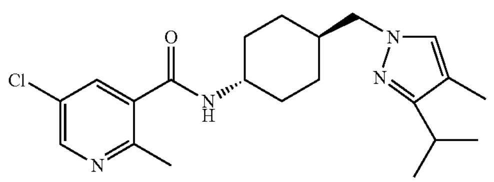 [SMILES: Cc1cn(C[C@H]2CC[C@H](NC(=O)c3cc(Cl)cnc3C)CC2)nc1C(C)C] | Trans-5-Chloro-N-[4-(3-isopropyl-4-methyl-pyrazol-1-ylmethyl)-cyclohexyl]-2-methyl-nicotinamide | Rt 2.32 min; [M + H]+ 389.41 | (400 MHz, CDCl3) δ 8.50 (1H, d), 7.62 (1H, d), 7.04 (1H, s), 5.62 (1H, d), 3.93 (1H, m), 3.88 (2H, d), 3.00 (1H, m), 2.62 (3H, s), 2.12 (2H, m), 2.05 (3H, s), 1.89 (1H, m), 1.72 (2H, m), 1.30 (6H, d), 1.12 (4H, m). |
| 3.16 | 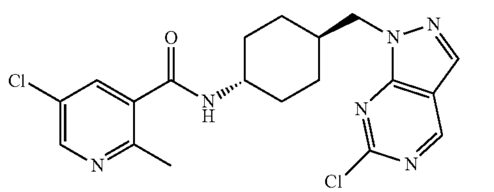 [SMILES: Cc1ncc(Cl)cc1C(=O)N[C@H]1CC[C@H](Cn2ncc3cnc(Cl)nc32)CC1] | Trans-5-Chloro-N-[4-(2-chloro-pyrrolo[2,3-d]pyrimidin-7-ylmethyl)-cyclohexyl]-2-methyl-nicotinamide | Rt 2.41 min; [M + H]+ 418.3 | (400 MHz, DMSO) δ 8.95 (1H, s), 8.55 (1H, s), 8.4 (1H, d), 7.8 (1H, s), 7.7 (1H, d), 6.7 (1H, d), 4.1 (2H, d), 3.65 (1H, m), 2.45 3H, s), 1.85 (3H, m), 1.55 (2H, m), 1.15 (4H, m). |
| 3.17 | 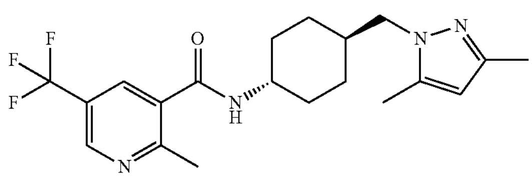 [SMILES: Cc1cc(C)n(C[C@H]2CC[C@H](NC(=O)c3cc(C(F)(F)F)cnc3C)CC2)n1] | Trans-N-[4-(3,5-Dimethyl-pyrazol-1-ylmethyl)-cyclohexyl]-2-methyl-5-trifluoromethyl-nicotinamide | Rt 2.14 min; [M + H]+ 395.34 | (400 MHz, DMSO) δ 8.89 (1H, d), 8.49 (1H, d), 8.01 (1H, d), 5.78 (1H, s), 3.78 (2H, d), 3.70 (1H, m), 2.59 (3H, s), 2.19 (3H, s), 2.08 (3H, s), 1.91 (2H, m), 1.72 (1H, m), 1.59 (2H, m), 1.16 (4H, m). |

EXAMPLE 4.1

Trans-2-Chloro-N-{4-[3-(4-methoxy-phenyl)-5-methyl-pyrazol-1-ylmethyl]-cyclohexyl}-5-trifluoromethyl-benzamide

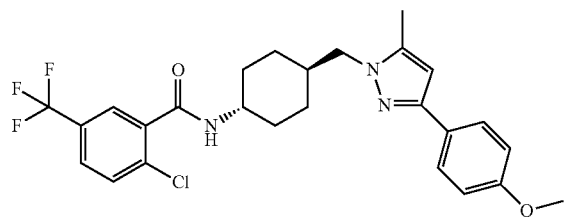 [SMILES: COc1ccc(-c2cc(C)n(C[C@H]3CC[C@H](NC(=O)c4cc(C(F)(F)F)ccc4Cl)CC3)n2)cc1]

5-(4-Methoxyphenyl)-3-methyl-1H-pyrazole (91 mg, 0.483 mmol) was dissolved in dry DMF (2 ml). The flask was flushed with $N_2$ and the solution was treated with NaH (BO % in mineral oil) (19.33 mg, 0.483 mmol) and stirred at RT for ~10 mins. Trans-methanesulfonic acid 4-(2-chloro-5-trifluoromethyl-benzoylamino)-cyclohexylmethyl ester (Intermediate G) (100 mg, 0.242 mmol) was added and the mixture was heated to 50° C. for 4 hours. After cooling to RT, the mixture was diluted with EtOAc/$H_2O$ (20 ml) and transferred to a separating funnel. The organic layer was separated and washed with brine, dried ($MgSO_4$) and concentrated in vacuo to give a brown oil. Purification of the crude product by chromatography on silica eluting with EtOAc/iso-Hexane afforded the title compound as a white solid; LCMS Rt=1.39 min, [M+H]$^+$ 506.3; Method 2 minLC__30_v002. 1H NMR (400 MHz, CDCl$_3$) δ 7.9 (1H, s), 7.7 (1H, d), 7.6 (1H, d), 7.55 (1H, d), 6.95 (2H, d), 6.25 (1H, s), 5.95 (1H, d), 4.0 (1H, m), 3.95 (2H, d), 3.85 (3H, s), 2.3 (3H, s), 2.2 (2H, d), 2.1 (1H, m), 1.8 (2H, d), 1.25 (4H, m).

The compounds of the following tabulated Examples (Table 4) were prepared by a similar method to that of Example 4.1 from trans-methanesulfonic acid 4-(2-chloro-5-trifluoromethyl-benzoylamino)-cyclohexylmethyl ester (Intermediate G) or Trans-methanesulfonic acid 4-[(5-chloro-2-methyl-pyridine-3-carbonyl)-amino]-cyclohexyl methyl ester (Intermediate F) (the preparations of which are described in the 'Preparation of Intermediates' section) and the appropriate pyrazole.

TABLE 4

| Ex. | Structure | Name | Retention Time (min), [M + H]$^+$ (Method LowpH_v002) (Unless otherwise specified) | $^1$H NMR |
|---|---|---|---|---|
| 4.2 | 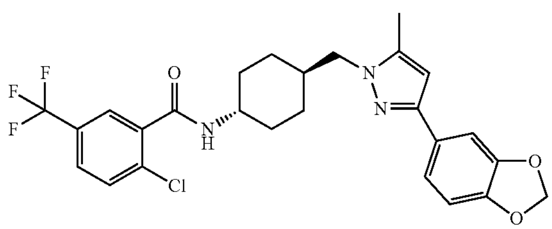 [SMILES: Cc1cc(-c2ccc3c(c2)OCO3)nn1C[C@H]1CC[C@H](NC(=O)c2cc(C(F)(F)F)ccc2Cl)CC1] | Trans-N-[4-(3-Benzo[1,3]dioxol-5-yl-5-methyl-pyrazol-1-ylmethyl)-cyclohexyl]-2-chloro-5-trifluoromethyl-benzamde | Rt 1.39 min [M + H]$^+$ 520.3 (Method 2 minLC_v002) | (400 MHz, CDCl3) 7.9 (1H, s), 7.7 (1H, d), 7.6 (1H, d), 7.55 (1H, d), 6.95 (2H, d), 6.25 (1H, s), 5.95 (1H, d), 4.0 (1H, m), 3.95 (2H, d), 3.85 (3H, s), 2.3 (3H, s), 2.2 (2H, d), 2.1 (1H, m), 1.8 (2H, d), 1.25 (4H, m). |
| 4.3 | 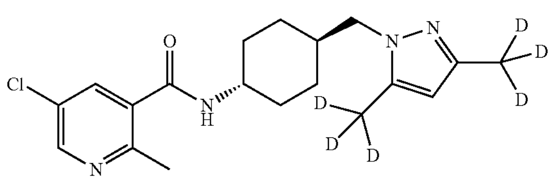 [SMILES: [2H]C([2H])([2H])c1cc(C([2H])([2H])[2H])n(C[C@H]2CC[C@H](NC(=O)c3cc(Cl)cnc3C)CC2)n1] | Trans-5-Chloro-N-[4-(3,5-d$_6$-dimethyl-pyrazol-1-ylmethyl)-cyclohexyl]-2-methyl-nicotinamide | Rt 1.99 min [M + H]$^+$ 367.4 | (400 MHz, CDCl3) δ 7.9 (1H, s), 7.6 (1H, d), 7.55 (1H, d), 7.3 (2H, m), 6.85 (1H, d), 6.25 (1H, s), 5,95 (3H, m), 4.0 (1H, m), 3.95 (2H, d), 2.3 (3H, s), 2.2 (2H, br), 2.1 (1H, m), 1.8 (2H, br), 1.25 (4H, m). |
| 4.4 | 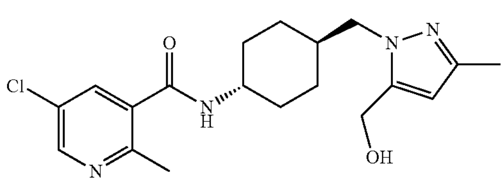 [SMILES: Cc1cc(CO)n(C[C@H]2CC[C@H](NC(=O)c3cc(Cl)cnc3C)CC2)n1] | Trans-5-Chloro-N-[4-(5-hydroxymethyl-3-methyl-pyrazol-1-ylmethyl)-cyclohexyl]-2-methyl-nicotinamide | Rt 1.99 min [M + H]$^+$ 377.27 | (400 MHz, DMSO) δ 8.54 (1H, d), 8.39 (1H, br d), 7.79 (1H, d), 5.76 (1H, s), 3.75 (2H, d), 3.68 (1H, m), 2.47 (3H, s), 1.89 (2H, m), 1.73 (1H, m), 1.58 (2H, m), 1.15 (4H, m). |

TABLE 4-continued

| Ex. | Structure | Name | Retention Time (min), [M + H]+ (Method LowpH_v002) (Unless otherwise specified) | 1H NMR |
|---|---|---|---|---|
| 4.5 | 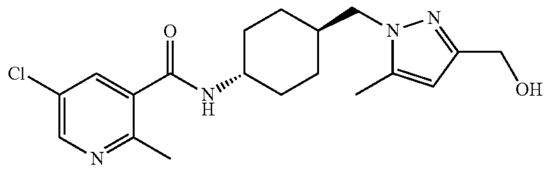 [SMILES: Cc1ncc(Cl)cc1C(=O)N[C@H]1CC[C@H](Cn2nc(CO)cc2C)CC1] | Trans-5-Chloro-N-[4-(3-hydroxymethyl-5-methyl-pyrazol-1-ylmethyl)-cyclohexyl]-2-methyl-nicotinamide | Rt 2.06 min [M + H]+ 377.28 | (400 MHz, DMSO) δ 8.52 (1H, d), 8.40 (1H, d), 7.80 (1H, d), 5.90 (1H, s), 5.18 (1H, t), 4.41 (2H, d), 3.82 (2H, d), 3.67 (1H, m), 2.47 (3H, s), 2.10 (3H, s), 1.89 (2H, m), 1.80 (1H, m), 1.59 (2H, m), 1.13 (4H, m). |
| 4.6 | 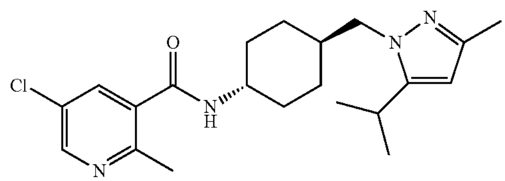 [SMILES: Cc1cc(C(C)C)n(C[C@H]2CC[C@H](NC(=O)c3cc(Cl)cnc3C)CC2)n1] | Trans-5-Chloro-N-[4-(5-isopropyl-3-methyl-pyrazol-1-ylmethyl)-cyclohexyl]-2-methyl-nicotinamide | Rt 2.24 min [M + H]+ 389.31 | (400 MHz, DMSO) δ 8.53 (1H, d), 8.38 (1H, d), 7.79 (1H, d), 5.79 (1H, s), 3.78 (2H, d), 3.68 (1H, m), 2.95 (1H, sept), 2.47 (3H, s), 2.08 (3H, s), 1.89 (2H, m), 1.77 (1H, m), 1.58 (2H, m), 1,17 (4H, m) 1.16 (6H, d), |
| 4.7 | 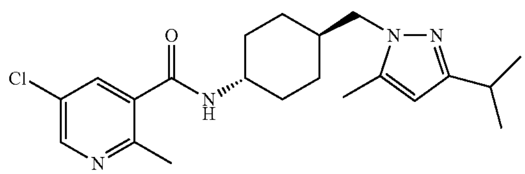 [SMILES: Cc1ncc(Cl)cc1C(=O)N[C@H]1CC[C@H](Cn2nc(C(C)C)cc2C)CC1] | Trans-5-Chloro-N-[4-(3-isopropyl-5-methyl-pyrazol-1-ylmethyl)-cyclohexyl]-2-methyl-nicotinamide | Rt 2.29 min [M + H]+ 389.32 | (400 MHz, DMSO) δ 8.53 (1H, d), 8.38 (1H, d), 7.79 (1H, d), 5.80 (1H, s), 3.76 (2H, d), 3.67 (1H, m), 2.78 (1H, sept), 2.47 (3H, s), 2.19 (3H, s), 1.89 (2H, m), 1.73 (1H, m), 1.58 (2H, m), 1.19 (4H, m) 1.14 (6H, d), |
| 4.8 | 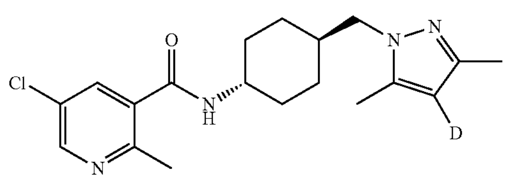 [SMILES: [2H]c1c(C)nn(C[C@H]2CC[C@H](NC(=O)c3cc(Cl)cnc3C)CC2)c1C] | Trans-5-Chloro-N-[4-(4-deutero-3,5-dimethyl-pyrazol-1-ylmethyl)-cyclohexyl]-2-methyl-nicotinamide | Rt 2.14 min [M + H]+ 362.26 | (400 MHz, DMSO) δ 8.52 (1H, d), 8.40 (1H, d), 7.79 (1H, d), 3.75 (2H, d), 3.68 (1H, m), 2.47 (3H, s), 2.18 (3H, s), 2.08 (3H, s), 1.89 (2H, m), 1.72 (1H, m), 1.58 (2H, m), 1.20 (2H, m), 1.10 (2H, m). |

EXAMPLE 5.1

Trans-2-Chloro-N-[4-(3,5-diethyl-pyrazol-1-ylmethyl)-cyclohexyl]-5-trifluoro methyl-benzamide

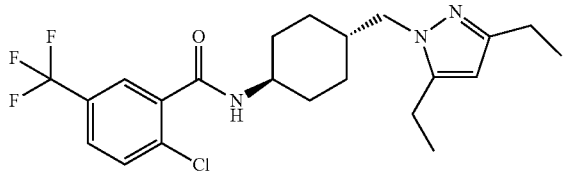 [SMILES: CCc1cc(CC)n(C[C@H]2CC[C@H](NC(=O)c3cc(C(F)(F)F)ccc3Cl)CC2)n1]

3,5-Diethyl-1H-pyrazole (26.5 mg, 0.20 mmol) in acetonitrile (2 ml) was treated with NaH (60% in oil)) (9 mg, 0.22 mmol) and the reaction mixture was stirred at RT for 10 minutes. Trans-(4-(2-chloro-5-(trifluoromethyl)benzamido)cyclohexyl)methyl trifluoro methanesulfonate (Intermediate I) (100 mg, 0.20 mmol) was added and the mixture was stirred at RT for 1 hour. The solvent was removed in vacuo and the reaction mixture was partitioned between DCM and sat. NaHCO₃. The organic phase was passed through a phase separator and the solvent was removed in vacuo. The product was purified by chromatography on silica eluting with isohexane→EtOAc to afford the title compound; LCMS Rt=2.59 min; [M+H]+ 442.51. Method LowpH_v002 1H NMR (d6-DMSO, 400 MHz) δ 8.48 (1H, d), 7.80 (1H, m), 7.72 (2H, m), 3.75 (2H, d), 3.69 (1H, m), 2.10 (3H, s), 2.01 (3H, s), 1.90 (2H, m), 1.82 (3H, s), 1.70 (1H, m), 1.58 (2H, m), 1.20 (2H, m), 1.10 (2H, m).

The compounds of the following tabulated Examples (Table 5) were prepared by a similar method to that of Example 5.1 from trans-(4-(2-chloro-5-(trifluoromethyl)benzamido)cyclohexyl)methyl trifluoro methanesulfonate (Intermediate I) and the appropriate pyrazole.

TABLE 5

| Ex. | Structure | Name | Retention Time (min), [M + H]⁺ (Method LowpH_v002 Unless otherwise specified | ¹H NMR |
|---|---|---|---|---|
| 5.2 | 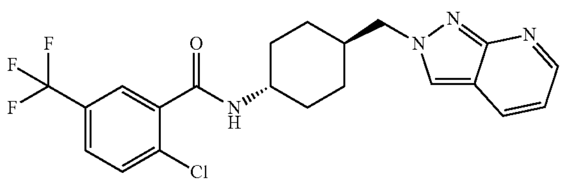 [SMILES: O=C(N[C@H]1CC[C@H](Cn2cc3cccnc3n2)CC1)c1cc(C(F)(F)F)ccc1Cl] | Trans-2-Chloro-N-(4-pyrazolo[3,4-b]pyridin-2-ylmethyl-cyclohexyl)-5-trifluoromethyl-benzamide | Rt 1.26 min [M + H]⁺ 437.3 Method 2 minLC_v002 | (400 MHz, CDCl3): δ 1.2-1.4 (4H, m), 1.7-2.4 (m) 4.00 (1H, m), 4.38 (2H, d), 6.02 (2H, d), 7.23 (1H, dd), 7.53 (1H, d), 7.61 (1H, d), 7.88 (1H, s), 7.93 (1H, s), 8.10 (1H, d), 8.85 (1H, dd) |
| 5.3 | 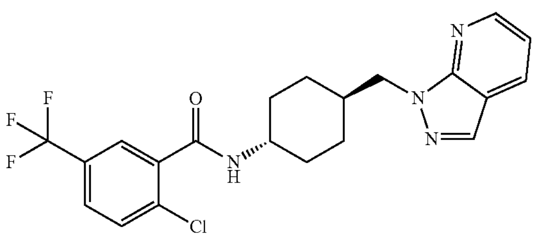 [SMILES: O=C(N[C@H]1CC[C@H](Cn2ncc3cccnc32)CC1)c1cc(C(F)(F)F)ccc1Cl] | Trans-2-Chloro-N-(4-pyrazolo[3,4-b]pyridln-1-ylmethyl-cyclohexyl)-5-trifluoromethyl-benzamide | Rt 1.61 min [M + H]⁺ Method 2 minLC__v002 | (400 MHz, CDCl3): δ 1.2-1.4 (4H, m), 1.75 (2H, m), 2.15 (3H, m), 4.0 (1H, m), 4.50 (2H, d), 5.95 (2H, d), 7.22 (1H, dd), 7.55 (1H, d), 7.63 (1H, d), 7.90 (1H, s), 8.08 (1H, s), 8.19 (1H, d), 8.59 (1H, dd) |
| 5.4 | 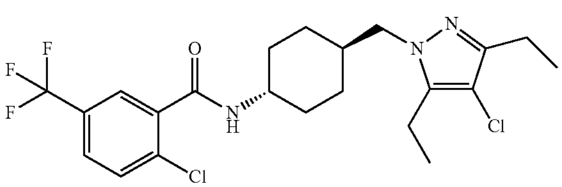 [SMILES: CCc1nn(C[C@H]2CC[C@H](NC(=O)c3cc(C(F)(F)F)ccc3Cl)CC2)c(CC)c1Cl] | Trans-2-Chloro-N-[4-(4-chloro-3,5-diethyl-pyrazol-1-ylmethyl)-cyclohexyl]-5-trifluoromethyl-benzamide | Rt 2.80 min [M + H]⁺ 475.52 | (d6-DMSO, 400 MHz) δ 8.49 (1H, d), 7.81 (1H, m), 7.72 (2H, m), 3.83 (2H, d), 3.69 (1H, m), 2.63 (2H, q), 2.50 (2H, m), 1.90 (2H, m), 1.77 (1H, m), 1.56 (2H, m), 1.17 (10H, m). |
| 5.5 | 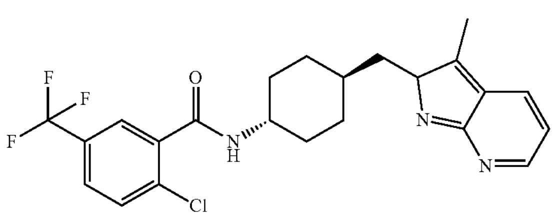 [SMILES: CC1=c2cccnc2=NC1C[C@H]1CC[C@H](NC(=O)c2cc(C(F)(F)F)ccc2Cl)CC1] | Trans-2-Chloro-N-[4-(3-methyl-pyrazolo[3,4-b]pyridin-2-ylmethyl)-cyclohexyl]-5-trifluoromethyl-benzamide | Rt 1.23 min [M + H]⁺ 451.3 Method 2 minLC_v002 | (400 MHz, CDCl3) δ 8.52 (1H, s), 7.94 (1H, d), 7.83 (1H, s), 7.55 (1H, d), 7.48 (1H, d), 6.95 (1H, m), 6.67 (1H, br), 4.22 (2H, d), 4.00 (1H, m), 2.53 (3H, s), 2.29 (1H, m), 2.15 (2H, d), 1.75 (2H, d), 1.31 (4H, m) |

TABLE 5-continued

| Ex. | Structure | Name | Retention Time (min), [M + H]+ (Method LowpH_v002 (Unless otherwise specified | ¹H NMR |
|---|---|---|---|---|
| 5.6 | 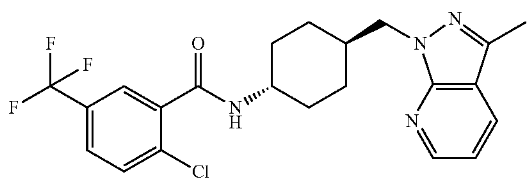 [SMILES: Cc1nn(C[C@H]2CC[C@H](NC(=O)c3cc(C(F)(F)F)ccc3Cl)CC2)c2ncccc12] | Trans-2-Chloro-N-[4-(3-methyl-pyrazolo[3,4-b]pyridin-1-ylmethyl)-cyclohexyl]-5-trifluoromethyl-benzamide | Rt 1.50 min [M + H]+ 451.2 Method 2 minLC_v002 | (400 MHz, CDCl3) δ 8.56 (1H, m), 8.13 (1H, d), 7.90 (1H, s), 7.61 (1H, d), 7.53 (1H, d), 7.19 (1H, m), 5.93 (1H, d), 4.46 (2H, d), 3.99 (1H, m), 2.63 (3H, s), 2.16 (3H, m), 1.78 (2H, d), 1.28 (4H, m) |
| 5.7 | 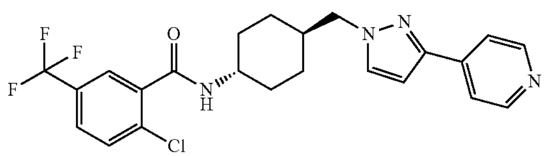 [SMILES: O=C(N[C@H]1CC[C@H](Cn2ccc(-c3ccncc3)n2)CC1)c1cc(C(F)(F)F)ccc1Cl] | Trans-2-Chloro-N-[4-(3-Pyridin-4-yl-pyrazol-1-ylmethyl)-cyclohexyl]-5-trifluoromethyl-benzamide | Rt 1.23 min [M + H]+ 463.3 Method 2 minLC_ v002 | (d6-DMSO, 400 MHz) δ 8.78 (2H, d), 8.18 (2H, d), 7.91 (1H, s), 7.64 (1H, d), 7.55 (2H, m), 6.85 (1H, s), 6.02 (1H, d), 4.11(2H, d), 4.01 (1H, m), 2.22 (2H, m), 2.04 (1H, m) 1.80 (2H, m), 1.28 (4H, m) |
| 5.8 | 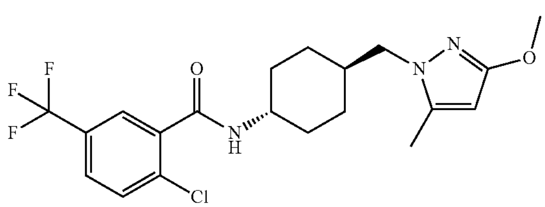 [SMILES: COc1cc(C)n(C[C@H]2CC[C@H](NC(=O)c3cc(C(F)(F)F)ccc3Cl)CC2)n1] | Trans-2-Chloro-N-[4-(3-methoxy-5-methyl-pyrazol-1-ylmethyl)-cyclohexyl]-5-trifluoromethyl-benzamide | Rt 2.55 min [M + H]+ 430.61 | (d6-DMSO, 400 MHz) δ 8.49 (1H, d), 7.80 (IH, m), 7.72 (2H, m), 5.42 (1H, s), 3.70 (6H, m), 2.18 (3H, s), 1.91 (2H, m), 1.62 (1H, m), 1.59 (2H, m), 1.20 (2H, m), 1.11 (2H, m). |
| 5.9 | 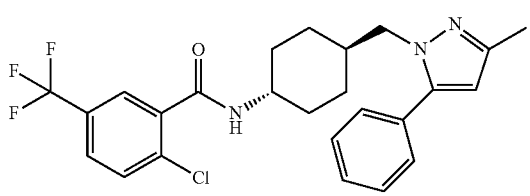 [SMILES: Cc1cc(-c2ccccc2)n(C[C@H]2CC[C@H](NC(=O)c3cc(C(F)(F)F)ccc3Cl)CC2)n1] | Trans-2-Chloro-N-[4-(3-methyl-5-phenyl-pyrazol-1-ylmethyl)-cyclohexyl]-5-trifluoromethyl-benzamide | Rt 2.72 min [M + H]+ 476.58 | (d6-DMSO, 400 MHz) δ 8.43 (1H, d), 7.80 (1H, m), 7.71 (2H, m), 7.50 (2H, m), 7.42 (3H, m), 6.11 (1H, s), 3.89 (2H, d), 3.59 (1H, m), 2.20 (3H, s), 1.82 (2H, m), 1.71 (1H, m), 1.50 (2H, m), 1.13 (2H, m), 0.90 (2H, m). |
| 5.10 | 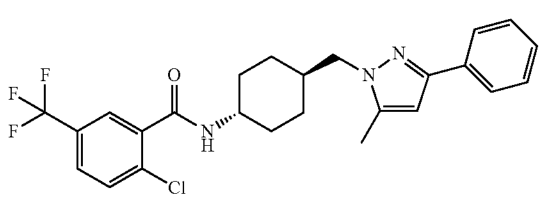 [SMILES: Cc1cc(-c2ccccc2)nn1C[C@H]1CC[C@H](NC(=O)c2cc(C(F)(F)F)ccc2Cl)CC1] | Trans-2-Chloro-N-[4-(5-methyl-3-phenyl-pyrazol-1-ylmethyl)-cyclohexyl]-5-trifluoromethyl-benzamide | Rt 2.72 min [M + H]+ 476.59 | (d6-DMSO, 400 MHz) δ 8.50 1H, d), 7.80 (1H, m), 7.72 (4H, m) , 7.38 (2H, m), 7.27 (1H, m), 6.45 (1H, s), 3.91 (2H, d), 3.70 (1H, m), 2.30 (3H, s), 1.92 (2H, m), 1.81 (1H, m), 1.63 (2H, m), 1.20 (4H, m). |

TABLE 5-continued

| Ex. | Structure | Name | Retention Time (min), [M + H]+ (Method LowpH_v002 (Unless otherwise specified | 1H NMR |
|---|---|---|---|---|
| 5.11 | 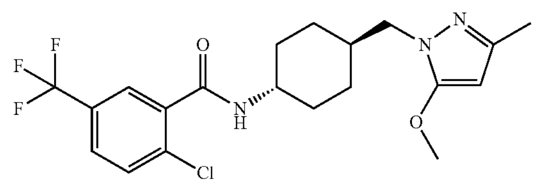 [SMILES: COc1cc(C)nn1C[C@H]1CC[C@H](NC(=O)c2cc(C(F)(F)F)ccc2Cl)CC1] | Trans-2-Chloro-N-[4-(5-methoxy-3-methyl-pyrazol-1-ylmethyl)-cyclohexyl]-5-trifluoromethyl-benzamide | Rt 2.43 min [M + H]+ 430.62 | (d6-DMSO, 400 MHz) δ 8.49 (1H, d), 7.80 (1H, m), 7.72 (2H, m), 5.44 (1H, s), 3.80 (3H, s), 3.68 (1H, m), 3.62 (2H, d), 2.07 (3H, s), 1.90 (2H, m), 1.67 (1H, m), 1.58 (2H, m), 1.20 (2H, m), 1.09 (2H, m). |
| 5.12 | 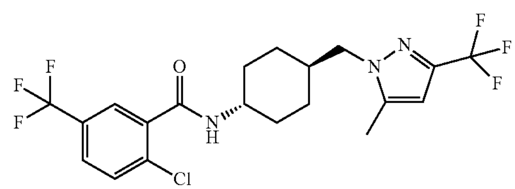 [SMILES: Cc1cc(C(F)(F)F)nn1C[C@H]1CC[C@H](NC(=O)c2cc(C(F)(F)F)ccc2Cl)CC1] | Trans-2-Chloro-N-[4-(5-methyl-3-trifluoromethyl-[1,2,4]triazol-1-ylmethyl)-cyclohexyl]-5-trifluoromethyl-benzamide | Rt 2.54 min [M + H]+ 469.5 | (400 MHz, CDCl3) δ 7.86 (1H, d), 7.59 (1H, dd), 7.51 (1H, d), 6.06 (1H, br d), 3.96 (3H, d overlapping m), 2.50 (3H, s), 2.18 (2H, m), 2.00 (1H, m), 1.75 (2H, m), 1.25 (4H, m). |
| 5.13 | 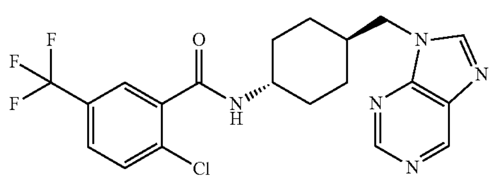 [SMILES: O=C(N[C@H]1CC[C@H](Cn2cnc3cncnc32)CC1)c1cc(C(F)(F)F)ccc1Cl] | Trans-2-Chloro-N-(4-purin-9-ylmethyl-cyclohexyl)-5-trifluoromethyl-benzamide | Rt 1.30 min [M + H]+ 438.3 Method 2 minLC_v002 | (400 MHz, CDCl3) δ 9.21 (1H, s), 9.05 (1H, s), 8.13 (1H, s), 7.90 (1H, s), 7.62 (1H, d), 7.54 (1H, d), 5.99 (1H, d), 4.22 (2H, d), 4.01 (1H, m), 2.22 (2H, d), 2.07 (1H, m), 1.81 (2H, d), 1.32 (4H, m) |
| 5.14 | 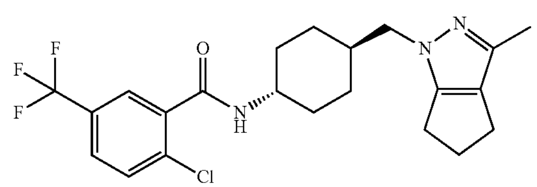 [SMILES: Cc1nn(C[C@H]2CC[C@H](NC(=O)c3cc(C(F)(F)F)ccc3Cl)CC2)c2c1CCC2] | Trans-2-Chloro-N-[4-(3-methyl-5,6-dihydro-4H-cyclopentapyrazol-1-ylmethyl)-cyclohexyl]-5-trifluoromethyl-benzamide | Rt 2.28 min [M + H]+ 440.51 | (d6-DMSO, 400 MHz) δ 8.50 (1H, d), 7.80 (1H, m), 7.72 (2H, m), 3.79 (2H, d), 3.68 (1H, m), 2.67 (2H, m), 2.47 (4H, m), 2.09 (3H, s), 1.90 (2H, m), 1.71 (1H, m), 1.60 (2H, m), 1.21 (2H, m), 1.09 (2H, m). |
| 5.15 | 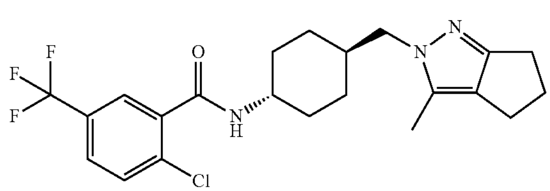 [SMILES: Cc1c2c(nn1C[C@H]1CC[C@H](NC(=O)c3cc(C(F)(F)F)ccc3Cl)CC1)CCC2] | Trans-2-Chloro-N-[4-(3-methyl-5,6-dihydro-4H-cyclopentapyrazol-2-ylmethyl)-cyclohexyl]-5-trifluoromethyl-benzamide | Rt 2.44 min [M + H]+ 440.52 | (d6-DMSO, 400 MHz) δ 8.50 (1H, d), 7.80 (1H, m), 7.72 (2H, m), 3.79 (2H, d), 3.70 (1H, m), 2.53 (2H, m), 2.48 (2H, m), 2.30 (2H, m), 2.15 (3H, s), 1.91 (2H, m), 1.72 (1H, m), 1.60 (2H, m), 1.21 (2H, m), 1.11 (2H, m). |

TABLE 5-continued

| Ex. | Structure | Name | Retention Time (min), [M + H]+ (Method LowpH_v002 (Unless otherwise specified | 1H NMR |
|---|---|---|---|---|
| 5.16 | 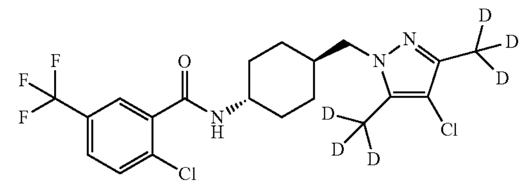 [SMILES: [2H]C([2H])([2H])c1nn(C[C@H]2CC[C@H](NC(=O)c3cc(C(F)(F)F)ccc3Cl)CC2)c(C([2H])([2H])[2H])c1Cl] | Trans-2-Chloro-N-[4-(4-chloro-3,5-d6-dimethyl-pyrazol-1-ylmethyl)-cyclohexyl]-5-trifluoromethyl-benzamide | Rt 2.69 min [M + H]+ 454.44 | (d6-DMSO, 400 MHz) δ 8.50 (1H, d), 7.80 (1H, m), 7.72 (2H, m), 3.82 (2H, d), 3.70 (1H, m), 1.91 (2H, m), 1.72 (1H, m), 1.58 (2H, m), 1.18 (4H, m). |
| 5.17 | 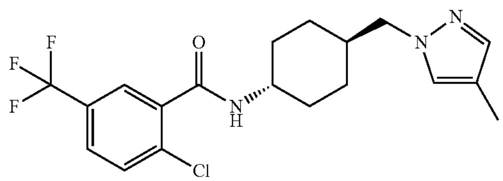 [SMILES: Cc1cnn(C[C@H]2CC[C@H](NC(=O)c3cc(C(F)(F)F)ccc3Cl)CC2)c1] | Trans-2-Chloro-N-[4-(4-methyl-pyrazol-1-ylmethyl)-cyclohexyl]-5-trifluoromethyl-benzamide | Rt 2.53 min [M + H]+ 400.4 | (400 MHz, DMSO-d6). δ 8.5 (1H, d), 7.8 (1H, d), 7.7 (2H, d), 7. (1H, s), 7.2 (1H, s), 3.9 (2H, d), 3.7 (1H, m), 2.0 (3H, s), 1.9 (2H, d), 1.7 (1H, m), 1.5 (2H, d), 1.2 (2H, m), 1.1 (2H, m). |
| 5.18 | 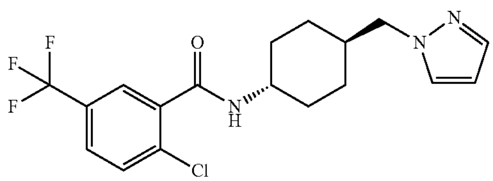 [SMILES: O=C(N[C@H]1CC[C@H](Cn2cccn2)CC1)c1cc(C(F)(F)F)ccc1Cl] | Trans-2-Chloro-N-(4-pyrazol-1-ylmethyl-cyclohexyl)-5-trifluoromethyl-benzamide | Rt 2.48 min [M + H]+ 386.3 | (400 MHz, CDCl3). δ 7.9 (1H, s), 7.6 (2H, d), 7.5 (1H, d), 6.3 (1H, s), 6.0 (1H, d), 4.1 (2H, d), 4.0 (1H, m), 2.2 (2H, d), 2.0 (1H, m), 1.7 (2H, d), 1.2 (4H, m). |
| 5.19 | 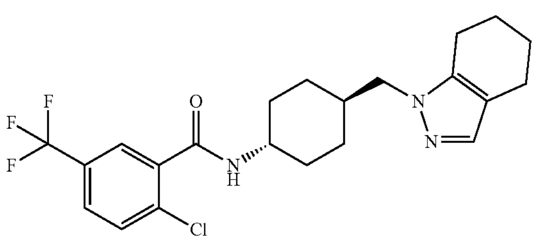 [SMILES: O=C(N[C@H]1CC[C@H](Cn2ncc3c2CCCC3)CC1)c1cc(C(F)(F)F)ccc1Cl] | Trans-2-Chloro-N-[4-(4,5,6,7-tetrahydro-indazol-1-ylmethyl)-cyclohexyl]-5-trifluoromethyl-benzamide | Rt 2.55 min [M + H]+ 440.5 | (400 MHz, CDCl3) δ 7.86 (1H, d), 7.59 (1H, dd), 7.51 (1H, d), 7.01 (1H, s), 5.98 (1H, br d), 3.96 (1H, m), 3.86 (2H, d), 2.66 (2H, t), 2.52 (2H, t), 2.15 (2H, m), 1.89 (1H, m), 1.85-1.68 (6H, m), 1.20 (4H, m). |
| 5.20 | 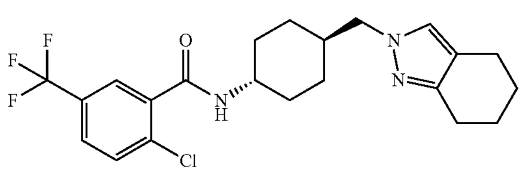 [SMILES: O=C(N[C@H]1CC[C@H](Cn2cc3c(n2)CCCC3)CC1)c1cc(C(F)(F)F)ccc1Cl] | Trans-2-Chloro-N-[4-(4,5,6,7-tetrahydro-indazol-2-ylmethyl)-cyclohexyl]-5-trifluoromethyl-benzamide | Rt 2.56 min [M + H]+ 440.5 | (400 MHz, CDCl3) δ 7.87 (1H, d), 7.57 (1H, dd), 7.51 (1H, d), 7.25 (1H, s), 6.00 (1H, br d), 3.96 (1H, m), 3.81 (2H, d), 2.54 (2H, t), 2.50 (2H, t), 2.15 (2H, m), 1.95 (1H, m), 1.82 (2H, m), 1.72 (4H, m), 1.21 (4H, m). |
| 5.21 | 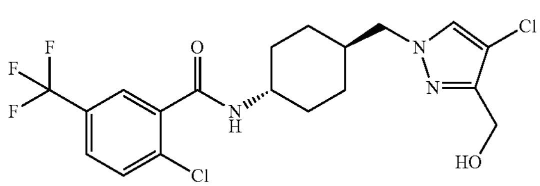 [SMILES: O=C(N[C@H]1CC[C@H](Cn2cc(Cl)c(CO)n2)CC1)c1cc(C(F)(F)F)ccc1Cl] | Trans-2-Chloro-N-[4-(4-chloro-3-hydroxymethyl-pyrazol-1-ylmethyl)-cyclohexyl]-5-trifluoromethyl-benzamide | Rt 2.47 min [M + H]+ 450.5 | (400 MHz, DMSO-d6). δ 8.5 (1H, d), 7.9 (1H, s), 7.8 (1H, d), 7.7 (2H, d), 5.0 (1H, s), 4.4 (2H, s), 3.9 (2H, d), 3.7 (1H, m), 1.9 (2H, d), 1.7 (1H, m), 1.6 (2H, d), 1.2 (2H, m), 1.1 (2H, m). |

TABLE 5-continued

| Ex. | Structure | Name | Retention Time (min), [M + H]+ (Method LowpH_v002 (Unless otherwise specified | 1H NMR |
|---|---|---|---|---|
| 5.22 | 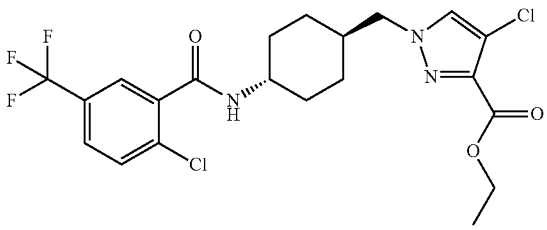 [SMILES: CCOC(=O)c1nn(C[C@H]2CC[C@H](NC(=O)c3cc(C(F)(F)F)ccc3Cl)CC2)cc1Cl] | Trans-4-Chloro-1-[4-(2-chloro-5-trifluoromethyl-benzoylamino)-cyclohexylmethyl]-1H-pyrazole-3-carboxylic acid ethyl ester | Rt 2.59 min [M + H]+ 492.4 | (400 MHz, MeOD). δ 7.9 (1H, s), 7.7 (3H, m), 4.4 (2H, q), 4.1 (2H, d), 3.8 (1H, m), 2.1 (2H, d), 1.9 (1H, m), 1.7 (2H, d), 1.4 (5H, m), 1.2 (2H, m). |
| 5.23 | 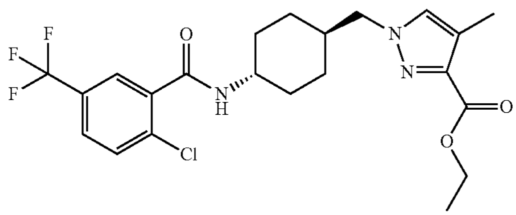 [SMILES: CCOC(=O)c1nn(C[C@H]2CC[C@H](NC(=O)c3cc(C(F)(F)F)ccc3Cl)CC2)cc1C] | Trans-1-[4-(2-Chloro-5-trifluoromethyl-benzoylamino)-cyclohexylmethyl]-4-methyl-1H-pyrazole-3-carboxylic acid ethyl ester | Rt 2.59 min [M + H]+ 472.51 | (400 MHz, MeOD). δ 7.7 (3H, m), 7.5 (1H, s), 4.4 (2H, q), 4.0 (2H, d), 3.8 (1H, m), 2.3 (3H, s), 2.1 (2H, d), 1.9 (1H, m), 1.7 (2H, d), 1.4 (5H, m), 1.2 (2H, m). |
| 5.24 | 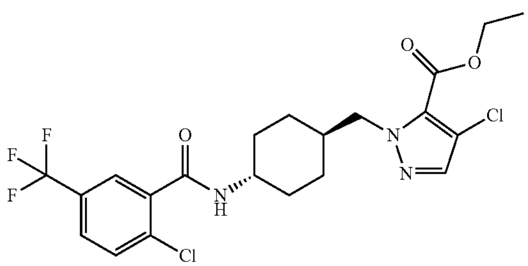 | Trans-4-Chloro-2-[4-(2-chloro-5-trifluoromethyl-benzoylamino)-cyclohexylmethyl]-2H-pyrazole-3-carboxylic acid ethyl ester | Rt 2.67 min [M + H]+ 472.5 | (400 MHz, MeOD). δ 7.9 (1H, s), 7.7 (3H, m), 4.4 (2H, q), 4.1 (2H, d), 3.8 (1H, m), 2.1 (2H, d), 1.9 (1H, m), 1.7 (2H, d), 1.4 (5H, m), 1.2 (2H, m). |
| 5.25 | 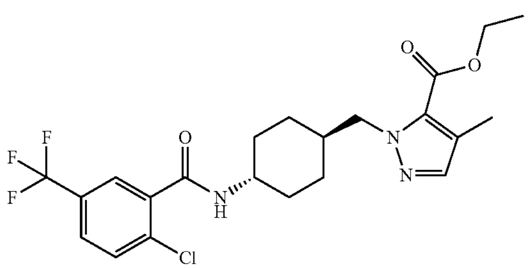 | Trans-2-[4-(2-Chloro-5-trifluoromethyl-benzoylamino)-cyclohexylmethyl]-4-methyl-2H-pyrazole-3-carboxylic acid ethyl ester | Rt 2.71 min [M + H]+ 492.3 | (400 MHz, MeOD). δ 7.7 (3H, m), 7.4 (1H, s), 6.9 (1H, s), 4.4 (4H, m), 3.7 (1H, m), 2.3 (3H, s), 2.1 (2H, d), 1.9 (1H, m), 1.6 (2H, d), 1.4 (3H, t), 1.2 (4H, m). |
| 5.26 | 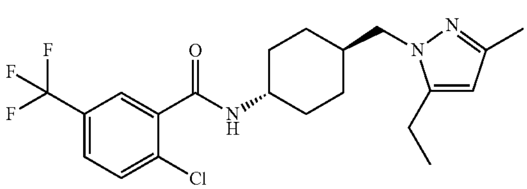 | Trans-2-Chloro-N-[4-(5-ethyl-3-methyl-pyrazol-1-ylmethyl)-cyclohexyl]-5-trifluoromethyl-benzamide | Rt 2.44 min [M + H]+ 428.61 | (d6-DMSO, 400 MHz) δ 8.49 (1H, d), 7.80 (1H, m), 7.72 (2H, m), 5.80 (1H, s), 3.75 (2H, d), 3.70 (1H, ni), 2.53 (2H, q), 2.09 (3H, s), 1.90 (2H, m), 1.73 (1H, m), 1.56 (2H, m), 1.13 (7H, m). |

TABLE 5-continued

| Ex. | Structure | Name | Retention Time (min), [M + H]+ (Method LowpH_v002 (Unless otherwise specified | ¹H NMR |
|---|---|---|---|---|
| 5.27 | 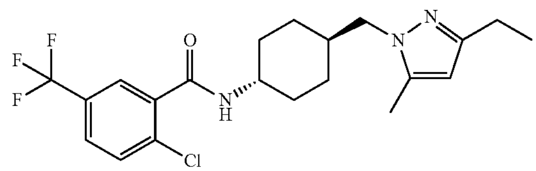 [SMILES: CCc1cc(C)n(C[C@H]2CC[C@H](NC(=O)c3cc(C(F)(F)F)ccc3Cl)CC2)n1] | Trans-2-Chloro-N-[4-(3-ethyl-5-methyl-pyrazol-1-ylmethyl)-cyclohexyl]-5-trifluoromethyl-benzamide | Rt 2.43 min [M + H]+ 428.61 | (d6-DMSO, 400 MHz) δ 8.49 (1H, d), 7.80 (1H, m), 7.72 (2H, m), 5.80 (1H, s), 3.75 (2H, d), 3.68 (1H, m), 2.45 (2H, q), 2.19 (3H, s), 1.90 (2H, m), 1.72 (1H, m), 1.57 (2H, m), 1.20 (2H, m), 1.10 (5H, m). |
| 5.28 | 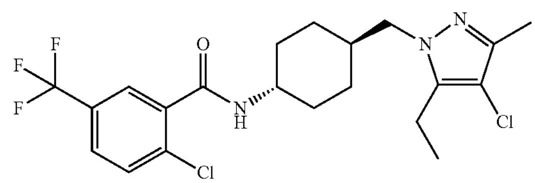 [SMILES: CCc1c(Cl)c(C)nn1C[C@H]1CC[C@H](NC(=O)c2cc(C(F)(F)F)ccc2Cl)CC1] | Trans-2-Chloro-N-[4-(4-chloro-5-ethyl-3-methyl-pyrazol-1-ylmethyl)-cyclohexyl]-5-trifluoromethyl-benzamide | Rt 2.69 min [M + H]+ 462.53 | (d6-DMSO, 400 MHz) δ 8.49 (1H, d), 7.80 (1H, m), 7.72 (2H, m), 3.82 (2H, d), 3.69 (1H, m), 2.62 (2H, q), 2.09 (3H, s), 1.90 (2H, m), 1.77 (1H, m), 1.55 (2H, m), 1.18 (2H, m), (1.10 (5H, m). |
| 5.29 | 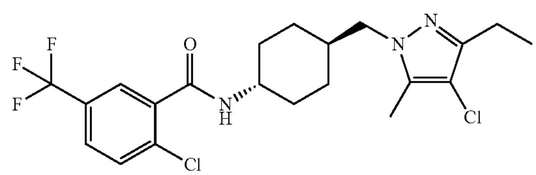 [SMILES: CCc1nn(C[C@H]2CC[C@H](NC(=O)c3cc(C(F)(F)F)ccc3Cl)CC2)c(C)c1Cl] | Trans-2-Chloro-N-[4-(4-chloro-3-ethyl-5-methyl-pyrazol-1-ylmethyl)-cyclohexyl]-5-trifluoromethyl-benzamide | Rt 2.69 min [M + H]+ 462.52 | (d6-DMSO, 400 MHz) δ 8.49 (1H, d), 7.80 (1H, m), 7.72 (2H, m), 3.82 (2H, d), 3.68 (1H, m), 2.50 (2H, q), 2.20 (3H, s), 1.90 (2H, m), 1.72 (1H, m), 1.56 (2H, m), 1.20 (2H, m), 1.12 (5H, m). |
| 5.30 | 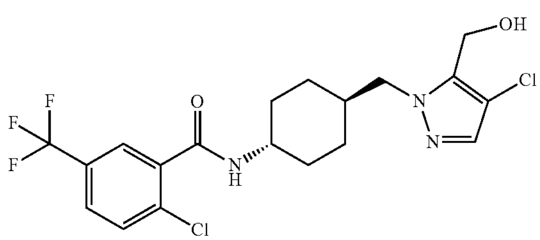 [SMILES: O=C(N[C@H]1CC[C@H](Cn2ncc(Cl)c2CO)CC1)c1cc(C(F)(F)F)ccc1Cl] | Trans-2-Chloro-N-[4-(4-chloro-5-hydroxymethyl-pyrazol-1-ylmethyl)-cyclohexyl]-5-trifluoromethyl-benzamide | Rt 250 min [M + H]+ 450.4 | (400 MHz, MeOD). δ 7.7 (3H, m), 7.4 (1H, s), 4.6 (2H, s), 4.1 (2H, d), 3.8 (1H, m), 2.1 (2H, d), 2.0 (1H, m), 1.7 (2H, d), 1.3 (4H, m). |
| 5.31 | 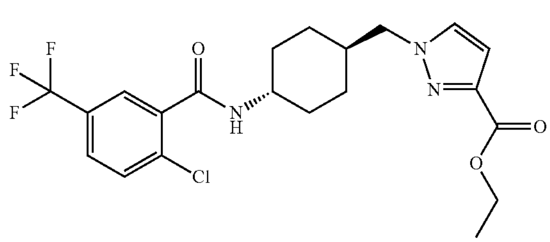 [SMILES: CCOC(=O)c1ccn(C[C@H]2CC[C@H](NC(=O)c3cc(C(F)(F)F)ccc3Cl)CC2)n1] | Trans-1-[4-(2-Chloro-5-trifluoromethyl-benzoylamino)-cyclohexylmethyl]-1H-pyrazole-3-carboxylic acid ethyl ester | Rt 2.48 min [M +H]+ 458.3 | (400 MHz, MeOD). δ 7.6 (4H, m), 6.7 (1H, s), 4,2 (2H, q), 4.0 (2H, d), 3.7 (1 H, m), 2.0 (2H, d), 1.3 (1H, m) , 1.6 (2H, d), 1.3 (3H, t), 1.2 (2H, m), 1.1 (2H, m). |

TABLE 5-continued

| Ex. | Structure | Name | Retention Time (min), [M + H]+ (Method LowpH_v002 (Unless otherwise specified | 1H NMR |
|---|---|---|---|---|
| 5.32 | 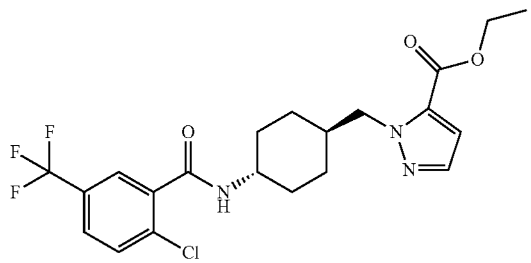 [SMILES: CCOC(=O)c1ccnn1C[C@H]1CC[C@H](NC(=O)c2cc(C(F)(F)F)ccc2Cl)CC1] | Trans-2-[4-(2-Chloro-5-trifluoromethyl-benzoylamino)-cyclohexylmethyl]-2H-pyrazole-3-carboxylic acid ethyl ester | Rt 2.63 min [M + H]+ 458.5 | (400 MHz, MeOD). δ 7.7 (3H, m), 7.5 (1H, s), 6.9 (1H, s), 4.5 (2H, d), 4.4 (2H, q), 3.8 (1H, m), 2.1 (2H, d), 1.9 (1H, m), 1.6 (2H, d), 1.4 (3H, t), 1.2 (4H, m). |
| 5.33 | 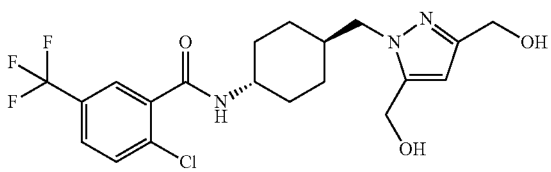 [SMILES: O=C(N[C@H]1CC[C@H](Cn2nc(CO)cc2CO)CC1)c1cc(C(F)(F)F)ccc1Cl] | Trans-N-[4-(3,5-Bis-hydroxymethyl-pyrazol-1-ylmethyl)-cyclohexyl]-2-chloro-5-trifluoromethyl-benzamide | Rt 2.22 min [M + H]+ 446.42 | (d6-DMSO, 400 MHz) δ 8.49 (1H, d), 7.80 (1H, m), 7.72 (2H, m), 6.10 (1H, s), 5.21 (1H, t), 4.91 (1H, t) 4.48 (2H, d), 4.33 (2H, d), 3.88 (2H, d), 3.69 (1H, m), 1.90 (2H, m), 1.80 (1H, m), 1.60 (2H, m), 1.15 (4H, m). |
| 5.34 | 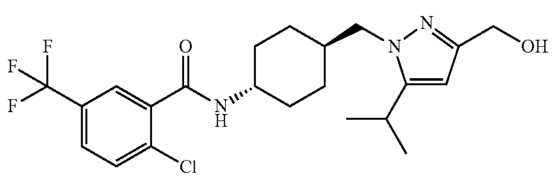 [SMILES: CC(C)c1cc(CO)nn1C[C@H]1CC[C@H](NC(=O)c2cc(C(F)(F)F)ccc2Cl)CC1] | Trans-2-Chloro-N-[4-(3-hydroxymethyl-5-isopropyl-pyrazol-1-ylmethyl)-cyclohexyl]-5-trifluoromethyl-benzamide | Rt 2.64 min [M + H]+ 458.48 | (d6-DMSO, 400 MHz) δ 8.49 (1H, d), 7.80 (1H, m), 7.72 (2H, m), 5.98 (1H, s), 4.88 (1H, t), 4.32 (2H, d), 3.81 (2H, d), 3.69 (1H, m), 1.91 (2H, m), 1.79 (1H, m), 1.59 (2H, m), 1.19 (6H, d), 1.12 (4H, m). |
| 5.35 | 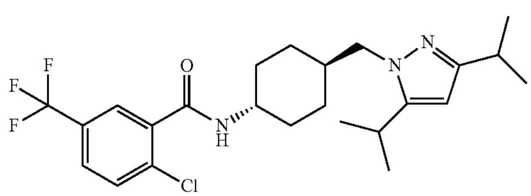 [SMILES: CC(C)c1cc(C(C)C)n(C[C@H]2CC[C@H](NC(=O)c3cc(C(F)(F)F)ccc3Cl)CC2)n1] | Trans-2-Chloro-N-[4-(3,5-diisopropyl-pyrazol-1-ylmethyl)-cyclohexyl]-5-trifluoromethyl-benzamide | Rt 2.55 min [M + H]+ 470.48 | (d6-DMSO, 400 MHz) δ 8.48 (1H, d), 7.80 (1H, d), 7.75 (1H, s), 7.71 (1H, d), 5.83 (1H, s), 3.79 (2H, d), 2.95 (1H, m), 2.78 (1H, m), 1.90 (4H, m), 1.78 (1H, m), 1.58 (4H, m), 1.17 (12H, m) |
| 5.36 | 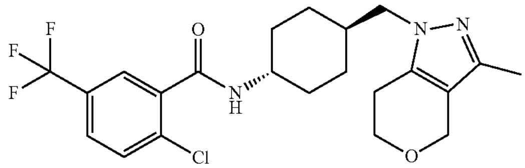 [SMILES: Cc1nn(C[C@H]2CC[C@H](NC(=O)c3cc(C(F)(F)F)ccc3Cl)CC2)c2c1COCC2] | Trans-2-Chloro-N-[4-(3-methyl-6,7-dihydro-4H-pyrano[4,3-c]pyrazol-1-ylmethyl)-cyclohexyl]-5-trifluoromethyl-benzamide | Rt 2.39 min [M + H]+ 456.58 | (d6-DMSO, 400 MHz) δ 8.50 (1H, d), 7.81 (2H, m), 7.64 (1H, d), 4.49 (2H, s), 3.79 (2H, t), 3.72 (2H, d), 3.58 (1H, m), 2.63 (2H, m), 2.01 (3H, s), 1.90 (2H, m), 1.72 (1H, m), 1.59 (2H, m), 1.21 (2H, m), 1.09 (2H, m) |

TABLE 5-continued

| Ex. | Structure | Name | Retention Time (min), [M + H]+ (Method LowpH_v002 (Unless otherwise specified | 1H NMR |
|---|---|---|---|---|
| 5.37 | 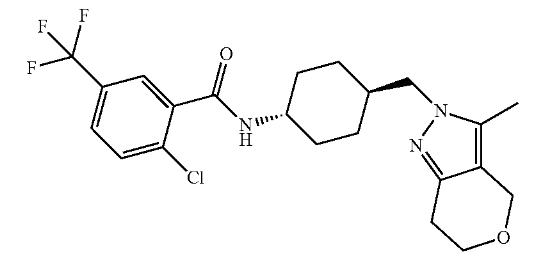 [SMILES: Cc1c2c(nn1C[C@H]1CC[C@H](NC(=O)c3cc(C(F)(F)F)ccc3Cl)CC1)CCOC2] | Trans-2-Chloro-N-[4-(3-methyl-6,7-dihydro-4H-pyrano[4,3-c]pyrazol-2-ylmethyl)-cyclohexyl]-5-trifluoromethyl-benzamide | Rt 2.39 min [M + H]+ 456.58 | (d6-DMSO, 400 MHz) δ 8.50 (1H, d), 7.81 (2H, d), 7.64 (1H, d), 4.50 (2H, s), 3.80 (2H, t), 3.79 (2H, d), 3.69 (1H, m), 2.57 (2H, m), 2.10 (3H, s), 1.91 (2H, m), 1.72 (1H, m), 1.60 (2H, m), 1.20 (2H, m), 1.10 (2H, m) |
| 5.38 | 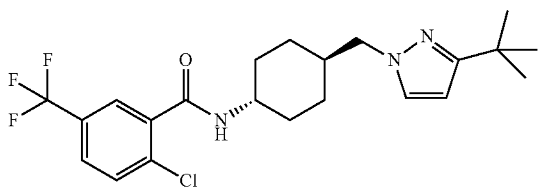 [SMILES: CC(C)(C)c1ccn(C[C@H]2CC[C@H](NC(=O)c3cc(C(F)(F)F)ccc3Cl)CC2)n1] | Trans-N-[4-(3-tert-Butyl-pyrazol-1-ylmethyl)-cyclohexyl]-2-chloro-5-trifluoromethyl-benzamide | Rt 1.34 min [M + H]+ 442.4 | (400 MHz, MeOD). δ 7.7 (3H, m), 7,4 (1H, s), 6.1 (1H, s), 3.9 (2H, d), 2.1 (2H, 1.7 (2H, d), 1.3 (11H, m), 1.2 (2H, m). |

EXAMPLE 5.21

Trans-2-Chloro-N-[4-(4-chloro-3-hydroxymethyl-pyrazol-1-ylmethyl)-cyclohexyl]-5-trifluoromethyl-benzamide

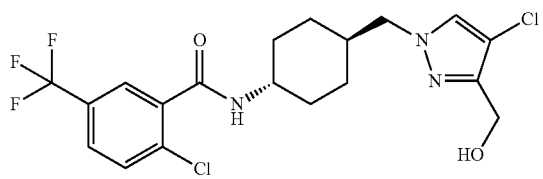 [SMILES: O=C(N[C@H]1CC[C@H](Cn2cc(Cl)c(CO)n2)CC1)c1cc(C(F)(F)F)ccc1Cl]

Step 1: Ethyl 4-chloro-1-((trans-4-(2-chloro-5-(trifluoromethyl)benzamido)cyclohexyl)methyl)-1H-pyrazole-3-carboxylate The title compound is prepared from trans-(4-(2-chloro-5-(trifluoromethyl)benzamido)cyclohexyl)methyl trifluoro methanesulfonate (Intermediate I) and 4-chloro-1H-pyrazole-3-carboxylic acid ethyl ester (prepared according to WO 2009123714 page 52-53) analogously to Example 5.1; 1H NMR (400 MHz, MeOD) δ 7.9 (1H, s), 7.7 (3H, m), 4.4 (2H, q), 4.1 (2H, d), 3.8 (1H, m), 2.1 (2H, d), 1.9 (1H, m), 1.7 (2H, d), 1.4 (5H, m), 1.2 (2H, m).

Step 2: Trans-2-Chloro-N-[4-(4-chloro-3-hydroxymethyl-pyrazol-1-ylmethyl)-cyclohexyl]-5-trifluoromethyl-benzamide A cooled (0° C.) solution of ethyl 4-chloro-1-((trans-4-(2-chloro-5-(trifluoromethyl)benzamido)cyclohexyl)methyl)-1H-pyrazole-3-carboxylate (step 1)(40 mg, 0.081 mmol) in THF (1 ml) was treated with LiAlH4 (6.1 mg, 0.162 mmol) and stirred at 0° C. After 3 h a grey suspension formed. The reaction was quenched by dropwise addition water (0.1 ml in THF 5 ml), followed by 1 M NaOH (0.1 ml) and water (0.3 ml). The reaction mixture was stirred and allowed to warm to RT overnight. The resulting mixture was filtered and the filtrate was concentrated in vacuo. The crude product was triturated with Et2O to afford the title compound as a white solid; 1H NMR (400 MHz, DMSO-d6) δ 8.5 (1H, d), 7.9 (1H, s), 7.8 (1H, d), 7.7 (2H, d), 5.0 (1H, s), 4.4 (2H, s), 3.9 (2H, d), 3.7 (1H, m), 1.9 (2H, d), 1.7 (1H, m), 1.6 (2H, d), 1.2 (2H, m), 1.1 (2H, m). LC-MS: Rt 2.47 mins; MS m/z 450.5 [M+H]+; Method LowpH_v002.

Preparation of Intermediates

Intermediate A

Trans-tert-butyl 4-(hydroxymethyl)cyclohexylcarbamate

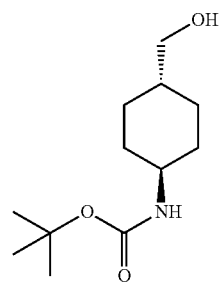 [SMILES: CC(C)(C)OC(=O)N[C@H]1CC[C@H](CO)CC1]

Step 1: Methyl trans-4-(tert-butoxycarbonylamino)cyclohexanecarboxylate

Methyl trans-4-aminocyclohexanecarboxylate (43 g, 222 mmol) was added to MeOH (500 ml) to give a colourless solution. The solution was cooled to 10° C. and triethylamine (46.4 ml, 333 mmol) was added dropwise, followed by a solution of di-tert-butyldicarbonate (53.3 g, 244 mmoL) in MeOH (400 ml) over 20 minutes. The reaction was warmed to room temperature and stirred at room temperature overnight. The mixture was evaporated to dryness under reduced pressure. The resulting colourless solid was dissolved in EtOAc (1000 ml) and the solution obtained was washed successively with 10% citric acid solution (100 ml), saturated sodium bicarbonate solution (2×100 ml) and saturated brine (100 ml), dried (MgSO₄) and evaporated under reduced pressure to give a colourless solid.

Step 2: Trans-tert-butyl 4-(hydroxymethyl)cyclohexylcarbamate

Methyl trans-4-(tert-butoxycarbonylamino)cyclohexanecarboxylate (55.5 g, 216 mmol) was suspended in ethanol (900 ml) and THF (100 ml) and the mixture was cooled to 5° C. Granular calcium chloride (47.9 g, 431 mmol) was added portionwise to give a milky suspension. Sodium borohydride (32.6 g, 863 mmol) was added portionwise over 25 mins at 5° C. The reaction mixture (white emulsion) was stirred at 5° C. for 1 hour, the water bath was removed and then the reaction mixture was allowed to warm to room temperature and stirred at room temperature overnight. The reaction mixture was cooled to 10° C. and 5% potassium carbonate (200 ml) was added dropwise until the pH of the solution was pH11. A colourless precipitate formed which was filtered off. The solid was stirred with ethyl acetate (2000 ml) and water (500 ml). The organic layer was separated and washed with 0.5M HCl (200 ml), then washed with water (2×200 ml) and saturated brine (100 ml). The organic solution was dried over anhydrous MgSO₄, filtered and evaporated to give a white solid. The solid was dried under high vacuum overnight to constant weight; [M+H]+230.

Intermediate B

Trans-4-(3,5-diethyl-pyrazol-1-ylmethyl)-cyclohexylamine

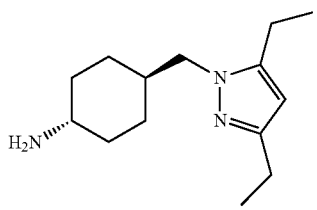 [SMILES: CCc1cc(CC)n(C[C@H]2CC[C@H](N)CC2)n1]

Step 1: Trans-trifluoro-methanesulfonic acid 4-tert-butoxycarbonylamino-cyclohexylmethyl ester Trans-tert-butyl 4-(hydroxymethyl)cyclohexylcarbamate (Intermediate A) (1.00 g, 4.36 mmol) was placed in a flask with DCM (50 ml) and pyridine (0.41 g, 5.23 mmol). The reaction mixture was cooled to 0° C. and then triflic anhydride (1.35 g, 4.80 mmol) was added dropwise. The reaction mixture was stirred at 0° C. for 1 hour and then partitioned between DCM and sat. ammonium chloride. The organic phase was dried over MgSO4, filtered and the solvent was removed in vacuo on an ice-cold water bath to give a beige solid. The product was purified by chromatography on silica eluting with iso-hexane/EtOAc to afford the title compound; ¹H NMR (d6-DMSO, 400 MHz) δ 6.72 (1H, d), 4.09 (2H, d), 3.03 (1H, m), 1.80 (2H, m), 1.70 (2H, m), 1.59 (1H, m), 1.38 (9H, s), 1.12 (2H, m), 1.01 (2H, m).

Step 2: Trans-[4-(3,5-Diethyl-pyrazol-1-ylmethyl)-cyclohexyl]-carbamic acid tert-butyl ester 3,5-Diethyl-1H-pyrazole (34.4 mg, 0.28 mmol) was placed in a vial with MeCN (2 ml). NaH (60% in oil)) (12.2 mg, 0.30 mmol) was added and the reaction mixture was stirred at RT for 10 minutes. Trans-trifluoro-methanesulfonic acid 4-tert-butoxy carbonyl amino-cyclohexylmethyl ester (100 mg, 0.28 mmol) was added and the mixture was stirred at RT for 1 hour. The solvent was removed in vacuo and the reaction mixture was partitioned between DCM and water. The organic phase was passed through a phase separator and the solvent was removed in vacuo. The product was purified by chromatography on silica eluting iso-hexane/EtOAc to afford the title compound; 1H NMR (d6-DMSO, 400 MHz) δ 6.65 (1H, d), 5.80 (1H, s), 3.71 (2H, d), 3.13 (1H, m), 2.50 (4H, m), 1.74 (2H, m), 1.64 (1H, m), 1.50 (2H, m), 1.35 (9H, s), 1.11 (6H, m), 1.02 (4H, m).

Step 3: Trans-4-(3,5-Diethyl-pyrazol-1-ylmethyl)-cyclohexylamine hydrochloride Trans-[4-(3,5-Diethyl-pyrazol-1-ylmethyl)-cyclohexyl]-carbamic acid tert-butyl ester (80 mg, 0.24 mmol) was dissolved in MeOH (1 ml). 4M HCl/dioxan (1 ml) was added and the RM was stirred at RT for 2 hours. The solvent was removed in vacuo to afford the title product which was used without further purification; LC-MS Rt 1.59 mins [M+H]+ 236.

Intermediate BB

Trans-(4-Amino-cyclohexyl methyl)-(3-chloro-6-methoxy-pyridin-2-yl)-amine

Step 1: N-(3-chloro-6-methoxypyridin-2-yl)-2,2,2-trifluoroacetamide

3-Chloro-6-methoxy-pyridin-2-ylamine (commercial) (500 mg, 3.15 mmol) in dry THF (20 ml) and pyridine (374 mg, 4.73 mmol) cooled to 0° C. was treated with dropwise with trifluoroacetic anhydride (728 mg, 3.47 mmol). The reaction mixture was stirred at 0° C. for 1 hour and concentrated in vacuo. The mixture was partitioned between DCM and water. The organic phase was washed with water and brine, dried over MgSO4, filtered and the solvent was removed in vacuo. Purification by chromatography on silica eluting with EtOAc/iso-hexane afforded the title compound; 1H NMR (d6-DMSO, 400 MHz) δ 11.84 (1H, s), 7.98 (1H, d), 6.94 (1H, d), 3.87 (3H, s).

Step 2: (4-Amino-cyclohexylmethyl)-(3-chloro-6-methoxy-pyridin-2-yl)-amine

This compound is prepared from N-(3-chloro-6-methoxy-pyridin-2-yl)-2,2,2-trifluoroacetamide (Int. BB step 1) and trans-trifluoro-methanesulfonic acid 4-tert-butoxycarbonylamino-cyclohexylmethyl ester (Int. B step 1) analogously to Intermediate B step 2 and 3; 1H NMR (d6-DMSO, 400 MHz) δ 7.86 (3H, br), 7.42 (1H, d), 6.48 (1H, t), 5.91 (1H, d), 3.77

(3H, s), 3.21 (2H, t), 2.92 (1H, m), 1.94 (2H, m), 1.78 (2H, m), 1.59 (1H, m), 1.28 (2H, m), 1.01 (2H, m).

Pyrazolo methylcyclohexylamines

Pyrazolo methylcyclohexylamines used to synthesis final compounds were prepared analogously to Intermediate B by replacing 3,5-diethyl-1H-pyrazole (step 2) with the appropriate pyrazole. The pyazoles were either commercially available of were prepared according to, or a combination of, the following methods from the appropriate commercially available starting materials:

Pyrazole A

4-Chloro-3,5-d$_6$-dimethyl-1H-pyrazole

Step 1: d$_6$-Pentane-2,4-dione

Pentane-2,4-dione (10.00 g, 100 mmol) and potassium carbonate (1.00 g, 7.25 mmol) were placed in a flask with deuterium oxide (50 ml) and the reaction mixture was heated at 120° C. for 18 hours. The product was extracted into Et$_2$O, dried over MgSO$_4$ and the solvent was removed in vacuo (no heat, 300 mbar). The resulting product was deuterated again using the same above set of conditions to yield the title compound which was used in the next step without further purification.

Step 2: 3,5-d$_6$-Dimethyl-1H-pyrazole d$_8$-Pentane-2,4-dione (1.50 g, 13.9 mmol) was dissolved in MeOH (10 ml). Hydrazine monohydrate (1.04 g, 20.8 mmol) was added and the reaction mixture was stirred at RT for 1 hour. The solvent was removed in vacuo and the crude product was dissolved in DCM, dried (MgSO$_4$), filtered and concentrated in vacuo to afford the title compound; 1H NMR (d6-DMSO, 400 MHz) 12.00 (1H, br), 5.72 (1H, s).

Step 3: 4-Chloro-3,5-d$_6$-dimethyl-1H-pyrazole 3,5-d$_6$-Dimethyl-1H-pyrazole (500 mg, 4.89 mmol) was dissolved in chloroform (10 ml). N-Chlorosuccinimide (653 mg, 4.89 mmol) was added and the reaction mixture was stirred at RT for 1 hour. The mixture was partitioned between chloroform and water. The organic phase was washed with water, brine, dried (MgSO$_4$), filtered and the solvent was removed in vacuo to afford the title compound which was used without further purification.

Pyrazole B

5-Methyl-4-pyridin-3-yl-1H-pyrazol-3-ylamine

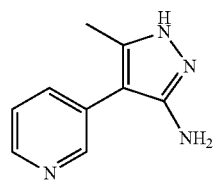

Step 1: 3-Oxo-2-pyridin-3-yl-butyronitrile 2-(Pyridin-3-yl)acetonitrile (7.00 g, 59.3 mmol) was dissolved in THF (100 ml). NaH (60% in oil) (5.93 g, 148 mmol) was slowly added and the reaction mixture was stirred at RT for 1 hour (continuous gentle gas evolution). EtOAc (1 ml) was added and the mixture was stirred until an exothermic reaction occurred. EtOAc (7 mL) was then added slowly to maintain gentle heating. The reaction was stirred at RT for 2 hours and then approximately 75% of the THF was removed in vacuo. The resulting mixture was partitioned between Et$_2$O and water and the aqueous phase was washed with Et$_2$O (2×50 mL). The aqueous phase was then acidified with 1M HCl and the product was extracted into EtOAc. A significant amount of solid gradually formed between the two layers. This material was filtered off and dried.

The organic phase was washed with water and brine, dried (MgSO$_4$) filtered and the solvent was removed in vacuo. The filtered and extracted material were combined to afford the title compound which was used in the next step without further purification; 1H NMR (d6-DMSO, 400 MHz) δ 13.00 (1H, br), 9.03 (1H, s), 8.30 (1H, m, 8.03 (1H, m), 7.49 (1H, m), 2.29 (3H, s). LCMS Rt=0.81 mins; [M+H]$^+$161 Method LowpH_v002.

Step 2:
5-Methyl-4-pyridin-3-yl-1H-pyrazol-3-ylamine

3-Oxo-2-pyridin-3-yl-butyronitrile (step 1) (1.00 g, 6.49 mmol) was dissolved in EtOH (10 ml) and water (2 ml). Hydrazine hydrobromide (2.82 g, 24.97 mmol) was added and the reaction mixture was heated at reflux for 1 hour. The solvent was removed in vacuo and the residue was partitioned between EtOAc and sat. NaHCO$_3$. The organic phase was washed with water and brine, dried (MgSO$_4$), filtered and the solvent was removed in vacuo to afford the title compound which was used without further purification; 1H NMR (d6-DMSO, 400 MHz) δ 11.51 (1H, br), 8.60 m), 8.40 (1H, m), 7.72 (1 h, m), 7.39 (1H, m), 4.60 (2H, br), 2.19 (3H, s).

Pyrazole C 4-(2-Chloro-4-methoxy-phenyl)-5-methyl-1H-pyrazol-3-ylamine

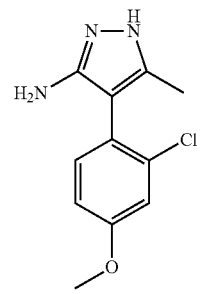 [SMILES: COc1ccc(-c2c(N)n[nH]c2C)c(Cl)c1]

Acetic acid (1.3 ml, 22.36 mmol) was added to a stirred suspension of 2-(2-chloro-4-methoxyphenyl)-3-oxobutane-nitrile (2.0 g, 8.94 mmol) and hydrazine hydrate (0.65 ml, 13.41 mmol) in dry toluene (25 ml). The reaction mixture was heated at reflux for 20 h. The solvent was removed in vacuo and the residue was partitioned between 2M HCl and EtOAc. The organic extract was extracted several times with 2M HCl then discarded. The acidic extract was neutralised with NaHCO$_3$ then re-extracted 3× with EtOAc. The combined organic extracts were dried (MgSO$_4$) and the solvent removed to give the title compound as a viscous gum. No further purification was carried out; LCMS: Rt 1.19 mins; [M+H]$^+$ 238.1 1H NMR (400 MHz, d6-DMSO) δ 1.95 (3H, s), 3.80 (3H, s), 4.1 (2H, br m), 6.92 (1H, s), 7.10 (1H, s), 7.20 (1H, d).

Pyrazole D 3-(5-Methyl-2H-pyrazol-3-yl)-pyridine

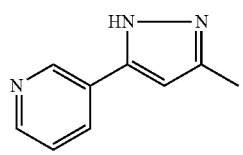

Step 1: 1-Pyridin-3-yl-butane-1,3-dione

A cooled (0° C.) solution of ethyl nicotinate (3.00 g, 2.71 ml, 19.65 mmol) in THF (10 ml) was treated with sodium hydride (60%, 1.572 g, 39.3 mmol) followed by the dropwise addition of a solution of acetone (2.282 g, 39.3 mmol, 2.89 ml) in THF (10 ml). The mixture was heated at reflux for 3 hours and then allowed to cool to RT. The mixture was acidified to ~pH5 with 2M HCl and partitioned between EtOAc and water. The organic phase was separated and washed with water, brine, dried (MgSO4) filtered and the solvent was removed in vacuo. Purification by chromatography on silica eluting with iso-hexane/EtOAc afforded the titled compound; 1H NMR (CDCl3, 400 MHz) δ 15.97 (1H, s), 9.10 (1H, s), 8.78 (1H, d), 8.22 (1H, d), 7.49 (1H, t), 6.21 (1H, s), 2.25 (3H, s). LCMS Rt=1.13 mins; [M+H]+ 164.21 Method Low-pH_v002.

Step 2: 3-(5-Methyl-2H-pyrazol-3-yl)-pyridine

1-Pyridin-3-yl-butane-1,3-dione (step 1) (500 mg, 3.06 mmol) was dissolved in MeOH (20 ml). Hydrazine monohydrate (230 mg, 223 μl, 4.60 mmol) was added and the resulting mixture was stirred at RT for 1 hour. After cooling to RT, the solvent was removed in vacuo. The crude residue was dissolved in DCM, dried over (MgSO4) filtered and concentrated in vacuo to afford the title compound which was used without further purification.

1H NMR (CDCl3, 400 MHz) δ 12.70 (1H, s), 9.96 (1H, s), 8.48 (1H, t), 8.09 (1H, t), 7.39 (1H, s), 6.56 (1H, s), 2.25 (3H, s); LCMS Rt=0.98 mins; [M+H]+161.13 Method Low-pH_v002.

Pyrazole E

4-Deutero-3,5-Dimethyl-1H-pyrazole

4-Bromo-3,5-dimethyl-1H-pyrazole (500 mg, 2.86 mmol) and zinc powder (373 mg, 5.71 mmol) were placed in a microwave vial with 20% NaOD in D2O (10 ml). The reaction mixture was stirred at 80° C. for 2 hours and then poured into 2M DCl in D2O (25 ml). The mixture was extracted with EtOAc and the combined organic extracts were washed with brine, dried (MgSO4) and the solvent was removed in vacuo. Purification of the product was by chromatography on silica eluting with iso-hexane→EtOAc afforded the title product; 1H NMR (d6-DMSO, 400 MHz) 11.97 (1H, s), 2.11 (6H, s).

Pyrazole F

4-Chloro-2H-pyrazole-3-carboxylic acid ethyl ester

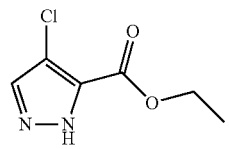

This compound was prepared according to WO 2009123714 page 52-53.

Intermediate C

5-Chloro-2-methylnicotinoyl chloride

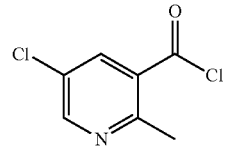

5-Chloro-2-methyl-nicotinic acid (4.15 g, 24.2 mmol) was placed in a flask with DCM (100 ml) and oxalyl chloride (3.68 g, 29 mmol). DMF (200 μl) was added and the reaction mixture was stirred at RT for 1 hour (gas evolution). The mixture was filtered and the solvent was removed in vacuo to afford the title product which was used without further purification.

Intermediate D

Trans-2-Chloro-N-(4-formyl-cyclohexyl)-5-trifluoromethyl-benzamide

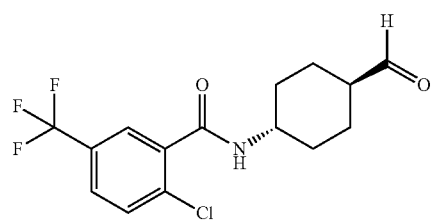 [SMILES: O=C[C@H]1CC[C@H](NC(=O)c2cc(C(F)(F)F)ccc2Cl)CC1]

Step 1: Trans-4-(2-Chloro-5-trifluoromethyl-benzoylamino)-cyclohexane carboxylic acid methyl ester

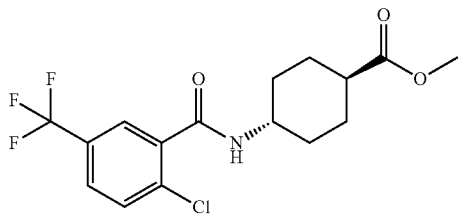 [SMILES: COC(=O)[C@H]1CC[C@H](NC(=O)c2cc(C(F)(F)F)ccc2Cl)CC1]

To a stirred suspension of trans-4-amino-cyclohexylcarboxylic acid methyl ester hydrochloride (6.7 g, 34.7 mmol) in dry THF (90 ml) under nitrogen atmosphere was added triethylamine (12 ml, 86.8 mmol). The suspension was cooled to 0° C. and 2-chloro-5-(trifluoromethyl)benzoyl chloride (8.85 g, 36.4 mmol) in dry THF (40 ml) was added dropwise over 20 minutes. The resulting thick, colourless slurry was stirred at 0-5° C. for 30 minutes and then allowed to warm to room temp and stirred at room temp for 1 hour. The reaction was quenched by the dropwise addition of water (5 ml) in THF (45 ml) to give a clear solution. This was diluted with water (100 ml) and ethyl acetate (300 ml). The biphasic mixture was stirred for 5 minutes then the organic phase was separated and washed successively with water (100 ml), saturated sodium bicarbonate (100 ml) and saturated brine (100 ml), dried (MgSO₄), filtered and evaporated to give a colourless solid; [M+H]+364.

Step 2: Trans-2-Chloro-N-(4-hydroxymethyl-cyclohexyl)-5-trifluoromethyl-benzamide

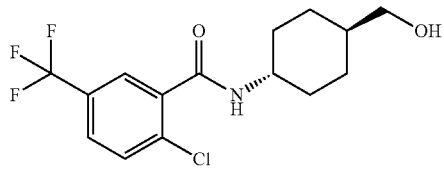 [SMILES: O=C(N[C@H]1CC[C@H](CO)CC1)c1cc(C(F)(F)F)ccc1Cl]

To a solution of trans-4-(2-chloro-5-trifluoromethyl-benzoylamino)-cyclohexane carboxylic acid methyl ester (step 1) (95.2 g, 0.26 mol) in dry THF (1000 ml) under nitrogen at 0° C. was added lithium aluminium hydride pellets (20 g, 0.53 mol) portion wise over 3 hours. The reaction mixture was stirred at 0° C. for a further 2 hours and then carefully quenched at 0° C. by the addition of water (40 ml) in THF (60 ml) followed by further THF (500 ml) to maintain a mobile suspension. Finally, 1M sodium hydroxide solution (80 ml) was added at 0° C. resulting in a yellow solution containing a colourless suspension. The reaction was filtered through a Celite® pad (filter material) to remove inorganic salts. The Celite® pad/salts were washed with EtOAc (500 ml) then with EtOAc:THF (1:1; 300 ml). The organics were combined and diluted with further EtOAc (600 ml) and then washed with saturated brine (600 ml). The organic layer was dried (Na₂SO₄), filtered and concentrated under reduced pressure until a slurry was obtained. Et₂O was added to the slurry, which was then stirred for 5 minutes before being filtered to recover a colourless solid. The solid was washed with isohexane and then dried at 35° C. under vacuum to give the required product.

Step 3: Trans-2-Chloro-N-(4-formyl-cyclohexyl)-5-trifluoromethyl-benzamide

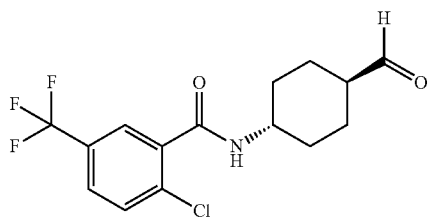 [SMILES: O=C[C@H]1CC[C@H](NC(=O)c2cc(C(F)(F)F)ccc2Cl)CC1]

To a stirred suspension of trans-2-chloro-N-(4-hydroxymethyl-cyclohexyl)-5-trifluoromethyl-benzamide (step 2) (24 g, 71.5 mmol) in DCM (72 ml) under N₂ at RT, was added triethylamine (29.7 ml, 214 mmol) followed by DMSO (24 ml), giving an almost homogenous solution. The mixture was cooled to 0° C. (ice/salt bath), and to this was added dropwise a solution/suspension of sulfur trioxide-pyridine complex (34.1 g, 214 mmol) in DMSO (30 ml): DCM (20 ml) over a period of ~90 min. The mixture was stirred at 0-5° C. over a 1 h period then allowed to warm to RT over 2 h. The mixture was cooled to 0° C. in an ice bath and was quenched by the addition of 1 M HCl (aq) (40 ml) dropwise over 30 min. The mixture was then diluted with water (60 ml) and DCM (150 ml). 2 M HCl was added to give pH ~1-2. The organic phase was separated, washed again with 2 M HCl (100 ml), followed by sat. NaHCO₃ (100 ml). The organic layer was diluted with EtOAc (800 ml) and was vigourously stirred at RT. The mixture was then filtered removing some insoluble material in the process. The now clear two phase mixture was separated, the organic (EtOAc) layer was dried (MgSO₄), filtered and concentrated to give an off white solid. The crude solid was suspended in diethylether (500 ml) and triturated, removing some brown/yellow colour. The solid was allowed to settle, and the liquors were decanted off. The solid was then triturated in iso-hexane (300 ml), using the same procedure twice, then the solid was transferred to a small flask in iso-hexane slurry and was dried in vacuo to give an off-white solid; [M+H]+334

Intermediate E

Trans-5-Chloro-N-(4-formyl-cyclohexyl)-2-methyl-nicotinamide

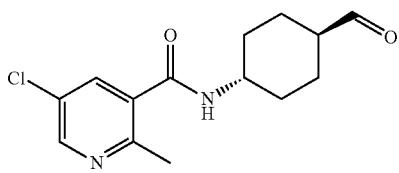 [SMILES: Cc1ncc(Cl)cc1C(=O)N[C@H]1CC[C@H](C=O)CC1]

Step 1: Trans-4-[(5-Chloro-2-methyl-pyridine-3-carbonyl)-amino]-cyclohexane carboxylic acid methyl ester Trans-4-Amino-cyclohexanecarboxylic acid methyl ester (2.14 g, 11.05 mmol) was suspended in THF (50 ml) and Et₃N (2.79 g, 27.6 mmol) and cooled to 0° C. 5-Chloro-2-methylnicotinoyl chloride (Intermediate C) (2.20 g, 11.05 mmol) was slowly added portionwise and the reaction mixture was stirred at RT for 2 hours. The reaction mixture was partitioned between EtOAc and 1M HCl. The organic phase was washed with water, brine, dried over $MgSO_4$, filtered and the solvent was removed in vacuo to afford the title product which was used in the next step without further purification. $^1$H NMR (400 MHz, DMSO-$d_6$) δ 8.53 (1H, d), 7.42 (1H, 5), 7.80 (1H, d), 3.70 (1H, m), 3.60 (3H, s), 2.49 (3H, s), 2.29 (1H, m), 1.95 (4H, m), 1.42 (2H, m), 1.29 (2H, m); [M+H]+311.26.

Step 2: Trans-5-Chloro-N-(4-hydroxymethyl-cyclohexyl)-2-methyl-nicotinamide

Trans-4-[(5-Chloro-2-methyl-pyridine-3-carbonyl)-amino]-cyclohexanecarboxylic acid methyl ester (step 1) (2.20 g, 7.08 mmol) was placed in a flask with dry THF (100 ml). This was cooled to 0° C. and lithium aluminum hydride (0.537 g, 14.16 mmol) was added. The reaction mixture was stirred at RT for 2 hours and then quenched with water (0.5 ml), 2M NaOH (0.5 ml) and then water again (1.5 ml). The solids were filtered off through Celite® (filter material) and the filtrate was partitioned between EtOAc and water. The organic phase was washed with water and brine, dried over $MgSO_4$, filtered and the solvent was removed in vacuo to afford the title product which was used in the next step without further purification. $^1$H NMR (400 MHz, DMSO-$d_6$) δ 8.53 (1H, d), 8.38*1H, d), 7.79 (1H, d), 4.40 (1H, t), 3.66 (1H, m), 3.21 (2H, t), 2.47 (3H, s), 1.92 (2H, m), 1.78 (2H, m), 1.31 (1H, m), 1.22 (2H, m), 0.98 (2H, m). [M+H]+283.30.

Step 3: Trans-5-Chloro-N-(4-formyl-cyclohexyl)-2-methyl-nicotinamide

This compound was prepared from trans-5-Chloro-N-(4-hydroxymethyl-cyclohexyl)-2-methyl-nicotinamide analogously to Intermediate D; 1H NMR (d6-DMSO, 400 MHz) δ 9.60 (1H, s), 8.56 (1H, d), 8.45 (1H, d), 7.81 (1H, d), 3.70 (1H, m), 2.50 (3H, s), 2.23 (1H, m), 1.98 (4H, m), 1.31 (4H, m)); LCMS Rt=1.92 min, [M+H]+281.28; Method LowpH_v002.

Intermediate F

Trans-methanesulfonic acid 4-[(5-chloro-2-methyl-pyridine-3-carbonyl)-amino]-cyclohexylmethyl ester A solution of trans-5-chloro-N-(4-hydroxymethyl-cyclohexyl)-2-methyl-nicotinamide (Intermediate E, step 2) (100 mg, 0.354 mmol) and pyridine (3.6 ml) in dry DCM (3.5 ml) under nitrogen was cooled to approx. 0° C. using an ice-water bath. Methanesulfonyl chloride (0.030 ml, 0.389 mmol) was added dropwise. The reaction mixture was allowed to warm to room temp and stirred at this temp for 4 hours. The reaction was quenched by the addition of sat. $NH_4Cl$ at room temp and then extracted with diethyl ether (3×20 ml). The $Et_2O$ extracts were combined, washed with sat brine (20 ml), dried ($MgSO_4$), filtered and evaporated to give the title compound as a colourless solid. LCMS 361.2/363.2 [M+H]+. $^1$H NMR (400 MHz, $CDCl_3$) δ 8.52 (1H, d), 7.65 (1H, d), 5.68 (1H, br d), 4.09 (2H, d), 3.96 (1H, m), 3.04 (3H, s), 2.65 (3H, s), 2.21 (2H, m), 1.96 (2H, m), 1.79 (1H, m), 1.27 (4H, m).

Intermediate G

Trans-methanesulfonic acid 4-(2-chloro-5-trifluoromethyl-benzoylamino)-cyclohexylmethyl ester Trans-2-Chloro-N-(4-hydroxymethyl-cyclohexyl)-5-trifluoromethyl-benzamide (Intermediate D, step 2) (1 g, 2.98 mmol) was suspended in DCM. THF (6 ml) was added to solubilise the alcohol. The mixture was cooled to 0° C. and treated with triethylamine (0.623 ml, 4.47 mmol) followed by dropwise addition of methanesulfonyl chloride (0.255 ml, 3.28 mmol). The reaction mixture was allowed to warm to RT stirring O/N and then diluted with DCM (50 ml). The mixture was washed with water, 1M HCl and brine. The organic portion was dried ($MgSO_4$) and reduced under vacuum to give the title compound as a white solid. 1H NMR (400 MHz, $CDCl_3$) δ 7.82 (1H, s), 7.53 (1H, d), 7.45 (1H, d), 5.91 (1H, d), 4.00 (2H, d), 3.90 (1H, m), 2.94 (3H, s), 2.14 (2H, m), 1.86 (2H, m), 1.71 (1H, m), 1.19 (4H, m).

Intermediate H

Trans-4-(5,6-Dihydro-4H-cyclopentapyrazol-1-ylmethyl)-cyclohexylamine

This compound was prepared analogously to Intermediate B by replacing 3,5-diethyl-1H-pyrazole with 2,4,5,6-tetrahydrocyclopenta[c]pyrazole; LCMS Rt=1.39 min, [M+H]+ 234.29; Method LowpH_v002.

Intermediate I

Trans-(4-(2-chloro-5-(trifluoromethyl)benzamido) cyclohexyl)methyl trifluoro methanesulfonate Trans-2-chloro-N-(4-hydroxymethyl-cyclohexyl)-5-trifluoromethyl-benzamide (Intermediate D step 2) (1.00 g, 2.98 mmol) in DCM (25 ml) was treated with pyridine (0.28 g, 3.57 mmol) and the reaction mixture was cooled to 0° C. Trifluoromethanesulfonic anhydride (0.92 g, 3.28 mmol) was added slowly and the reaction mixture was stirred at 0° C. for 1 hour. The reaction was quenched by the addition of sat. $NH_4Cl$ at 0° C. and extracted with DCM (3×10 ml). The DCM extracts were combined, washed with sat. brine (10 ml), dried (MgSO4), filtered and evaporated to afford the title compound as a pale yellow solid; $^1$H NMR (400 MHz, DMSO-$d_6$) δ 8.50 (1H, d), 7.80 (1H, m) 7.72 (2H, m), 4.11 (2H, d), 3.68 (1H, m), 1.95 (2H, m), 1.78 (2H, m), 1.65 (1H, m), 1.25 (2H, m), 1.11 (2H, m).

Intermediate J

Trans-(4-(2-chloro-5-(trifluoromethyl)benzamido) cyclohexyl)methyl 4-methyl benzenesulfonate Trans-2-chloro-N-(4-hydroxymethyl-cyclohexyl)-5-trifluoromethyl-benzamide (Intermediate D step 2) 1.00 g (2.98 mmol) was dissolved in DCM (40 ml) and pyridine (10 ml). Tosyl chloride (0.85 g, 4.47 mmol) was added and the reaction mixture was stirred at RT overnight. The mixture was partitioned between DCM and 1M HCl. The organic phase was washed with water and brine, dried over $MgSO_4$, filtered and the solvent was removed in vacuo. Trituration of the resulting solid with iso-hexane:EtOAc—4:1 afforded the title compound; $^1$H NMR (400 MHz, DMSO-$d_6$) δ 8.48 (1H, d), 7.80 (3H, m), 7.72 (2H, d), 7.49 (2H, d), 3.85 (2H, d), 3.60 (1H, m), 2.41 (3H, s), 1.89 (2H, m), 1.68 (2H, m), 1.53 (1H, m), 1.20 (2H, m), 1.00 (2H, m).

Biological Data:

TABLE 1

| Example | CRF-1 IC50 (micromolar) |
|---|---|
| 1.4 | 0.948 |
| 2.0 | 0.160 |
| 2.1 | 0.256 |
| 2.13 | 0.167 |
| 2.14 | 0.214 |
| 2.15 | 0.170 |
| 2.16 | 0.147 |
| 2.3 | 0.318 |
| 3.17 | 0.634 |
| 4.1 | 0.082 |
| 4.2 | 0.059 |
| 4.3 | 0.088 |
| 4.4 | 6.956 |
| 4.5 | 0.665 |
| 4.6 | 0.040 |
| 4.8 | 0.262 |
| 5.1 | 0.021 |
| 5.11 | 0.067 |
| 5.17 | 0.132 |
| 5.26 | 0.022 |
| 5.29 | 0.049 |
| 5.8 | 0.126 |

TABLE 2

| Example | CRF-1 IC50 (micromolar) | CRF-2 IC50 (micromolar) |
|---|---|---|
| 1.1 | 0.134 | 4.878 |
| 1.8 | 0.035 | 0.727 |
| 2.4 | 0.131 | 4.943 |
| 5.21 | 0.095 | 4.847 |
| 5.27 | 0.013 | 2.026 |
| 3.3 | 0.180 | 4.630 |
| 3.6 | 0.142 | 3.737 |

The invention claimed is:

1. A compound of formula I;

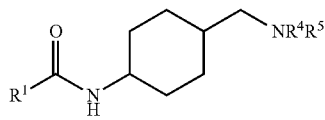

in which $R^1$ is a group:

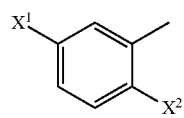

wherein $X^1$ is haloalkyl C1 to 10;

$X^2$ is halogen;

$R^4$ together with $R^5$ and the nitrogen to which they are attached forms a group of formula III;

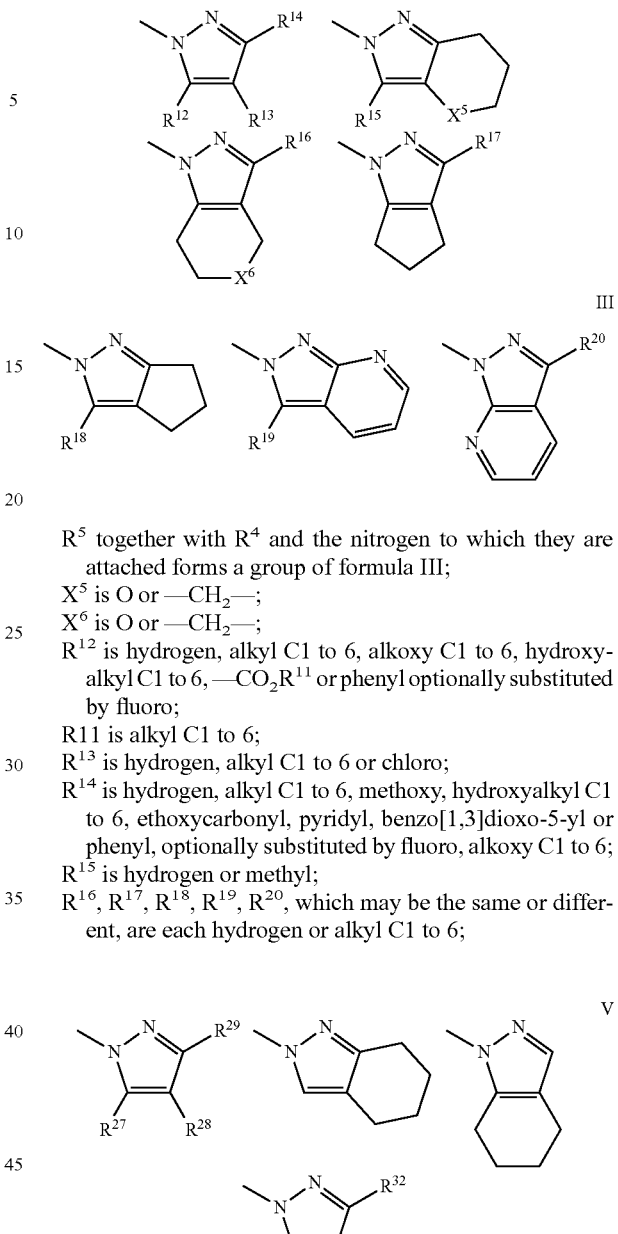

$R^5$ together with $R^4$ and the nitrogen to which they are attached forms a group of formula III;

$X^5$ is O or —$CH_2$—;

$X^6$ is O or —$CH_2$—;

$R^{12}$ is hydrogen, alkyl C1 to 6, alkoxy C1 to 6, hydroxyalkyl C1 to 6, —$CO_2R^{11}$ or phenyl optionally substituted by fluoro;

R11 is alkyl C1 to 6;

$R^{13}$ is hydrogen, alkyl C1 to 6 or chloro;

$R^{14}$ is hydrogen, alkyl C1 to 6, methoxy, hydroxyalkyl C1 to 6, ethoxycarbonyl, pyridyl, benzo[1,3]dioxo-5-yl or phenyl, optionally substituted by fluoro, alkoxy C1 to 6;

$R^{15}$ is hydrogen or methyl;

$R^{16}, R^{17}, R^{18}, R^{19}, R^{20}$, which may be the same or different, are each hydrogen or alkyl C1 to 6;

and stereoisomers thereof;
in free form or in salt form;
provided that the compound of formula I is not:
trans-2-chloro-N-[4-(3,5-dimethyl-pyrazol-1-ylmethyl)-cyclohexyl]-5-trifluoromethyl-benzamide;
trans-2-chloro-N-[4-(3,5-di-(d3)-methyl-pyrazol-1-ylmethyl)-cyclohexyl]-5-trifluoromethyl-benzamide;
trans-2-chloro-N-[4-(5-methyl-pyrazol-1-ylmethyl)-cyclohexyl]-5-trifluoromethyl-benzamide;
trans-2-chloro-N-[4-(3-methyl-pyrazol-1-ylmethyl)-cyclohexyl]-5-trifluoromethyl-benzamide;
trans-2-chloro-N-{4-[3-(4-methoxy-phenyl)-pyrazol-1-ylmethyl]-cyclohexyl}-5-trifluoromethyl-benzamide;
2-chloro-N-[4-(4-chloro-3,5-dimethyl-pyrazol-1-ylmethyl)-cyclohexyl]-5-trifluoromethyl-benzamide;

2-chloro-5-trifluoromethyl-N-[4-(3,4,5-trimethyl-pyrazol-1-ylmethyl)-cyclohexyl]-benzamide;
2-chloro-N-[4-(3-phenyl-pyrazol-1-ylmethyl)-cyclohexyl]-5-trifluoromethyl-benzamide.

2. A compound according to claim 1 which is selected from the group consisting of compounds of formula VI;

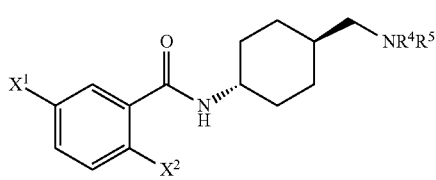

VI in which $R^4$, $R^5$, $X^1$ and $X^2$ are each as defined in claim 1;
and stereoisomers thereof;
in free form or in salt form.

3. A compound according to claim 1 which is selected from the group consisting of compounds of formula VIII;

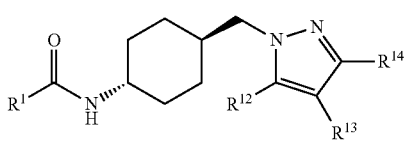

VIII in which $R^1$, $R^{12}$, $R^{13}$ and $R^{14}$ are each as defined in claim 1;
and stereoisomers thereof;
in free form or in salt form.

4. A compound according to claim 1 which is selected from the group consisting of compounds of formula IX or X;

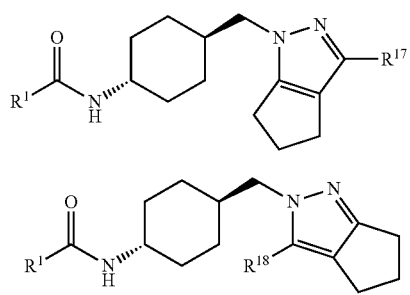

IX

X in which $R^1$, $R^{17}$ and $R^{18}$ are each as defined in claim 1;
and stereoisomers thereof;
in free form or in salt form.

5. A compound according to claim 1 which is selected from the group consisting of compounds of formula XI;

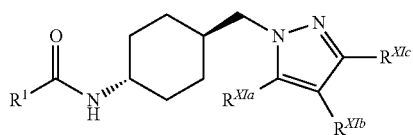

XI in which $R^1$ is as defined in claim 1;

$R^{XIa}$ is hydrogen, alkyl C1 to 6, alkoxy C1 to 6, hydroxyalkyl C1 to 6, —$CO_2R^{11}$ or phenyl optionally substituted by fluoro;
$R^{11}$ is alkyl C1 to 6;
$R^{XIb}$ is hydrogen, deuterium, alkyl C1 to 6 or chloro;
$R^{XIc}$ is hydrogen, alkyl C1 to 6, methoxy, hydroxyalkyl C1 to 6, ethoxycarbonyl, pyridyl, benzo[1,3]dioxo-5-yl or phenyl, optionally substituted by fluoro, alkoxy C1 to 6;
provided that at least one of $R^{XIa}$, $R^{XIb}$ and $R^{XIc}$ comprises one or more deuterium moieties;
and stereoisomers thereof;
in free form or in salt form.

6. A compound according to claim 1 which is selected from the group consisting of:
trans-2-chloro-N-{4-[3-(4-fluoro-phenyl)-5-methyl-pyrazol-1-ylmethyl]-cyclohexyl}-5-trifluoromethyl-benzamide;
trans-2-chloro-N-[4-(4-chloro-3-methoxy-5-methyl-pyrazol-1-ylmethyl)-cyclohexyl]-5-trifluoromethyl-benzamide;
trans-2-chloro-N-[4-(4-chloro-5-methoxy-3-methyl-pyrazol-1-ylmethyl)-cyclohexyl]-5-trifluoromethyl-benzamide;
trans-2-chloro-N-[4-(3,4-dimethyl-pyrazol-1-ylmethyl)-cyclohexyl]-5-trifluoromethyl-benzamide;
trans-2-chloro-N-[4-(4,5-dimethyl-pyrazol-1-ylmethyl)-cyclohexyl]-5-trifluoromethyl-benzamide;
trans-2-chloro-N-[4-(5,6-dihydro-4H-cyclopentapyrazol-1-ylmethyl)-cyclohexyl]-5-trifluoromethyl-benzamide;
trans-2-chloro-N-[4-(5,6-dihydro-4H-cyclopentapyrazol-2-ylmethyl)-cyclohexyl]-5-trifluoromethyl-benzamide;
trans-N-[4-(3-Benzo[1,3]dioxol-5-yl-5-methyl-pyrazol-1-ylmethyl)-cyclohexyl]-2-chloro-5-trifluoromethyl-benzamide;
trans-2-chloro-N-{4-[3-(4-methoxy-phenyl)-5-methyl-pyrazol-1-ylmethyl]-cyclohexyl}-5-trifluoromethyl-benzamide;
trans-2-chloro-N-(4-pyrazolo[3,4-b]pyridin-2-ylmethyl-cyclohexyl)-5-trifluoromethyl-benzamide;
trans-2-chloro-N-(4-pyrazolo[3,4-b]pyridin-1-ylmethyl-cyclohexyl)-5-trifluoromethyl-benzamide;
trans-2-chloro-N-[4-(3,5-diethyl-pyrazol-1-ylmethyl)-cyclohexyl]-5-trifluoromethyl-benzamide;
trans-2-chloro-N-[4-(4-chloro-3,5-diethyl-pyrazol-1-ylmethyl)-cyclohexyl]-5-trifluoromethyl-benzamide;
trans-2-chloro-N-[4-(3-methyl-pyrazolo[3,4-b]pyridin-2-ylmethyl)-cyclohexyl]-5-trifluoromethyl-benzamide;
trans-2-chloro-N-[4-(3-methyl-pyrazolo[3,4-b]pyridin-1-ylmethyl)-cyclohexyl]-5-trifluoromethyl-benzamide;
trans-2-chloro-N-[4-(3-pyridin-4-yl-pyrazol-1-ylmethyl)-cyclohexyl]-5-trifluoromethyl-benzamide;
trans-2-chloro-N-[4-(3-methoxy-5-methyl-pyrazol-1-ylmethyl)-cyclohexyl]-5-trifluoromethyl-benzamide;
trans-2-chloro-N-[4-(3-methyl-5-phenyl-pyrazol-1-ylmethyl)-cyclohexyl]-5-trifluoromethyl-benzamide;
trans-2-chloro-N-[4-(5-methyl-3-phenyl-pyrazol-1-ylmethyl)-cyclohexyl]-5-trifluoromethyl-benzamide;
trans-2-chloro-N-[4-(5-methoxy-3-methyl-pyrazol-1-ylmethyl)-cyclohexyl]-5-trifluoromethyl-benzamide;
trans-2-chloro-N-[4-(3-methyl-5,6-dihydro-4H-cyclopentapyrazol-1-ylmethyl)-cyclohexyl]-5-trifluoromethyl-benzamide;
trans-2-chloro-N-[4-(3-methyl-5,6-dihydro-4H-cyclopentapyrazol-2-ylmethyl)-cyclohexyl]-5-trifluoromethyl-benzamide;
trans-2-chloro-N-[4-(4-chloro-3,5-d6-dimethyl-pyrazol-1-ylmethyl)-cyclohexyl]-5-trifluoromethyl-benzamide;

trans-2-chloro-N-[4-(4-methyl-pyrazol-1-ylmethyl)-cyclohexyl]-5-trifluoromethyl-benzamide;
trans-2-chloro-N-(4-pyrazol-1-ylmethyl-cyclohexyl)-5-trifluoromethyl-benzamide;
trans-2-chloro-N-[4-(4,5,6,7-tetrahydro-indazol-1-ylmethyl)-cyclohexyl]-5-trifluoromethyl-benzamide;
trans-2-chloro-N-[4-(4,5,6,7-tetrahydro-indazol-2-ylmethyl)-cyclohexyl]-5-trifluoromethyl-benzamide;
trans-2-chloro-N-[4-(4-chloro-3-hydroxymethyl-pyrazol-1-ylmethyl)-cyclohexyl]-5-trifluoromethyl-benzamide;
trans-4-chloro-1-[4-(2-chloro-5-trifluoromethyl-benzoylamino)-cyclohexylmethyl]-1H-pyrazole-3-carboxylic acid ethyl ester;
trans-1-[4-(2-chloro-5-trifluoromethyl-benzoylamino)-cyclohexylmethyl]-4-methyl-1H-pyrazole-3-carboxylic acid ethyl ester;
trans-4-chloro-2-[4-(2-chloro-5-trifluoromethyl-benzoylamino)-cyclohexylmethyl]-2H-pyrazole-3-carboxylic acid ethyl ester;
trans-2-[4-(2-chloro-5-trifluoromethyl-benzoylamino)-cyclohexylmethyl]-4-methyl-2H-pyrazole-3-carboxylic acid ethyl ester;
trans-2-chloro-N-[4-(5-ethyl-3-methyl-pyrazol-1-ylmethyl)-cyclohexyl]-5-trifluoromethyl-benzamide;
trans-2-chloro-N-[4-(3-ethyl-5-methyl-pyrazol-1-ylmethyl)-cyclohexyl]-5-trifluoromethyl-benzamide;
trans-2-chloro-N-[4-(4-chloro-5-ethyl-3-methyl-pyrazol-1-ylmethyl)-cyclohexyl]-5-trifluoromethyl-benzamide;
trans-2-chloro-N-[4-(4-chloro-3-ethyl-5-methyl-pyrazol-1-ylmethyl)-cyclohexyl]-5-trifluoromethyl-benzamide;
trans-2-chloro-N-[4-(4-chloro-5-hydroxymethyl-pyrazol-1-ylmethyl)-cyclohexyl]-5-trifluoromethyl-benzamide;
trans-1-[4-(2-chloro-5-trifluoromethyl-benzoylamino)-cyclohexylmethyl]-1H-pyrazole-3-carboxylic acid ethyl ester;
trans-2-[4-(2-chloro-5-trifluoromethyl-benzoylamino)-cyclohexylmethyl]-2H-pyrazole-3-carboxylic acid ethyl ester;
trans-N-[4-(3,5-Bis-hydroxymethyl-pyrazol-1-ylmethyl)-cyclohexyl]-2-chloro-5-trifluoromethyl-benzamide;
trans-2-chloro-N-[4-(3-hydroxymethyl-5-isopropyl-pyrazol-1-ylmethyl)-cyclohexyl]-5-trifluoromethyl-benzamide;
trans-2-chloro-N-[4-(3,5-diisopropyl-pyrazol-1-ylmethyl)-cyclohexyl]-5-trifluoromethyl-benzamide;
trans-2-chloro-N-[4-(3-methyl-6,7-dihydro-4H-pyrano[4,3-c]pyrazol-1-ylmethyl)-cyclohexyl]-5-trifluoromethyl-benzamide;
trans-2-chloro-N-[4-(3-methyl-6,7-dihydro-4H-pyrano[4,3-c]pyrazol-2-ylmethyl)-cyclohexyl]-5-trifluoromethyl-benzamide;
trans-2-chloro-N-[4-(3-ethyl-4-methyl-pyrazol-1-ylmethyl)-cyclohexyl]-5-trifluoromethyl-benzamide;
trans-2-chloro-N-[4-(5-ethyl-4-methyl-pyrazol-1-ylmethyl)-cyclohexyl]-5-trifluoromethyl-benzamide;
trans-2-chloro-N-[4-(5-isopropyl-4-methyl-pyrazol-1-ylmethyl)-cyclohexyl]-5-trifluoromethyl-benzamide;
trans-2-chloro-N-[4-(3-isopropyl-4-methyl-pyrazol-1-ylmethyl)-cyclohexyl]-5-trifluoromethyl-benzamide;
trans-N-[4-(3-tert-Butyl-pyrazol-1-ylmethyl)-cyclohexyl]-2-chloro-5-trifluoromethyl-benzamide;
and stereoisomers thereof;
in free or in salt form.

7. A method of treatment or alleviation of any state with increased endogenous level of CRF or in which the HPA (hypothalamic pituitary axis) is disregulated, or of various diseases induced or facilitated by CRF which comprises administering to a mammal a therapeutically effective amount of a compound of formula I according to claim 1.

8. A pharmaceutical composition comprising a compound of formula I according to claim 1 in free form or in pharmaceutically acceptable salt form, in association with a pharmaceutically acceptable adjuvant, diluent or carrier.

9. A pharmaceutical composition comprising a compound of formula I according to claim 1 in free form or in pharmaceutically acceptable salt form, in combination with another therapeutically active ingredient, optionally in association with a pharmaceutically acceptable adjuvant, diluent or carrier.

* * * * *